(12) United States Patent
Kanada et al.

(10) Patent No.: US 7,884,128 B2
(45) Date of Patent: Feb. 8, 2011

(54) PROCESS FOR TOTAL SYNTHESIS OF PLADIENOLIDE B AND PLADIENOLIDE D

(75) Inventors: Regina Mikie Kanada, Tsukuba (JP); Daisuke Ito, Tsukuba (JP); Takashi Sakai, Tsukuba (JP); Naoki Asai, Tsukuba (JP); Yoshihiko Kotake, Tsukuba (JP); Jun Niijima, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/764,336

(22) Filed: Apr. 21, 2010

(65) Prior Publication Data

US 2010/0204490 A1   Aug. 12, 2010

Related U.S. Application Data

(62) Division of application No. 11/580,047, filed on Oct. 13, 2006.

(60) Provisional application No. 60/727,845, filed on Oct. 19, 2005.

(30) Foreign Application Priority Data

Oct. 13, 2005  (JP) .............................. 2005-299228

(51) Int. Cl.
*A61K 31/36* (2006.01)
(52) U.S. Cl. ..................................................... 514/465
(58) Field of Classification Search ................... 514/465
See application file for complete search history.

(56) References Cited

U.S. PATENT DOCUMENTS

| 7,026,352 | B1 | 4/2006 | Mizui et al. |
| 2006/0009439 | A1 | 1/2006 | Kotake et al. |
| 2006/0141589 | A1 | 6/2006 | Okuda et al. |
| 2006/0235002 | A1 | 10/2006 | Nagai et al. |
| 2007/0155696 | A1 | 7/2007 | Ishihara et al. |
| 2008/0070286 | A1 | 3/2008 | Machida et al. |

FOREIGN PATENT DOCUMENTS

| EP | 1 548 121 | | 6/2005 |
| EP | 1 770 165 | A1 | 4/2007 |
| EP | 1 911 843 | A1 | 4/2008 |
| JP | 4-352783 | A | 12/1992 |
| WO | WO 02/060890 | A1 | 8/2002 |
| WO | WO 03/099813 | A1 | 12/2003 |
| WO | WO 2004/011459 | A1 | 2/2004 |
| WO | WO 2004/011661 | A2 | 2/2004 |
| WO | WO 2004/050890 | A1 | 6/2004 |
| WO | WO 2005/052152 | A1 | 6/2005 |
| WO | WO 2005/073223 | A1 | 8/2005 |
| WO | WO 2006/009276 | A1 | 1/2006 |
| WO | WO 2006/126723 | A1 | 11/2006 |

OTHER PUBLICATIONS

Kanada et al., "Total Synthesis of the Potent Antitumor Macrolides Pladiendolide B and D", Chem. Inform, vol. 38, Issue 40, Oct. 2, 2007, pp. 4350-4355.

*Primary Examiner*—Rita J Desai
*Assistant Examiner*—John Mabry
(74) *Attorney, Agent, or Firm*—Birch, Stewart, Kolasch & Birch, LLP

(57) ABSTRACT

Process for producing compound of Formula:

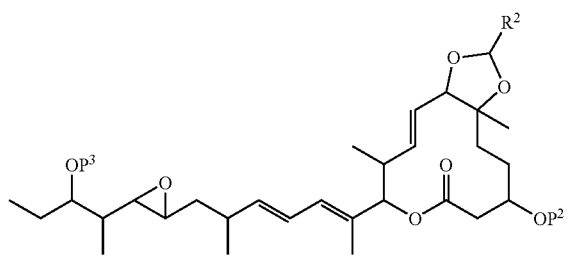

wherein $P^2$, $P^3$ and $R^2$ are the same as defined below, characterized by comprising reacting a compound represented by Formula (7):

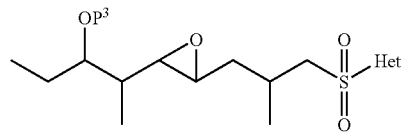

wherein $P^3$ means a protecting group for hydroxy group; and Het means a 1-phenyl-1H-tetrazol-5-yl group, with a compound represented by Formula (8):

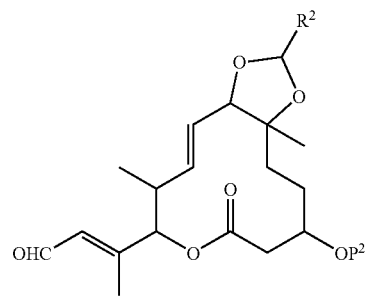

wherein $P^2$ means a protecting group for hydroxy group; and $R^2$ means a phenyl group which may be substituted, in the presence of a base.

2 Claims, No Drawings

PROCESS FOR TOTAL SYNTHESIS OF PLADIENOLIDE B AND PLADIENOLIDE D

CROSS-REFERENCE

This application is a Divisional of co-pending application Ser. No. 11/580,047, filed on Oct. 13, 2006, for which priority is claimed under 35 U.S.C. §120. application Ser. No. 11/580,047 in turn claims priority under 35 U.S.C. §119(e) to U.S. Provisional Application No. 60/727,845, filed on Oct. 19, 2005, and Application No. 2005-299228 filed in Japan on Oct. 13, 2005 under 25 U.S.C. §119. The entire contents of all of these previous applications are hereby incorporated by reference.

TECHNICAL FIELD

The present invention relates to a process for total synthesis of pladienolide B and pladienolide D having excellent anti-tumor activity and intermediates in the above-described process.

BACKGROUND ART

Pladienolide B represented by Formula (1'):

[Formula 1]

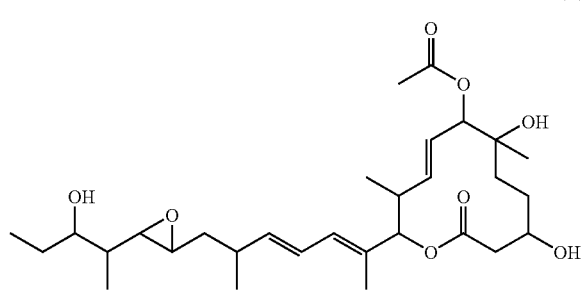

(1')

and Pladienolide D represented by Formula (2'):

[Formula 2]

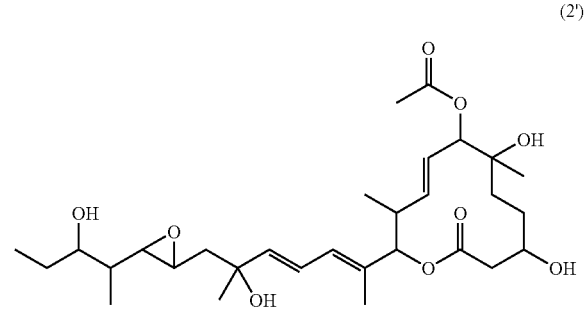

(2')

are 12 membered-ring macrolide compounds found by Sakai et al. in a culture of Streptomyces sp. Mer-11107 strain, and are known to have excellent anti-tumor activity (See Patent Document 1).

However, total synthesis of pladienolide B and pladienolide D has not been reported at all till now, and the purification of the above culture has been the only process for acquiring pladienolide B and pladienolide D. In addition, there was a problem that there was limitation in the structural variety of derivatives obtained by chemical conversion from pladienolide B and pladienolide D themselves which were fermentation products. Furthermore, absolute configuration of pladienolide B and pladienolide D has not yet been determined (See Patent Document 1), and the determination thereof has been a problem to be solved. Accordingly, establishment of a process for total synthesis of pladienolide B and pladienolide D has been strongly desired from the viewpoints of (1) supply of pladienolide B and pladienolide D by chemical synthesis, (2) synthesis of various pladienolide derivatives and (3) determination of absolute configuration of pladienolide B and pladienolide D.

In the meantime, although compounds analogous to pladienolide B and pladienolide D in structure were disclosed in Patent Documents 1 to 5, total synthesis of these compounds was not disclosed in any of the documents.

[Patent Document 1] WO02/60890 pamphlet

[Patent Document 2] JP-A-04-352783

[Patent Document 3] WO03/099813 pamphlet

[Patent Document 4] WO2004/011459 pamphlet

[Patent Document 5] WO2004/011611 pamphlet

DISCLOSURE OF THE INVENTION

Problems to be Solved by the Invention

An object of the present invention is to provide an effective process for total synthesis of pladienolide B and pladienolide D having excellent anti-tumor activity and to provide useful intermediates in the above-described process.

Measure for Solving the Problem

In view of the above circumstances, the present inventors have conducted intensive studies and as a result found an effective process for total synthesis of pladienolide B and pladienolide D and useful intermediates in the above-described process and thus completed the present invention.

That is, the present invention provides,

[1] A process for producing a compound represented by Formula (1):

[Formula 4]

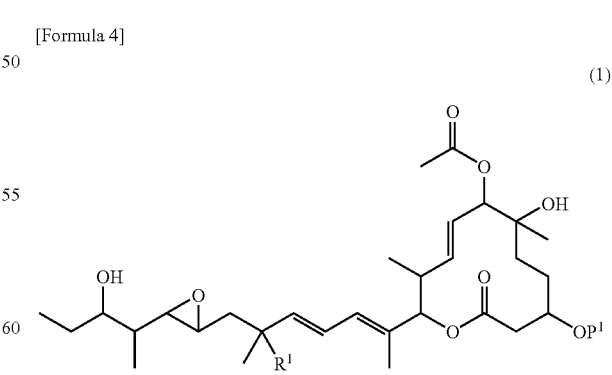

(1)

wherein $P^1$ means a hydrogen atom or a protecting group for hydroxy group; and $R^1$ means a hydrogen atom or a hydroxy group, characterized by comprising reacting a compound represented by Formula (2):

[Formula 3]

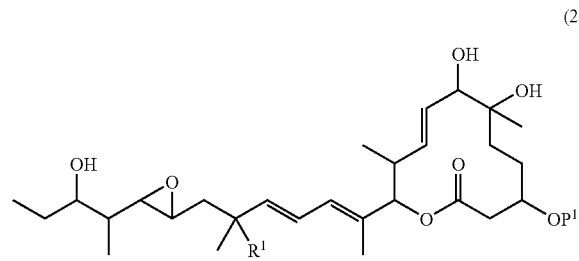

(2)

wherein $P^1$ and $R^1$ are the same as defined above, with an acetylating agent in the presence of a base;

[2] The production process according to [1], wherein the acetylating agent is acetic anhydride;

[3] The production process according to [1] or [2], wherein the base is a combination of triethylamine with 4-dimethylaminopyridine;

[4] The production process according to any one of [1] to [3] wherein the compound represented by Formula (2) in which $P^1$ and $R^1$ are hydrogen atoms is obtained by removing protecting groups for hydroxy group at 3- and 21-positions of a compound represented by Formula (6):

[Formula 5]

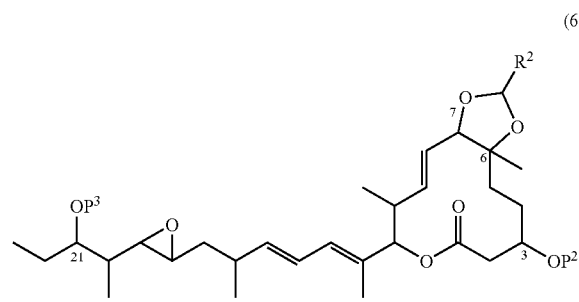

(6)

wherein $P^2$ means a protecting group for hydroxy group; $P^3$ means a protecting group for hydroxy group; and $R^2$ means a phenyl group which may have a substituent, to obtain a compound represented by Formula (5):

[Formula 6]

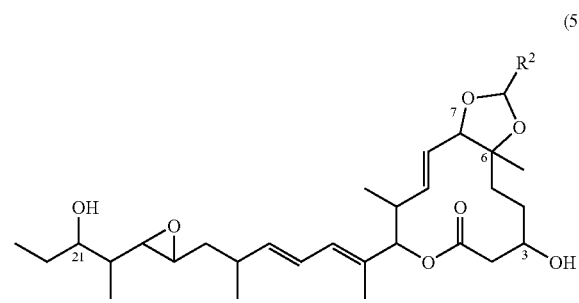

(5)

wherein $R^2$ is the same as defined above, subsequently protecting hydroxy groups at the 3- and 21-positions of Compound (5) to obtain a compound represented by Formula (4):

[Formula 7]

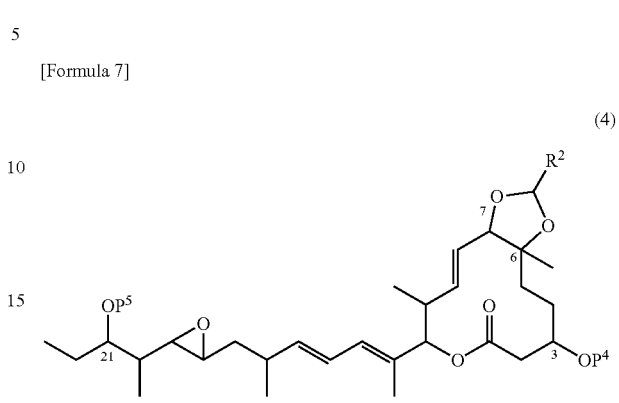

(4)

wherein $P^4$ and $P^5$ mean protecting groups for hydroxy group; and $R^2$ is the same as defined above, subsequently removing protecting groups for hydroxy group at 6- and 7-positions of Compound (4)>—$R^2$ to obtain a compound represented by Formula (3):

[Formula 8]

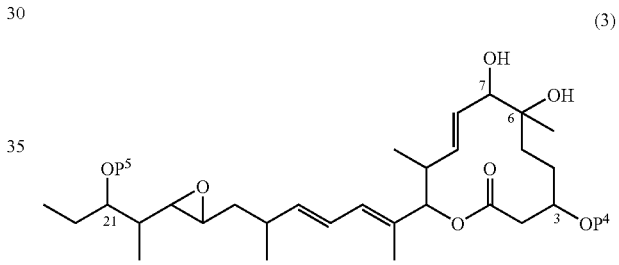

(3)

wherein $P^4$ and $P^5$ are the same as defined above, and subsequently removing protecting groups at 3- and 21-positions of Compound (3);

[5] A process for producing a compound represented by Formula (6):

[Formula 11]

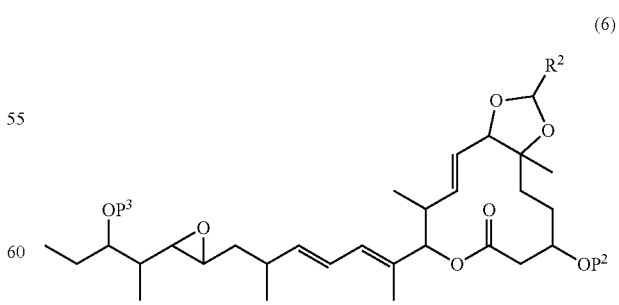

(6)

wherein $P^2$, $P^3$ and $R^2$ are the same as defined below, characterized by comprising reacting a compound represented by Formula (7):

[Formula 9]

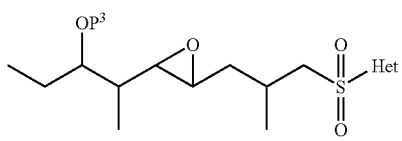
(7)

wherein P³ means a protecting group for hydroxy group; and Het means a 1-phenyl-1H-tetrazol-5-yl group, with a compound represented by Formula (8):

[Formula 10]

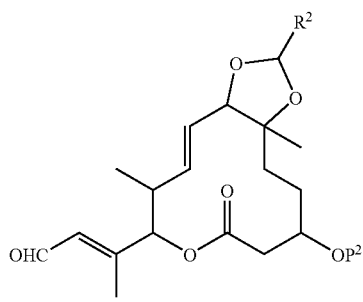
(8)

wherein P² means a protecting group for hydroxy group; and R² means a phenyl group which may have substituents, in the presence of a base;

[6] The production process according to [5], wherein the base is potassium bis(trimethylsilyl)amide;

[7] A process for producing a compound represented by Formula (9):

[Formula 13]

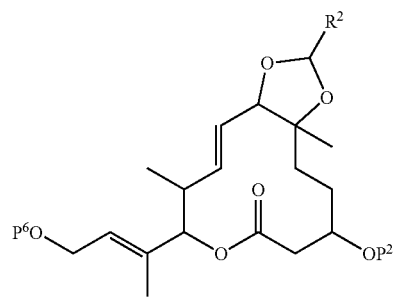
(9)

wherein P², P⁶ and R² are the same as defined below, characterized by comprising closing a ring in a compound represented by Formula (10):

[Formula 12]

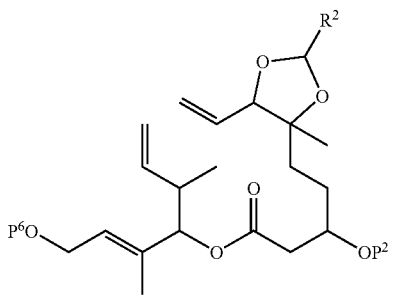
(10)

wherein P² means a protecting group for hydroxy group; R² means a phenyl group which may have substituents; and P⁶ means a protecting group for hydroxy group, in the presence of a catalyst;

[8] The production process according to [7], wherein the catalyst is [1,3-bis-(2,4,6-trimethylphenyl)-2-imidazolidinylidene]dichloro(O-isopropoxyphenylmethylene)ruthenium;

[9] A process for producing a compound represented by Formula (11):

[Formula 17]

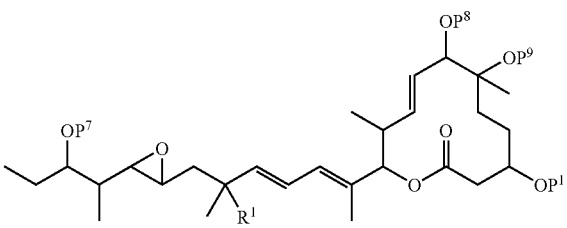
(11)

wherein P¹, P⁷, P⁸, P⁹ and R¹ are the same as defined below, characterized by comprising reacting a compound represented by Formula (12):

[Formula 14]

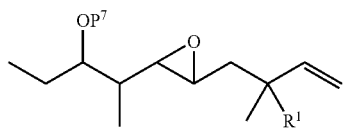
(12)

wherein P⁷ means a hydrogen atom or a protecting group for hydroxy group; and R¹ means a hydrogen atom or a hydroxy group) and a compound represented by Formula (13):

[Formula 15]

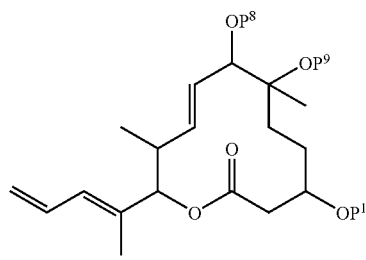
(13)

wherein P¹ means a hydrogen atom or a protecting group for hydroxy group; P⁸ means a hydrogen atom, an acetyl group or a protecting group for hydroxy group; P⁹ means a hydrogen atom or a protecting group for hydroxy group; or P⁸ and P⁹ may form together a group represented by a formula:

[Formula 16]

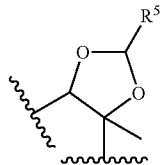

wherein $R^5$ means a phenyl group which may have substituents, in the presence of a catalyst;

[10] The production process according to [9], wherein the catalyst is [1,3-bis-(2,4,6-trimethylphenyl)-2-imidazolidinylidene]dichloro(O-isopropoxyphenylmethylene)ruthenium or tricyclohexylphosphine[1,3-bis(2,4,6-trimethylphenyl)-4,5-dihydroimidazol-2-ylidene][benzylidene]ruthenium (IV) dichloride;

[11] A compound represented by Formula (3-1):

[Formula 18]

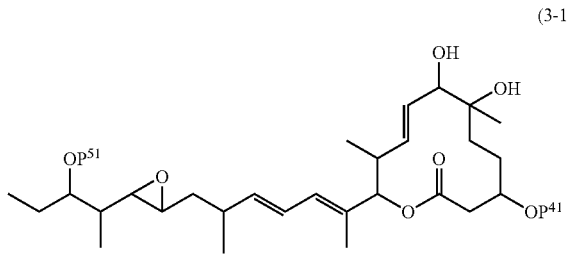

wherein $P^{41}$ and $P^{51}$ may be the same or different and mean a hydrogen atom or a protecting group for hydroxy group, provided that both of $P^{41}$ and $P^{51}$ are or either one of $P^{41}$ or $P^{51}$ is a protecting group for hydroxy group, or a salt thereof;

[12] A compound represented by Formula (4,5,6-1):

[Formula 19]

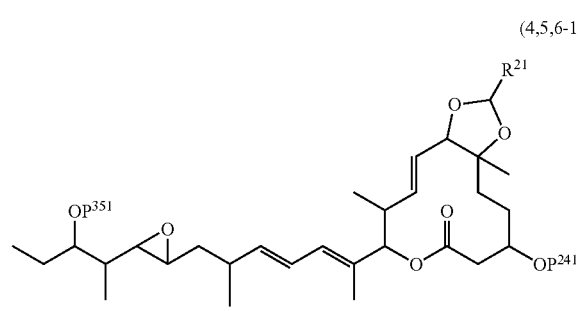

wherein $P^{241}$ means a hydrogen atom or a protecting group for hydroxy group; $P^{351}$ means a hydrogen atom or a protecting group for hydroxy group; and $R^{21}$ means a phenyl group which may have substituents, or a salt thereof;

[13] A compound represented by Formula (7-1):

[Formula 20]

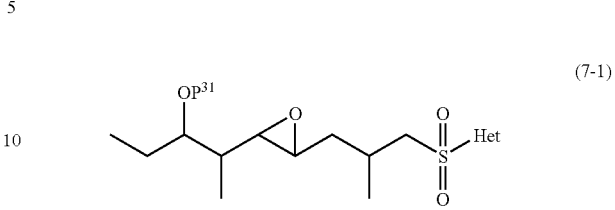

wherein $P^{31}$ means a hydrogen atom or a protecting group for hydroxy group; and Het means a 1-phenyl-1H-tetrazol-5-yl group, or a salt thereof;

[14] A compound represented by Formula (8-1):

[Formula 21]

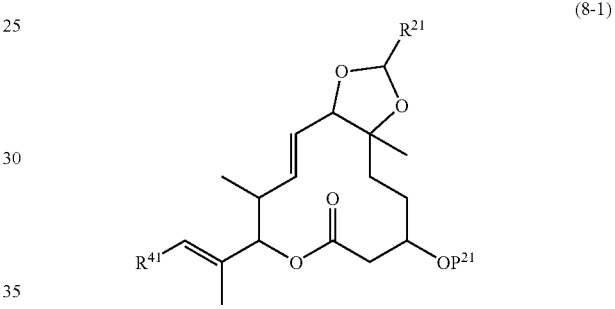

wherein $P^{21}$ means a hydrogen atom or a protecting group for hydroxy group; $R^{21}$ means a phenyl group which may have substituents; and $R^{41}$ means a formyl group or a group represented by —$CH_2OP^{61}$, wherein $P^{61}$ means a hydrogen atom or a protecting group for hydroxy group, or a salt thereof;

[15] A compound represented by Formula (10-1):

[Formula 22]

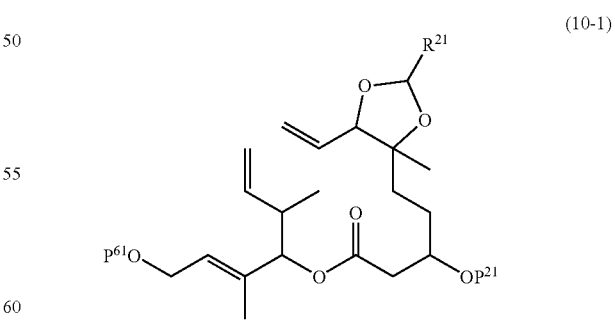

wherein $P^{21}$ means a hydrogen atom or a protecting group for hydroxy group; and $P^{61}$ means a hydrogen atom or a protecting group for hydroxy group; and $R^{21}$ means a phenyl group which may have substituents, or a salt thereof;

[16] A compound represented by Formula (12-1):

[Formula 23]

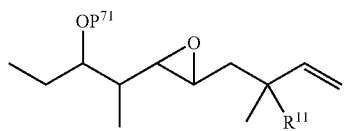

wherein $P^{71}$ means a hydrogen atom or a protecting group for hydroxy group; and $R^{11}$ means a hydrogen atom or a hydroxy group, or a salt thereof;

[17] A compound represented by Formula (13-1):

[Formula 24]

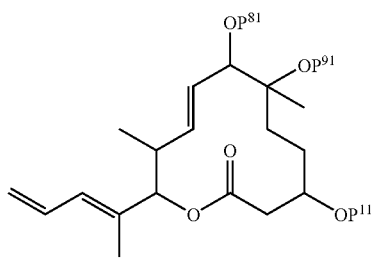

wherein $P^{11}$ means a hydrogen atom or a protecting group for hydroxy group; $P''$ means a hydrogen atom, an acetyl group or a protecting group for hydroxy group; $P^{91}$ means a hydrogen atom or a protecting group for hydroxy group; or $P''$ and $P^{91}$ may form together a group represented by a formula:

[Formula 25]

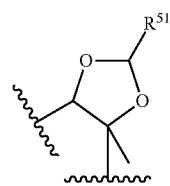

wherein $R^{51}$ means a phenyl group which may have substituents, or a salt thereof;

[18] A process for producing a compound represented by Formula (11'):

[Formula 29]

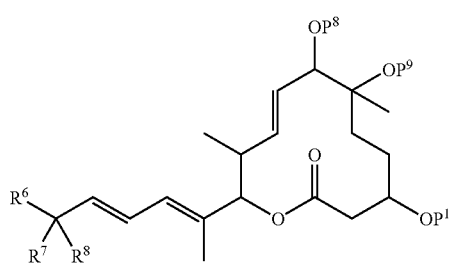

wherein $P^1$, $P^8$, $P^9$, $R^6$, $R^7$ and $R^8$ are the same as defined below, characterized by comprising reacting a compound represented by Formula (12'):

[Formula 26]

wherein $R^6$ means a hydrogen atom or a linear $C_{1-10}$ alkyl group which may have a substituent; $R^7$ means a hydrogen atom or a methyl group; and $R^8$ means a hydrogen atom or a hydroxy group, with a compound represented by Formula (13):

[Formula 27]

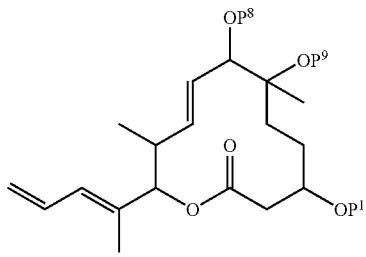

wherein $P^1$ means a hydrogen atom or a protecting group for hydroxy group; $P^8$ means a hydrogen atom, an acetyl group or a protecting group for hydroxy group; and $P^9$ means a hydrogen atom or a protecting group for hydroxy group; or $P^8$ and $P^9$ may form together a group represented by a formula:

[Formula 28]

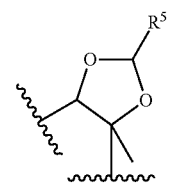

wherein $R^5$ means a phenyl group which may have substituents, in the presence of a catalyst.

[19] A compound represented by Formula (14):

[Formula 30]

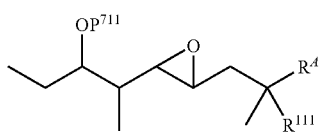

wherein $P^{711}$ means a hydrogen atom or a protecting group for hydroxy group; and $P^{111}$ means hydrogen atom or hydroxy group; and $R^A$ means a formyl group or a group represented by —CH$_2$OH, or a salt thereof.

[20] A compound represented by Formula (15):

[Formula 31]

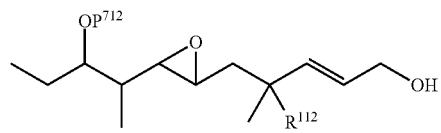

(15)

Wherein $P^{712}$ means a hydrogen atom or a protecting group for hydroxy group; and $R^{112}$ means a hydrogen atom or a hydroxy group, or a salt thereof.

[21] A compound represented by Formula (16):

[Formula 32]

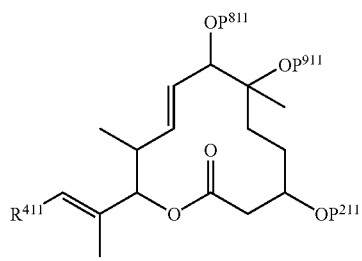

(16)

wherein $P^{211}$ means a hydrogen atom or a protecting group for hydroxy group; and $P^{811}$ means a hydrogen atom, an acetyl group or a protecting group for hydroxy group; and $P^{911}$ means a hydrogen atom or a protecting group for hydroxy group; and $R^{411}$ means a formyl group or a group represented by —CH$_2$OP$^{611}$ (wherein P$^{611}$ means a hydrogen atom or a protecting group for hydroxy group), or a salt thereof.

EFFECT OF THE INVENTION

Pladienolide B and pladienolide D and various kinds of pladienolide derivatives can be effectively synthesized by using a process for total synthesis of pladienolide B and pladienolide D and useful intermediates in the above-described process according to the present invention.

BEST MODE FOR CARRYING OUT THE INVENTION

Hereinbelow, meaning of terms, symbols and the like described in this specification are described and the present invention is described in detail.

The compounds of the present invention or salts thereof may be any of anhydrides, hydrates or solvates.

The "acetylating agent" to be used for producing Compound (1) from Compound (2) includes acetic anhydride and acetyl chloride, and preferably it is acetic anhydride.

The "base" to be used for producing Compound (1) from Compound (2) includes an organic base such as triethylamine, diisopropylethylamine and pyridine, etc. or a combination of the above organic base with 4-dimethylaminopyridine, and preferably it is a combination of triethylamine with 4-dimethylaminopyridine, a combination of diisopropylethylamine with 4-dimethylaminopyridine or a combination of pyridine with 4-dimethylaminopyridine, and more preferably it is a combination of triethylamine with 4-dimethylaminopyridine.

The "base" to be used for producing Compound (6) from Compound (7) and Compound (8) includes potassium bis(trimethylsilyl)amide, sodium bis(trimethylsilyl)amide, lithium bis(trimethylsilyl)amide, etc. and preferably it is potassium bis(trimethylsilyl)amide.

The "catalyst" to be used for producing Compound (9) by closing a ring in Compound (10) includes [1,3-bis-(2,4,6-trimethylphenyl)-2-imidazolidinylidene]dichloro(O-isopropoxyphenylmethylene)ruthenium (following formula (a)), tricyclohexylphosphine[1,3-bis(2,4,6-trimethylphenyl)-4,5-dihydroimidazol-2-ylidene][benzylidene]ruthenium (IV) dichloride (following formula (b)), [1,3-bis-(2,4,6-trimethylphenyl)-2-imidazolidinylidene]dichloro(2-isopropoxy-5-nitrophenylmethylene)ruthenium (following formula (c)), [1,3-bis-(2,4,6-trimethylphenyl)-2-imidazolidinylidene]dichloro(2-isopropoxy-3-phenylphenylmethylene)ruthenium (following formula (d)), [1,3-bis-(2,4,6-trimethylphenyl)-2-imidazolidinylidene]dichloro(2,2'-diisopropoxy-1,1'-binaphthalene-3-ylmethylene)ruthenium (following formula (e)), [1,3-bis-(2,4,6-trimethylphenyl)-2-imidazolidinylidene]dichloro(2-methoxyphenylmethylene)ruthenium (following formula (f)), [1,3-bis-(2,4,6-trimethylphenyl)-2-imidazolidinylidene]dichloro(2,4,5-trimethoxyphenylmethylene)ruthenium (following formula (g)), tricyclohexylphosphine[1,3-bis(2,4,6-trimethylphenyl)-2,3-dihydroimidazol-2-ylidene][benzylidene]ruthenium (IV) dichloride (following formula (h)), bistricyclohexylphosphine[3,3-diphenylprop-2-en-1-ylidene]ruthenium (IV) dichloride (following formula (1)), and bis[3-bromopyridine][1,3-bis(2,4,6-trimethylphenyl)-2-imidazolidinylidene][benzylidene]ruthenium (IV) dichloride (following formula (j)) and preferably it is [1,3-bis-(2,4,6-trimethylphenyl)-2-imidazolidinylidene]dichloro(O-isopropoxyphenylmethylene)ruthenium (following Formula (a)).

[Formula 33]

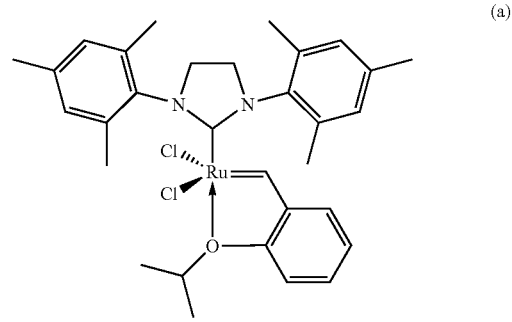

(a)

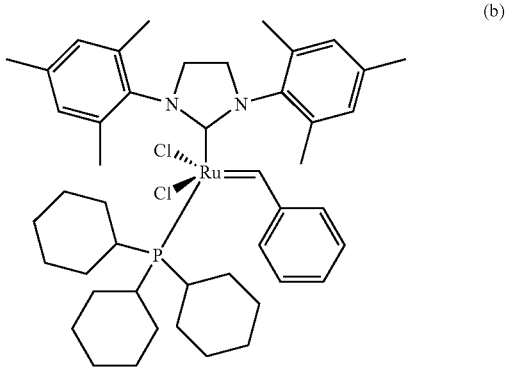

(b)

-continued (c)
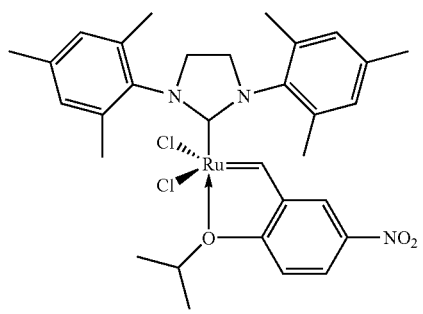

(d)
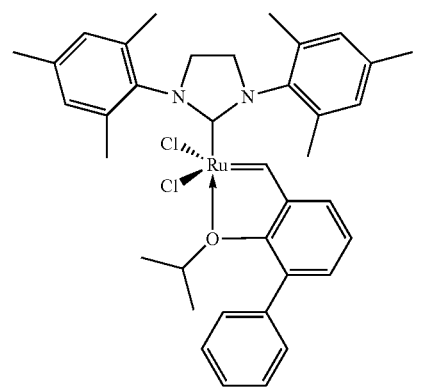

(e)
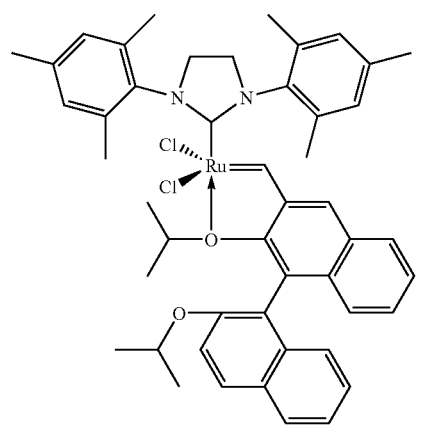

(f)
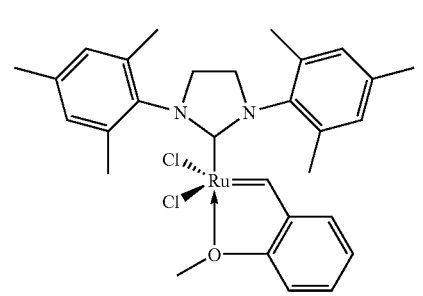

-continued (g)
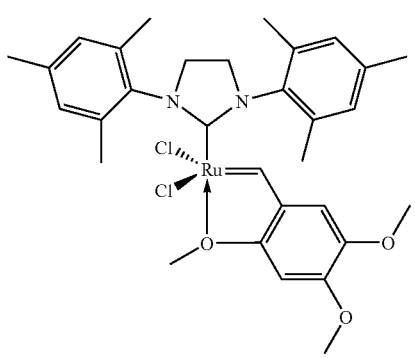

(h)
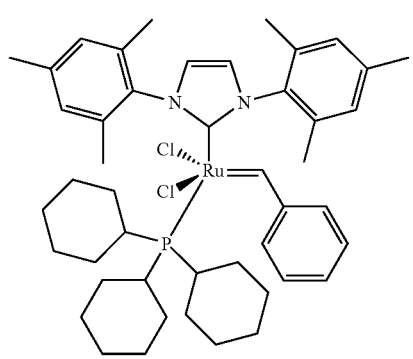

(i)
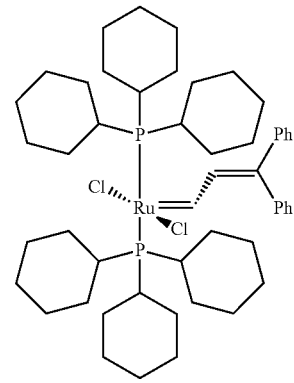

(j)
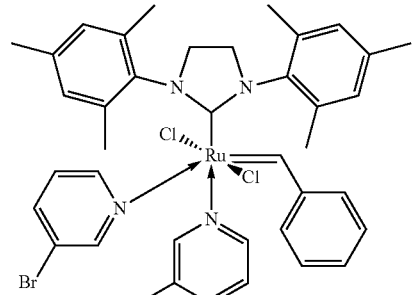

The "catalyst" to be used for producing Compound (11) from Compound (12) and Compound (13) and for producing Compound (11') from Compound (12') and Compound (13) includes [1,3-bis-(2,4,6-trimethylphenyl)-2-imidazolidinylidene]dichloro(O-isopropoxyphenylmethylene) ruthenium (following formula (a)), tricyclohexylphosphine[1,3-bis(2,4,6-trimethylphenyl)-4,5-dihydroimidazol-2-ylidene][benzylidene]ruthenium (IV) dichloride (following formula (b)), [1,3-bis-(2,4,6-trimethylphenyl)-2-imidazolidinylidene]dichloro(2-isopropoxy-5-nitrophenylmethylene)ruthenium (following formula (c)), [1,3-bis-(2,4,6-trimethylphenyl)-2-imidazolidinylidene]dichloro(2-isopropoxy-3-phenylphenylmethylene)ruthenium (following formula (d)), [1,3-bis-(2,4,6-trimethylphenyl)-2-imidazolidinylidene]dichloro(2,2'-diisopropoxy-1,1'-binaphthalene-3-ylmethylene)ruthenium (following formula (e)), [1,3-bis-(2,4,6-trimethylphenyl)-2-imidazolidinylidene]dichloro(2-methoxyphenylmethylene)ruthenium (following formula (f)), [1,3-bis-(2,4,6-trimethylphenyl)-2-imidazolidinylidene]dichloro(2,4,5-trimethoxyphenylmethylene)ruthenium (following formula (g)), tricyclohexylphosphine[1,3-bis(2,4,6-trimethylphenyl)-2,3-dihydroimidazol-2-ylidene][benzylidene]ruthenium (IV) dichloride (following formula (h)), bistricyclohexylphosphine[3,3-diphenylprop-2-en-1-ylidene]ruthenium (IV) dichloride (following formula (i)), bis[3-bromopyridine][1,3-bis(2,4,6-trimethylphenyl)-2-imidazolidinylidene][benzylidene]ruthenium (IV) dichloride (following formula (j)), bistricyclohexylphosphine[benzylidene]ruthenium (IV) dichloride (following formula (k)), and 2,6-diisopropylphenylimidoneophylidenemolybdenium bis(hexafluoro-t-butoxide) (following formula (l)) and preferably it is [1,3-bis-(2,4,6-trimethylphenyl)-2-imidazolidinylidene]dichloro(O-isopropoxyphenylmethylene)ruthenium (following formula (a)) and tricyclohexylphosphine[1,3-bis(2,4,6-trimethylphenyl)-4,5-dihydroimidazol-2-ylidene][benzylidene]ruthenium (IV) dichloride (following formula (b)).

[Formula 34]

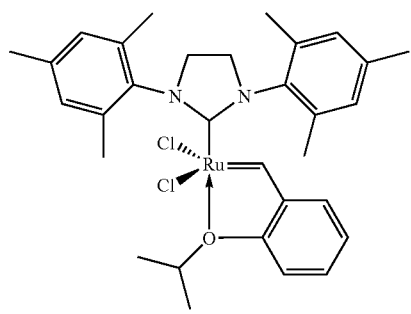

(a)

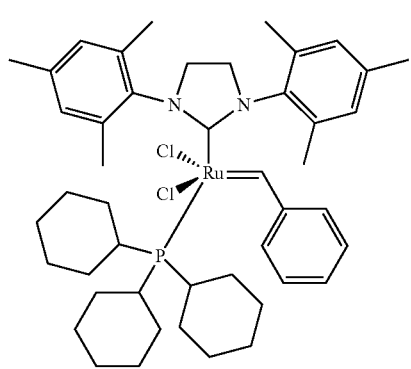

(b)

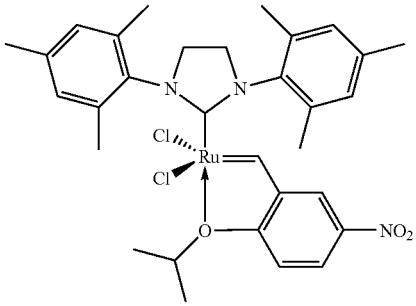

(c)

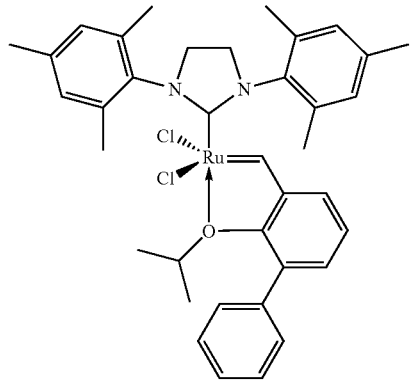

(d)

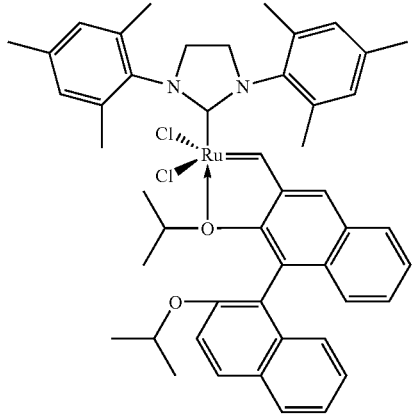

(e)

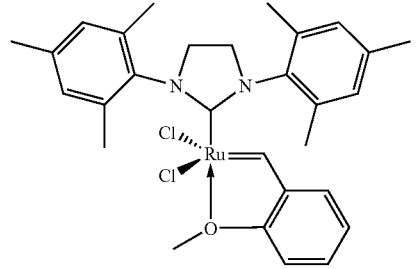

(f)

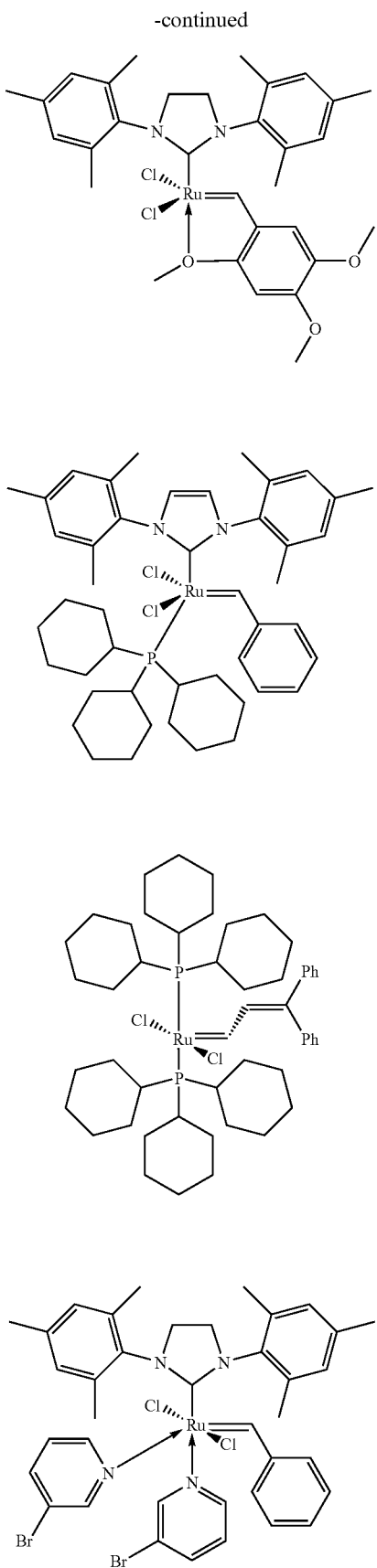

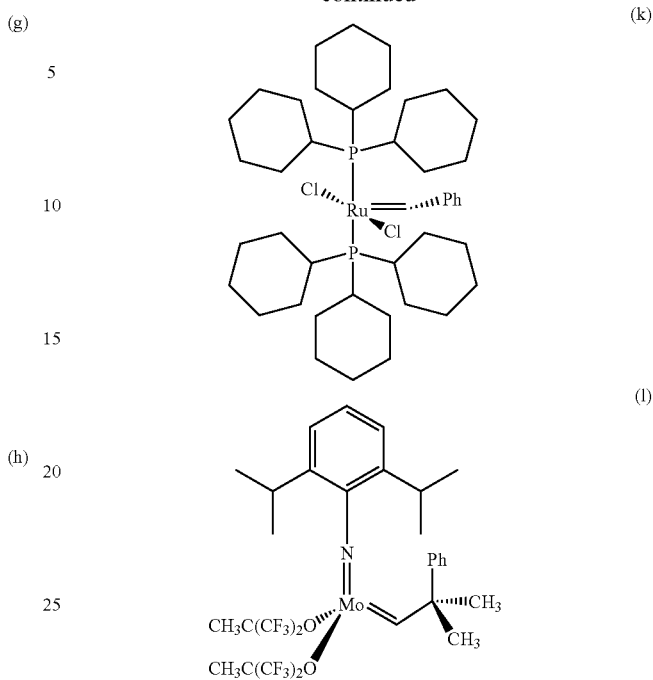

The "protecting group for hydroxy group" as used in this specification is not limited particularly as long as it is a group normally used as a protecting group for hydroxy group in organic synthesis and specific examples thereof include silyl type protecting groups such as tert-butyldimethylsilyl group, tert-butyldiphenylsilyl group, triethylsilyl group, triisopropylsilyl group, trimethylsilyl group, diethylisopropylsilyl group, dimethylisopropylsilyl group, di-tert-butylmethylsilyl group, diphenylmethylsilyl group, trimethylsilylethoxymethyl group and trimethylsilylethyl group, alkoxyalkyl type protecting groups such as methoxymethyl group, 2-methoxyethoxymethyl group, 2,2,2-trichloroethoxymethyl group, 1-ethoxyethyl group, 1-methyl-1-methoxyethyl group and tetrahydropyranyl group, benzyl type protecting groups such as benzyl group, 4-methoxybenzyl group, 3,4-dimethoxybenzyl group, 2,5-dimethoxybenzyl group, 2,3,4-trimethoxybenzyl group, 3,4,5-trimethoxybenzyl group, 2-nitrobenzyl group, 4-nitrobenzyl group, 4-chlorobenzyl group, 2,6-dichlorobenzyl group, 4-cyanobenzyl group, diphenylmethyl group and triphenylmethyl group, acetyl type protecting groups such as acetyl group, chloroacetyl group, dichloroacetyl group, trichloroacetyl group, fluoroacetyl group, difluoroacetyl group, trifluoroacetyl group, bromoacetyl group, tribromoacetyl group, methoxyacetyl group, pivaloyl group and benzoyl group, alkoxycarbonyl type protecting groups such as methoxycarbonyl group, 2,2,2-trichloroethoxycarbonyl group and benzyloxycarbonyl group.

Preferable examples of "protecting group for hydroxy group" in $P^1$ and $P^{11}$ include tert-butyldimethylsilyl group, tert-butyldiphenylsilyl group, triethylsilyl group, triisopropylsilyl group, diethylisopropylsilyl group, dimethylisopropylsilyl group, methoxymethyl group, 1-ethoxyethyl group, tetrahydropyranyl group, benzyl group, benzoyl group, etc. and more preferably it is tert-butyldimethylsilyl group and triethylsilyl group.

Preferable examples of "protecting group for hydroxy group" in $P^2$, $P^{21}$, and $P^{211}$ include tert-butyldimethylsilyl group, tert-butyldiphenylsilyl group, triethylsilyl group, triisopropylsilyl group, diethylisopropylsilyl group, dimethylisopropylsilyl group, 1-ethoxyethyl group etc. and more preferably it is tert-butyldimethylsilyl group.

Preferable examples of "protecting group for hydroxy group" in $P^3$ include tert-butyldimethylsilyl group, tert-butyldiphenylsilyl group, triisopropylsilyl group, diethylisopropylsilyl group, dimethylisopropylsilyl group, etc. and more preferably it is tert-butyldimethylsilyl group, diethylisopropylsilyl group and dimethylisopropylsilyl group, and still more preferably it is diethylisopropylsilyl group.

Preferable examples of "protecting group for hydroxy group" in $P^4$ and $P^5$ include chloroacetyl group, dichloroacetyl group, trichloroacetyl group, fluoroacetyl group, difluoroacetyl group, trifluoroacetyl group, bromoacetyl group, tribromoacetyl group, etc. and more preferably it is dichloroacetyl group.

Preferable examples of "protecting group for hydroxy group" in $P^{241}$ include tert-butyldimethylsilyl group, tert-butyldiphenylsilyl group, triethylsilyl group, triisopropylsilyl group, diethylisopropylsilyl group, dimethylisopropylsilyl group, chloroacetyl group, dichloroacetyl group, trichloroacetyl group, fluoroacetyl group, difluoroacetyl group, trifluoroacetyl group, bromoacetyl group, tribromoacetyl group, etc. and more preferably it is tert-butyldimethylsilyl group and dichloroacetyl group.

Preferable examples of "protecting group for hydroxy group" in $P^{351}$ include tert-butyldimethylsilyl group, tert-butyldiphenylsilyl group, triisopropylsilyl group, diethylisopropylsilyl group, dimethylisopropylsilyl group, chloroacetyl group, dichloroacetyl group, trichloroacetyl group, fluoroacetyl group, difluoroacetyl group, trifluoroacetyl group, bromoacetyl group and tribromoacetyl group, and more preferably it is tert-butyldimethylsilyl group, diethylisopropylsilyl group, dimethylisopropylsilyl group, dichloroacetyl group, etc. and still more preferably it is diethylisopropylsilyl group and dichloroacetyl group.

Preferable examples of "protecting group for hydroxy group" in $P^6$, $P^{61}$ and $P^{611}$ include 4-methoxybenzyl group, 3,4-dimethoxybenzyl group, 2,5-dimethoxybenzyl group, 2,3,4-trimethoxybenzyl group, 3,4,5-trimethoxybenzyl group, etc. and more preferably it is 4-methoxybenzyl group.

Preferable examples of "protecting group for hydroxy group" in $P^7$, $P^{71}$, $P^{711}$ and $P^{712}$ include tert-butyldimethylsilyl group, tert-butyldiphenylsilyl group, triisopropylsilyl group, diethylisopropylsilyl group, dimethylisopropylsilyl group, triethylsilyl group etc. and preferably it is tert-butyldimethylsilyl group, diethylisopropylsilyl group and dimethylisopropylsilyl group, triethylsilyl group and more preferably it is diethylisopropylsilyl group.

Preferable examples of "protecting group for hydroxy group" in $P^8$, $P^{81}$ and $P^{811}$ include tert-butyldimethylsilyl group, tert-butyldiphenylsilyl group, triethylsilyl group, triisopropylsilyl group, diethylisopropylsilyl group, dimethylisopropylsilyl group, methoxymethyl group, 1-ethoxyethyl group, tetrahydropyranyl group, benzyl group, benzoyl group, etc.

Preferable examples of "protecting group for hydroxy group" in $P^9$, $P^{91}$ and $P^{911}$ include methoxymethyl group, 1-ethoxyethyl group, etc.

Specific examples of "phenyl group which may have a halogen atom" in $R^2$ and $R^5$ include phenyl group, 4-chlorophenyl group, 4-bromophenyl group, etc. and preferably it is phenyl group.

Specific examples of "phenyl group which may have a substituent" in $R^{21}$ and $R^{51}$ include phenyl group, 4-chlorophenyl group, 4-bromophenyl group, 4-nitrophenyl group, 4-methoxyphenyl group, 2,4-dimethoxyphenyl group, 3,4-dimethoxyphenyl group, etc. and preferably it is phenyl group.

Specific examples of "linear $C_{1-10}$ alkyl group" in $R^6$ include methyl group, ethyl group, 1-propyl group, 1-butyl group, 1-pentyl group, 1-hexyl group, 1-heptyl group, 1-octyl group, 1-nonyl group, 1-decyl, etc. and preferably it is 1-heptyl group.

Specific examples of "substituent" in $R^6$ include hydroxy group which may be protected, epoxy group, oxo group, methyl group, methoxy group, phenyl group, tetrahydrofuryl group which may have a methyl group or a hydroxy group which may be protected, etc. and preferably it is hydroxy group, epoxy group, methyl group.

"Het" is 1-phenyl-1H-tetrazol-5-yl group specifically in the above formula, but besides, it may be benzothiazol-2-yl group, etc. and preferably it is 1-phenyl-1H-tetrazol-5-yl group.

The "salt" as used in this specification is not particularly limited as long as it can form a salt of the compound of the present invention, and for example, it includes salts with inorganic bases and, among them, pharmacologically acceptable salts are desirable.

Preferable examples of salt with an inorganic base include alkali metal salt such as lithium salt, sodium salt, and potassium salt, alkaline earth metal salt such as calcium salt and magnesium salt, aluminum salt, and ammonium salt.

The process for production and examples of the present invention are described below in detail. The list of abbreviation used in process for production and examples is shown below.

A List of Abbreviation

Bn: benzyl

Et: ethyl

DEIPS: Diethylisopropylsilyl

DME: 1,2-dimethoxyethane

DMF: N,N-dimethylformamide

Me: methyl

Ph: phenyl

PMB: p-methoxybenzyl; 4-methoxybenzyl

TBS: tert-butyldimethylsilyl

TES: triethylsilyl

THF: tetrahydrofuran

Ts: p-toluenesulfonyl

Production Process 1: Process for Producing Compound (9) Using Cyclization Reaction by Olefin Metathesis

[Formula 35]

(10)

(9)

This step is a step to produce Compound (9) by closing a ring in Compound (10) in a solvent in the presence of a catalyst in the presence or absence of a chemical reagent.

This step can be performed by a commonly used method described in a literature (Handbook of Metathesis Vol. 1-3, Grubbs, R. H. Ed., WILEY-VCH, 2003), etc. More specifically, this step can be performed with reference to the reaction conditions, work up procedures and purification method described in [Step 8] of the Example described below.

This reaction can be performed in a stream of or under atmosphere of an inert gas such as nitrogen and argon.

For Compound (10), Compound (P16) described in the Example described below or a compound which can be easily produced from a commercially available compound by the method which those skilled in the art usually perform can be used.

As for the solvent mentioned above, there is no particular limitation as long as it can dissolve starting materials to some extent and does not obstruct the reaction, for example, aromatic hydrocarbon solvents such as benzene, toluene, xylene, chlorobenzene and dichlorobenzene, halogenated hydrocarbon solvents such as dichloromethane, 1,2-dichloroethane chloroform and carbon tetrachloride can be used and preferably it is an aromatic hydrocarbon solvent such as benzene, toluene, xylene, chlorobenzene and dichlorobenzene.

The above catalyst means [1,3-bis-(2,4,6-trimethylphenyl)-2-imidazolidinylidene]dichloro(O-isopropoxyphenylmethylene)ruthenium, tricyclohexylphosphine[1,3-bis(2,4,6-trimethylphenyl)-4,5-dihydroimidazol-2-ylidene][benzylidene]ruthenium (IV) dichloride, [1,3-bis-(2,4,6-trimethylphenyl)-2-imidazolidinylidene]dichloro(2-isopropoxy-5-nitrophenylmethylene)ruthenium, [1,3-bis-(2,4,6-trimethylphenyl)-2-imidazolidinylidene]dichloro(2-isopropoxy-3-phenylphenylmethylene)ruthenium, [1,3-bis-(2,4,6-trimethylphenyl)-2-imidazolidinylidene]dichloro(2,2'-diisopropoxy-1,1'-binaphthalene-3-ylmethylene)ruthenium, [1,3-bis-(2,4,6-trimethylphenyl)-2-imidazolidinylidene]dichloro(2-methoxyphenylmethylene)ruthenium, [1,3-bis-(2,4,6-trimethylphenyl)-2-imidazolidinylidene]dichloro(2,4,5-trimethoxyphenylmethylene)ruthenium, tricyclohexylphosphine[1,3-bis(2,4,6-trimethylphenyl)-2,3-dihydroimidazol-2-ylidene][benzylidene]ruthenium (IV) dichloride, bistricyclohexylphosphine[3,3-diphenylprop-2-en-1-ylidene]ruthenium (IV) dichloride, and bis[3-bromopyridine][1,3-bis(2,4,6-trimethylphenyl)-2-imidazolidinylidene][benzylidene]ruthenium (IV) dichloride and the like but preferably it is [1,3-bis-(2,4,6-trimethylphenyl)-2-imidazolidinylidene]dichloro(O-isopropoxyphenylmethylene)ruthenium.

The above catalyst can be used in 0.001 to 1 time molar equivalent to Compound (10), and preferably it can be used in 0.01 to 1 molar equivalent.

The above chemical reagent means 2,6-di-tert-butyl-4-methylphenol (BHT), 1,4-benzoquinone, titanium triisopropoxide, etc.

The reaction temperature usually varies depending on starting materials, solvents and the other chemical reagents used in the reaction, and preferably it is 40° C. to reflux temperature (internal temperature of the reaction vessel), and more preferably it is 80° C. to reflux temperature (internal temperature of the reaction vessel) and still more preferably it is reflux temperature (internal temperature of the reaction vessel).

The reaction time usually varies depending on starting materials, solvents and the other chemical reagents used in the reaction and reaction temperature, and it is preferable to stir the reaction solution at the above reaction temperature for 0.5 to 48 hours after adding the chemical reagents, and it is more preferable to stir for 1 to 8 hours, and it is still more preferable to stir for about 5 hours.

Production Process 2: Process for Producing Compound (6) Using Julia Coupling

[Formula 36]

(7)

(8)

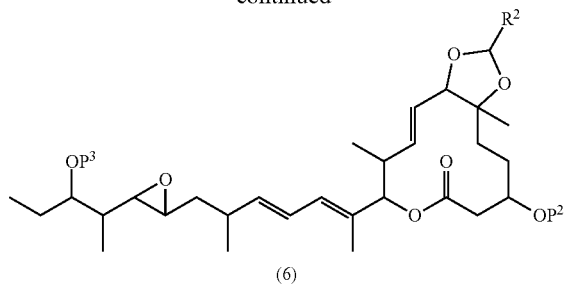

(6)

This step is a step to produce Compound (6) by reacting Compound (7) and Compound (8) in a solvent in the presence of a base.

This step can be performed by a commonly used method described in a literature (Blakemore, P. R.; Cole, W. J.; Kociensky, P. J.; Morley, A., Synlett, 1998, 26-28), etc. More specifically, this step can be performed with reference to the reaction conditions, work up procedures and purification method described in [Step 17] of the Example described below.

This reaction can be performed in a stream of or under atmosphere of an inert gas such as nitrogen and argon.

For Compound (7), Compound (P35) described in the Example described below or a compound which can be easily produced from a commercially available compound by the method which those skilled in the art usually perform can be used.

For Compound (8), Compound (P19) described in the Example described below or a compound which can be easily produced from a commercially available compound by the method which those skilled in the art usually perform can be used.

Compound (8) can be used in 1 to 3 times molar equivalent to Compound (7), and preferably it can be used in 1 to 2 molar equivalents, more preferably it can be used in 1.5 molar equivalents.

As for the solvent mentioned above, there is no particular limitation as long as it can dissolve starting materials to some extent and does not obstruct the reaction, but, for example, ether solvents such as tetrahydrofuran, 1,2-dimethoxyethane and diethyl ether, aromatic hydrocarbon solvents such as benzene, toluene and xylene, amide solvents such as N,N-dimethylformamide or mixed solvents of a solvent mentioned above with hexamethylphosphoramide (HMPA) or N,N'-dimethylpropyleneurea (DMPU) can be used and preferably it is an ether solvent such as tetrahydrofuran, 1,2-dimethoxyethane and diethyl ether.

The above-described base means potassium bis(trimethylsilyl)amide, sodium bis(trimethylsilyl)amide, lithium bis(trimethylsilyl)amide, lithium diisopropylamide etc. and preferably it is potassium bis(trimethylsilyl)amide.

The above-described base can be used in 1 to 10 times molar equivalent to Compound (7), and preferably it can be used in 1 to 3 molar equivalents, more preferably it can be used in 2 molar equivalents.

The reaction temperature usually varies depending on starting materials, solvents and the other chemical reagents used in the reaction, and preferably it is −78° C. to −60° C. (internal temperature of the reaction vessel), and more preferably it is −78° C. (internal temperature of the reaction vessel).

The reaction time usually varies depending on starting materials, solvents and the other chemical reagents used in the reaction and reaction temperature, and it is preferable to stir the reaction solution at the above reaction temperature for 0.5 to 12 hours after adding the chemical reagents, and it is more preferable to stir for about 1 hour.

Production Process 3: Conversion from Compound (6) to Compound (2) (the Case where $P^1$ and $R^1$ are Hydrogen Atoms)

(a) Conversion from Compound (6) to Compound (5)

[Formula 37]

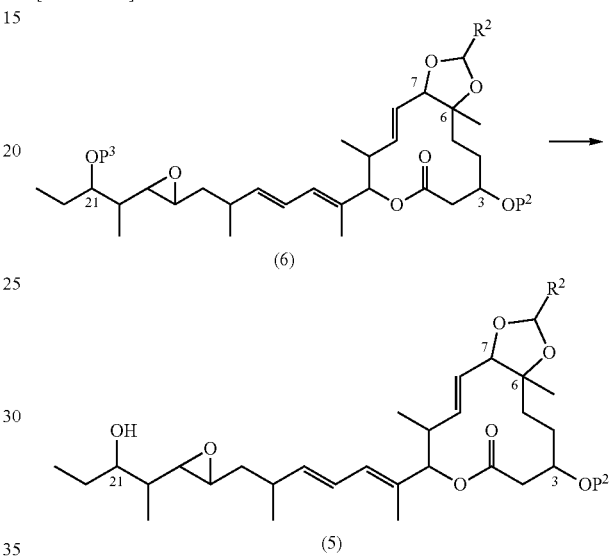

This step is a step to remove protecting groups of hydroxy group at 3- and 21-positions of Compound (6) in a solvent in the presence of a chemical reagent to produce Compound (5).

This step can be performed by a commonly used method described in a literature (Protective Groups in Organic Synthesis 3rd Edition, Green, T. W.; Wuts, P. G. M., Wiley-interscience, 1999), etc. More specifically, this step can be performed with reference to the reaction conditions, work up procedures and purification method described in [Step 17] of the Example described below.

As for the solvent mentioned above, there is no particular limitation as long as it can dissolve starting materials to some extent and does not obstruct the reaction, but, for example, ether solvents such as tetrahydrofuran, 1,2-dimethoxyethane and diethyl ether, alcohol solvents such as methanol and ethanol, acetonitrile, water, etc. can be used and preferably it is an ether solvent such as tetrahydrofuran, 1,2-dimethoxyethane and diethyl ether.

As for the chemical reagent mentioned above, for example, inorganic acids such as hydrochloric acid, sulfuric acid, hydrofluoric acid and perchloric acid, organic acids such as p-toluenesulfonic acid, pyridinium p-toluenesulfonate (PPTS), trifluoromethanesulfonic acid, methanesulfonic acid, acetic acid and trifluoroacetic acid, fluoride ion type chemical reagents such as tetra-n-butylammonium fluoride, potassium fluoride, cerium fluoride, hydrogen fluoride, hydrogen fluoride-pyridine can be used and preferably it is a fluoride ion type chemical reagent such as tetra-n-butylammonium fluoride, potassium fluoride, cerium fluoride, hydrogen fluoride and hydrogen fluoride-pyridine.

The above-described chemical reagent can be used in 2 to 10 molar equivalents to Compound (6), and preferably it can be used in 2 to 5 molar equivalents.

The reaction temperature usually varies depending on starting materials, solvents and the other chemical reagents used in the reaction, and preferably it is −20° C. to 50° C. (internal temperature of the reaction vessel), and more preferably it is 0° C. to 40° C. (internal temperature of the reaction vessel), and still more preferably it is room temperature (internal temperature of the reaction vessel).

The reaction time usually varies depending on starting materials, solvents and the other chemical reagents used in the reaction and reaction temperature, and it is preferable to stir the reaction solution at the above reaction temperature for 0.5 to 48 hours after adding the chemical reagents, and it is more preferable to stir for 0.5 to 12 hours, and it is still more preferable to stir for about 1 hour.

(b) Conversion from Compound (5) to Compound (4)

[Formula 38]

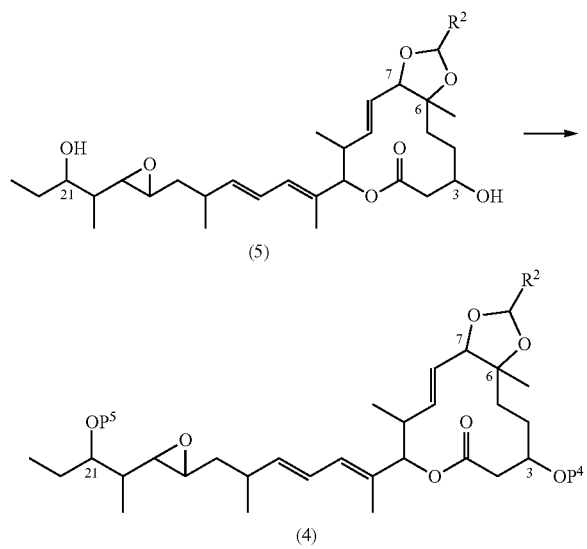

This step is a step to protect hydroxy groups at 3- and 21-positions of Compound (5) in a solvent in the presence of a chemical reagent and a base to produce Compound (4).

This step can be performed by a commonly used method described in a literature (Protective Groups in Organic Synthesis 3rd Edition, Green, T. W.; Wuts, P. G. M., Wiley-interscience, 1999), etc. More specifically, this step can be performed with reference to the reaction conditions, work up procedures and purification method described in [Step 18] of the Example described below.

As for the solvent mentioned above, there is no particular limitation as long as it can dissolve starting materials to some extent and does not obstruct the reaction, but, for example, ether solvents such as tetrahydrofuran, 1,2-dimethoxyethane, diethyl ether, tert-butyl methyl ether and cyclopentyl methyl ether, halogenated hydrocarbon solvents such as dichloromethane, 1,2-dichloroethane and chloroform, etc. can be used and preferably it is a halogenated hydrocarbon solvent such as dichloromethane, 1,2-dichloroethane and chloroform.

As for the chemical reagent mentioned above, for example, chloroacetic anhydride, dichloroacetic anhydride, trichloroacetic anhydride, difluoroacetic anhydride, trifluoroacetic anhydride, bromoacetic anhydride, chloroacetyl chloride, dichloroacetyl chloride, trichloroacetyl chloride, fluoroacetyl chloride, difluoroacetyl chloride, trifluoroacetyl chloride, bromoacetyl chloride can be used and preferably it is dichloroacetic anhydride.

The above-described chemical reagent can be used in 2 to 10 molar equivalents to Compound (5), and preferably it can be used in 2 to 5 molar equivalents.

The above-described base means an organic base such as triethylamine, diisopropylethylamine and pyridine or a combination of the above organic base with 4-dimethylaminopyridine, and preferably it is a combination of triethylamine, diisopropylethylamine or pyridine and 4-dimethylaminopyridine, and more preferably it is a combination of triethylamine with 4-dimethylaminopyridine.

The above-described base can be used in 2 to 10 molar equivalents to Compound (5) (when 4-dimethylaminopyridine is used, 4-dimethylaminopyridine in 0.01 to 1 molar equivalent to Compound (5)), and preferably it can be used in 2 to 3 molar equivalents (0.01 to 0.1 molar equivalent when 4-dimethylaminopyridine is used).

The reaction temperature usually varies depending on starting materials, solvents and the other chemical reagents used in the reaction, and preferably it is −20° C. to −50° C. (internal temperature of the reaction vessel), and more preferably it is 0° C. to 40° C. (internal temperature of the reaction vessel), and still more preferably it is room temperature (internal temperature of the reaction vessel).

The reaction time usually varies depending on starting materials, solvents and the other chemical reagents used in the reaction and reaction temperature, and it is preferable to stir the reaction solution at the above reaction temperature for 5 minutes to 24 hours after adding the chemical reagents, and it is more preferable to stir for 0.5 to 3 hours, and it is still more preferable to stir for 1 to 2 hours.

(c) Conversion from Compound (4) to Compound (3)

[Formula 39]

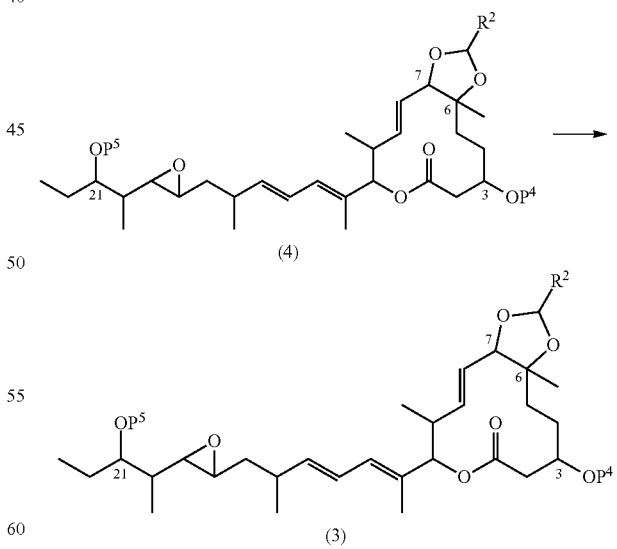

This step is a step to remove protecting groups of hydroxy group at 6- and 7-positions of Compound (4) in a solvent in the presence of a chemical reagent to produce Compound (3).

This step can be performed by a commonly used method described in a literature (Protective Groups in Organic Synthesis 3rd Edition, Green, T. W.; Wuts, P. G. M., Wiley-interscience, 1999), etc. More specifically, this step can be performed with reference to the reaction conditions, work up procedures and purification method described in [Step 18] of the Example described below.

As for the solvent mentioned above, there is no particular limitation as long as it can dissolve starting materials to some extent and does not obstruct the reaction, but, for example, alcohol solvents such as methanol and ethanol, water, etc. can be used and preferably it is an alcohol solvent such as methanol and ethanol.

As for the chemical reagent mentioned above, for example, inorganic acids such as hydrochloric acid, sulfuric acid, hydrofluoric acid and perchloric acid, organic acids such as p-toluenesulfonic acid, pyridinium p-toluenesulfonate (PPTS), trifluoromethanesulfonic acid, methanesulfonic acid, acetic acid and trifluoroacetic acid, etc. can be used and preferably it is pyridinium p-toluenesulfonate (PPTS).

The above-described chemical reagent can be used in 0.05 to 20 times molar equivalent to Compound (4), and preferably it can be used in 0.1 to 10 molar equivalents, and more preferably it can be used in 1 to 2 molar equivalents.

The reaction temperature usually varies depending on starting materials, solvents and the other chemical reagents used in the reaction, and preferably it is 0° C. to 50° C. (internal temperature of the reaction vessel), and more preferably it is room temperature (internal temperature of the reaction vessel).

The reaction time usually varies depending on starting materials, solvents and the other chemical reagents used in the reaction and reaction temperature, and it is preferable to stir the reaction solution at the above reaction temperature for 0.5 to 96 hours after adding the chemical reagents, and it is more preferable to stir for about 48 hours.

(d) Conversion from Compound (3) to Compound (2) (the Case where $P^1$ and $R^1$ are Hydrogen Atoms)

[Formula 40]

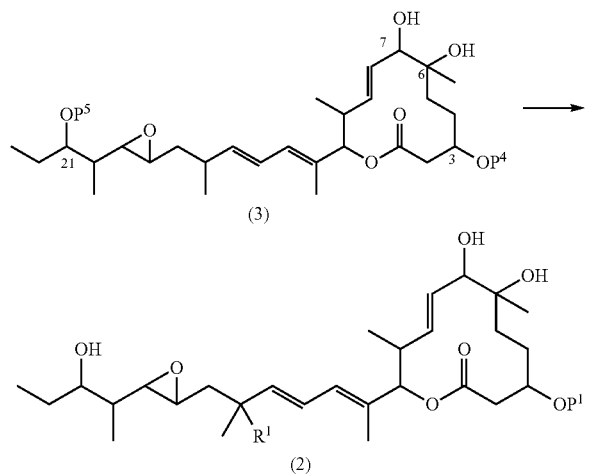

This step is a step to remove protecting groups of hydroxy group at 3- and 21-positions of Compound (3) in a solvent in the presence of a chemical reagent to produce Compound (2) (the case where $P^1$ and $R^1$ are hydrogen atoms).

This step can be performed by a commonly used method described in a literature (Protective Groups in Organic Synthesis 3rd Edition, Green, T. W.; Wuts, P. G. M., Wiley-interscience, 1999), etc. More specifically, this step can be performed with reference to the reaction conditions, work up procedures and purification method described in [Step 18] of the Example described below.

As for the solvent mentioned above, there is no particular limitation as long as it can dissolve starting materials to some extent and does not obstruct the reaction, but, for example, alcohol solvents such as methanol and ethanol, water, etc. can be used and preferably it is an alcohol solvent such as methanol and ethanol.

As for the chemical reagent mentioned above, for example, inorganic bases such as potassium carbonate, sodium carbonate and cesium carbonate, organic bases such as sodium methoxide, potassium methoxide, sodium ethoxide, potassium ethoxide, sodium tert-butoxide and potassium tert-butoxide can be used and preferably it is an inorganic base such as potassium carbonate, sodium carbonate and cesium carbonate.

The above-described chemical reagent can be used in 0.01 to 10 molar equivalents to Compound (3), and preferably it can be used in 0.1 to 2 molar equivalents, and more preferably it can be used in 1 to 1.5 molar equivalents.

The reaction temperature usually varies depending on starting materials, solvents and the other chemical reagents used in the reaction, and preferably it is −20° C. to 70° C. (internal temperature of the reaction vessel), and more preferably it is 0° C. to 50° C. (internal temperature of the reaction vessel), and still more preferably it is room temperature (internal temperature of the reaction vessel).

The reaction time usually varies depending on starting materials, solvents and the other chemical reagents used in the reaction and reaction temperature, and it is preferable to stir the reaction solution at the above reaction temperature for 5 minutes to 24 hours after adding the chemical reagents, and it is more preferable to stir for 10 minutes to 12 hours.

Production Process 4: Process for Producing Compound (1) Using Acetylation Reaction

[Formula 41]

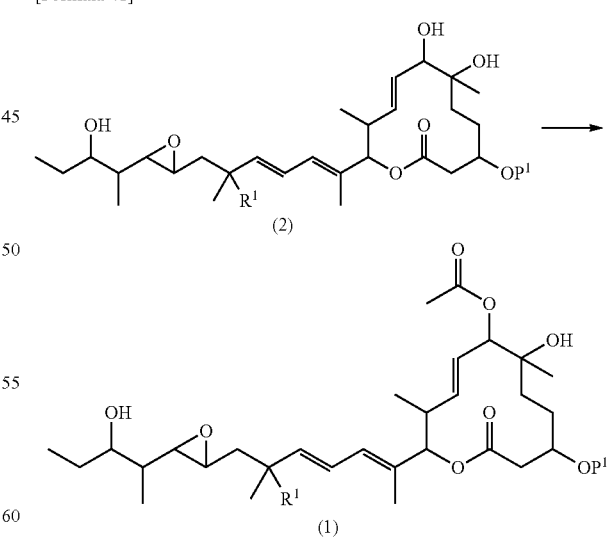

This step is a step to produce Compound (1) by acetylating a hydroxy group at 7-position of Compound (2) in a solvent in the presence of an acetylating agent and a base.

This step can be performed by a commonly used method. More specifically, this step can be performed with reference to the reaction conditions, work up procedures and purification method described in [Step 19] of the Example described below.

This reaction can be performed in a stream of or under atmosphere of an inert gas such as nitrogen and argon.

As for the solvent mentioned above, there is no particular limitation as long as it can dissolve starting materials to some extent and does not obstruct the reaction, for example, ether solvents such as tetrahydrofuran, 1,2-dimethoxyethane, diethyl ether, tert-butyl methyl ether and cyclopentyl methyl ether, halogenated hydrocarbon solvents such as dichloromethane, 1,2-dichloroethane and chloroform, etc. can be used and preferably it is a halogenated hydrocarbon solvent such as dichloromethane, 1,2-dichloroethane and chloroform.

The above acetylating agent means acetic anhydride and acetyl chloride and preferably it is acetic anhydride.

The above-described acetylating agent can be used in 1 to 5 molar equivalents to Compound (2), and preferably it can be used in 0.5 to 1.5 molar equivalents, and more preferably it can be used in 0.8 to 1.2 molar equivalents.

The above-described base means an organic base such as triethylamine, diisopropylethylamine and pyridine or a combination of the above organic base with 4-dimethylaminopyridine, and preferably it is a combination of triethylamine, diisopropylethylamine or pyridine and 4-dimethylaminopyridine, and more preferably it is a combination of triethylamine with 4-dimethylaminopyridine.

The above-described base can be used in 0.5 to 10 molar equivalents to Compound (2) (when 4-dimethylaminopyridine is used, 4-dimethylaminopyridine in 0.01 to 1 molar equivalent to Compound (2)), and preferably it can be used in 0.5 to 5 molar equivalents (0.1 to 1 molar equivalent when 4-dimethylaminopyridine is used), and more preferably it can be used in 0.8 to 1.2 molar equivalents (0.1 to 0.5 molar equivalent when 4-dimethylaminopyridine is used).

The reaction temperature usually varies depending on starting materials, solvents and the other chemical reagents used in the reaction, and preferably it is −20° C. to room temperature (internal temperature of the reaction vessel), and more preferably it is about 0° C. (internal temperature of the reaction vessel).

The reaction time usually varies depending on starting materials, solvents and the other chemical reagents used in the reaction and reaction temperature, and it is preferable to stir the reaction solution at the above reaction temperature 0.5 to 24 hours after adding the chemical reagents, and it is more preferable to stir for 0.5 to 8 hours, and it is still more preferable to stir for about 1 hour.

Production Process 5: Process for Producing Compound (11) and Compound (11') Using Cross Coupling Reaction by Olefin Metathesis

[Formula 42]

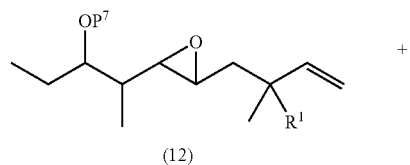

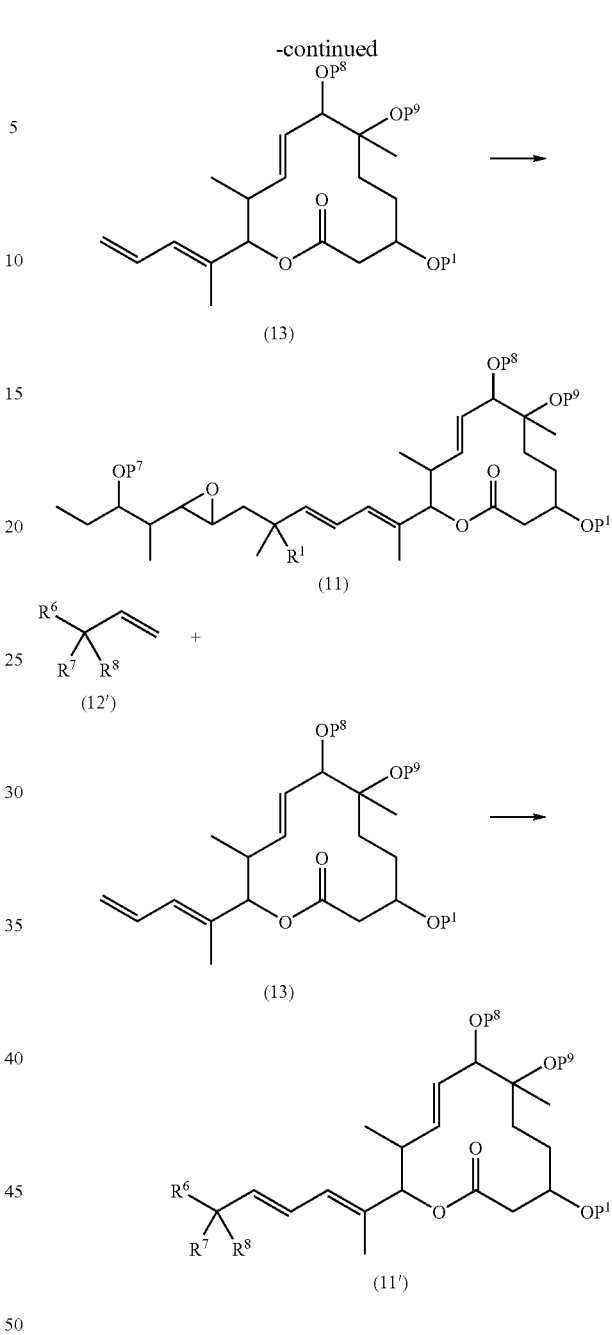

This step is a step to produce Compound (11) or Compound (11') by reacting Compound (12) or Compound (12') with Compound (13) in a solvent in the presence of a catalyst.

This step can be performed by a commonly used method described in a literature (Handbook of Metathesis Vol. 1-3, Grubbs, R. H. Ed., WILEY-VCH, 2003), etc. More specifically, this step can be performed with reference to the reaction conditions, work up procedures and purification method described in [Step D6] of the Example described below.

This reaction can be performed in a stream of or under atmosphere of an inert gas such as nitrogen and argon.

For Compound (12), Compound (Q9) described in the Example described below or a compound which can be easily produced from a commercially available compound by the method which those skilled in the art usually perform can be used.

For Compound (12'), Compound (Q14) described in the Example described below or a compound which can be easily produced from a commercially available compound by the method which those skilled in the art usually perform can be used.

For Compound (13), Compound (Q12) described in the Example described below or a compound which can be easily produced from a commercially available compound by the method which those skilled in the art usually perform can be used.

Compound (12) or Compound (12') can be used in 1 to 10 molar equivalents to Compound (13), and preferably it can be used in 1.5 to 4 molar equivalents, and more preferably it can be used in 2 to 3 molar equivalents.

As for the solvent mentioned above, there is no particular limitation as long as it can dissolve starting materials to some extent and does not obstruct the reaction, but, for example, aromatic hydrocarbon solvents such as benzene, toluene, xylene, chlorobenzene and dichlorobenzene, halogenated hydrocarbon solvents such as dichloromethane, 1,2-dichloroethane, chloroform and carbon tetrachloride, water, methanol, etc. can be used and preferably it is a halogenated hydrocarbon solvents such as dichloromethane, 1,2-dichloroethane, chloroform and carbon tetrachloride.

The above catalyst means [1,3-bis-(2,4,6-trimethylphenyl)-2-imidazolidinylidene]dichloro(O-isopropoxyphenylmethylene) ruthenium, tricyclohexylphosphine[1,3-bis(2,4,6-trimethylphenyl)-4,5-dihydroimidazol-2-ylidene][benzylidene]ruthenium (IV) dichloride, [1,3-bis-(2,4,6-trimethylphenyl)-2-imidazolidinylidene]dichloro(2-isopropoxy-5-nitrophenylmethylene)ruthenium, [1,3-bis-(2,4,6-trimethylphenyl)-2-imidazolidinylidene]dichloro(2-isopropoxy-3-phenylphenylmethylene)ruthenium, [1,3-bis-(2,4,6-trimethylphenyl)-2-imidazolidinylidene]dichloro(2,2'-diisopropoxy-1,1'-binaphthalene-3-ylmethylene)ruthenium, [1,3-bis-(2,4,6-trimethylphenyl)-2-imidazolidinylidene]dichloro(2-methoxyphenylmethylene)ruthenium, [1,3-bis-(2,4,6-trimethylphenyl)-2-imidazolidinylidene]dichloro(2,4,5-trimethoxyphenylmethylene)ruthenium, tricyclohexylphosphine[1,3-bis(2,4,6-trimethylphenyl)-2,3-dihydroimidazol-2-ylidene][benzylidene]ruthenium (IV) dichloride, bistricyclohexylphosphine[3,3-diphenylprop-2-en-1-ylidene]ruthenium (IV) dichloride, bis[3-bromopyridine][1,3-bis(2,4,6-trimethylphenyl)-2-imidazolidinylidene][benzylidene]ruthenium (IV) dichloride, bistricyclohexylphosphine[benzylidene]ruthenium (IV) dichloride, and 2,6-diisopropylphenylimidoneophylidenemolybdenium bis(hexafluoro-t-butoxide) and the like but preferably it is [1,3-bis-(2,4,6-trimethylphenyl)-2-imidazolidinylidene]dichloro(O-isopropoxyphenylmethylene)ruthenium and tricyclohexylphosphine[1,3-bis(2,4,6-trimethylphenyl)-4,5-dihydroimidazol-2-ylidene][benzylidene]ruthenium (IV) dichloride.

The above catalyst can be used in 0.001 to 1 molar equivalent to Compound (13), and preferably it can be used in 0.01 to 0.3 molar equivalent.

The reaction temperature usually varies depending on starting materials, solvents and the other chemical reagents used in the reaction, and preferably it is 20° C. to refluxing temperature (internal temperature of the reaction vessel), and more preferably it is refluxing temperature (internal temperature of the reaction vessel).

The reaction time usually varies depending on starting materials, solvents and the other chemical reagents used in the reaction and reaction temperature, and it is preferable to stir the reaction solution at the above reaction temperature for 0.1 to 96 hours after adding the chemical reagents, and it is more preferable to stir for 0.5 to 12 hours, and it is still more preferable to stir for about 1 hour.

After the reaction of each of the above steps is completed, object compounds in each of the above steps can be taken from the reaction mixture by an usual manner.

EXAMPLES

Hereinbelow, Examples are described in order to facilitate the present invention to be understood, but, needless to say, the present invention is not limited to these.

Determination of Absolute Configuration of Pladienolide B

Test Example 1

Determination of Relative Configuration of Pladienolide B by NMR

[Method]

NMR information ($^1$H-$^1$H coupling constant, $^1$H-$^{13}$C long range coupling constant and NOE correlation) which was necessary for determining relative configuration was obtained under the following conditions.

Device used: Unity INOVA 500 MHz (product of Varian) and JNMα 600 MHz (product of JEOL)

Solvent: deuterated pyridine

Measurement temperature: 30° C.

Sample density: about 20 mg/mL

Measuring method: $^1$H-NMR, $^{13}$C-NMR, COSY, NOESY, HMQC,

HMBC, HETLOC, J-resolved-HMBC, $^1$H-decoupling

[Results]

NMR information shown in the following Table 1 to Table 3 was obtained. The relative configuration of five asymmetric carbons present in macrolactone ring moiety was determined to be (3R*,6R*,7S*,10S*,11S*) from $^1$H-$^1$H coupling constant and NOE correlation. As for relative configuration of five asymmetric carbons present in side-chain moieties, analysis by J-based configuration analysis (N. Matsumori et al, J. Org. Chem., 64, 866-876, 1999) was performed based on $^1$H-$^1$H coupling constant, $^1$H-$^{13}$C long range coupling constant and NOE correlation, and was determined to be (16S*,18R*,19R*,20R*,21S*).

[Formula 43]

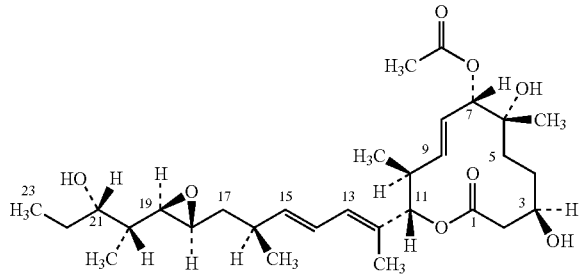

TABLE 1

| position | $\delta_C$ | $\delta_H$ | $J_{HH}$ multiplicity, J = Hz | long range $J_{CH}$, J = Hz | NOESY* |
|---|---|---|---|---|---|
| 1 | 170.9 | — | — | — | — |
| 2α | 40.2 | 2.7 | dd, 14.0, 3.2 | — | H2β(s), H3(m), H4α(n), H4β(n), H5α(n), H5β(w), |
| 2β | | 2.78 | dd, 14.0, 4.0 | — | H2α(s), H3(w), H4α(n), H4β(n), H5α(n), H5β(n), |
| 3 | 69.8 | 4.1 | dddd, 10.0, 4.0, 3.5, 3.5, 3.2 | $^2J_{H2\beta/C3}$ = 4, $^2J_{H2\alpha/C3}$ < 2 | H2α(m), H2β(w), H4α(w), H4β(n), H5α(w), H5β(n) |
| 4α | 30.8 | 1.95 | dddd, 13.5, 13.2, 3.5, 3.5 | — | H2α(n), H2β(n), H3(w), H4β(s), H5α(m), H5β(o), H7(n), H8(n), H9(n), 6-H2α(n), H2β(n), H3(n), |
| 4β | | 1.82 | dddd, 13.5, 13.0, 10.0, 3.7 | — | H4α(s), H5α(o), H5β(w), H7(s), H8(n), H9(w), 6-CH$_3$(n) |
| 5α | 37.7 | 1.71 | ddd, 13.2, 13.0, 3.5 | — | H2α(n), H2β(n), H3(w), H4α(m), H4β(o), H5β(s), H7(n), H8(n), H9(n), 6-CH$_3$(s) |
| 5β | | 2.11 | ddd, 13.2, 13.2, 3.7 | — | H2α(w), H2β(n), H3(n), H4α(o), H4β(w), H5β(s), H7(n), H8(w), H9(n), 6-CH$_3$(n) |
| 6 | 73 | — | | $^3J_{H8/C6}$ < 2 | — |
| 7 | 79.7 | 5.54 | d, 9.8 | $^3J_{H9/C7}$ = 6.5 | H4α(n), H4β(s), H5α(n), H5β(n), H8(w), H9(w), H10(n), 6-CH$_3$(m), 7- |
| 8 | 127.4 | 6.27 | dd, 15.2, 9.8 | $^2J_{H7/C8}$ = 3 | H4α(n), H4β(n), H5α(n), H5β(w), H7(n), H9(w), H10(n), H11(w), 6-CH$_3$(n), 7-COCH$_3$(n), 10-CH$_3$(m) |
| 9 | 140.1 | 5.81 | dd, 15.2, 10.0 | $^3J_{H11/C9}$ = 2.5 | H4α(n), H4β(w), H5α(n), H5β(n), H7(w), H8(w), H10(n), H11(w), 6-CH$_3$(n), 7-COCH$_3$(n), 10-CH$_3$(m) |
| 10 | 40.9 | 2.67 | ddq, 10.7, 10.0, 6.8 | $^3J_{H8/C10}$ = 6, $^2J_{H9/C10}$ = 3, $^2J_{H11/C10}$ = 3 | H7(n), H8(w), H9(n), H11(w), 6-CH$_3$(n), 7-COCH$_3$(n), 10-CH$_3$(s), 12-CH$_3$(s) |
| 11 | 82.9 | 5.33 | d, 10.7 | $^3J_{H9/C11}$ = 2.5, $^3J_{H13/C11}$ = 7 | H2α(n), H2β(n), H7(n), H8(n), H9(w), H10(w), H13(w), 10-CH$_3$(s), 12-CH$_3$(w) |
| 12 | 132 | — | — | $^2J_{H11/C12}$ = 2.5, $^3J_{H14/C12}$ = 3 | — |

TABLE 2

| position | $\delta_C$ | $\delta_H$ | $J_{HH}$ multiplicity, J = Hz | long range $J_{CH}$, J = Hz | NOESY* |
|---|---|---|---|---|---|
| 13 | 131.2 | 6.34 | brd, 11.0 | $^3J_{H11/C13}$ = 5 | H10(n), H11(w), H14(o), H15(w), 10-CH$_3$, 12-CH$_3$(w) |
| 14 | 124.9 | 6.46 | dd, 15.1, 11.0 | — | H11(n), H13(o), H15(w), H16(m), 12-CH$_3$(s), 16- |
| 15 | 141.7 | 5.73 | dd, 15.1, 8.0 | $^3J_{H13/C15}$ = 5, $^3J_{H17\beta/C15}$ = 6, $^3J_{H17\alpha/C15}$ = 3.5 | H13(w), H14(w), H16(w), H17α(n), H17β(n), H18(w), 12-CH$_3$(n), 16-CH$_3$(m) |
| 16 | 35.8 | 2.54 | dddq, 8.5, 8.0, 5.0, 6.8 | $^3J_{H14/C16}$ = 5.5, $^2J_{H17\beta/C16}$ = 4, $^2J_{H17\alpha/C16}$ = 4.5 | H14(m), H15(w), H17α(n), H17β(m), H18(m), H19(n), 16-CH$_3$(s) |
| 17α | 40.1 | 1.56 | ddd, 13.9, 8.5, 5.9 | — | H14(n), H15(n), H16(n), H17β(s), H18(w), H19(m), 16-CH$_3$(o) |
| 17β | | 1.7 | ddd, 13.9, 5.9, 5.0 | — | H14(n), H15(n), H16(m), H17α(s), H18(m), H19(m), 16-CH$_3$(o) |
| 18 | 56.9 | 2.88 | ddd, 5.9, 5.9, 2.1 | $^2J_{H17\beta/C18}$ = 7, $^2J_{H17\alpha/C18}$ = 4, $^3J_{H20/C18}$ = 3.5 | H15(w), H16(m), H17α(w), H17β(m), H19(w), H20(s), 16-CH$_3$(w), 20-CH$_3$(m) |
| 19 | 61.9 | 3.02 | dd, 8.1, 2.1 | $^3J_{H17\beta/C19}$ = 6, $^3J_{H17\alpha/C19}$ = 2.5, $^2J_{H20/C19}$ = 7.5, $^3J_{H21/C19}$ = 3.5 | H15(n), H16(n), H17α(m), H17β(w), H18(w), H20(m), H21(m), 16-CH$_3$(n), 20-CH$_3$(s) |
| 20 | 42.1 | 1.45 | ddq, 8.1, 4.0, 6.8 | $^2J_{H21/C20}$ < 2 | H17α(n), H17β(o), H18(s), H19(m), H21(s), H22a(n), H22b(o), H23 (s), 20-CH$_3$(s) |
| 21 | 73.6 | 3.98 | ddd, 8.3, 4.4, 4.0 | $^3J_{H19/C21}$ < 2, $^2J_{H20/C21}$ < 2 | H18(n), H19(m), H20(s), H22a(m), H22b(s), H23(s), H30(w) |

TABLE 2-continued

| position | $\delta_C$ | $\delta_H$ | $J_{HH}$ multiplicity, J = Hz | long range $J_{CH}$, J = Hz | NOESY* |
|---|---|---|---|---|---|
| 22a | 28.6 | 1.75 | m | $^2J_{H21/C22} < 2$ | H19(n), H20(o), H21(m), H22b(o), H23(s), 20-CH$_3$(m) |
| 22b | | 1.68 | m | | H19(n), H20(o), H21(s), H22a(o), H23(s), H30(m) |
| 23 | 11 | 1.08 | t, 7.3 | — | H20(s), H21(s), H22a(s), H22(s), 20-CH$_3$(o) |

TABLE 3

| position | $\delta_C$ | $\delta_H$ | $J_{HH}$ multiplicity, J = Hz | long range $J_{CH}$, J = Hz | NOESY* |
|---|---|---|---|---|---|
| 6-CH$_3$ | 24.8 | 1.46 | s | — | H4α(m), H4β(n), H5α(s), H5β(n), H7(m), H8(n), 7-COCH$_3$(o) |
| 7-COCH$_3$ | 170.2 | — | — | — | — |
| 7-COCH$_3$ | 21.1 | 1.96 | s | — | H7(w), H8(n), H9(n), 6-CH$_3$(o) |
| 10-CH$_3$ | 16.6 | 0.87 | d, 6.8 | $^3J_{H9/C10\text{-}Me} < 2$, $^3J_{H11/C10\text{-}Me} < 2$ | H8(n), H9(m), H10(s), H11(s), H13(w), 12-CH$_3$(w) |
| 12-CH$_3$ | 12 | 1.8 | brs | $^3J_{H11/C12\text{-}Me} = 4.5$, $^3J_{H13/C12\text{-}Me} = 7.5$ | H10(s), H11(w), H13(w), H14(s), H15(n), H27(w) |
| 16-CH$_3$ | 21.2 | 1.09 | d, 6.8 | — | H14(m), H15(m), H16(s), H17α(w), H17β(o), H18(w) |
| 20-CH$_3$ | 10.8 | 1.15 | d, 6.8 | — | H18(m), H19(s), H20(s), H21(w), H22a(m), H22b(m), | recorded in pyridine-d5, 30° C., C$_5$D$_4$HN(H3) = 7.22 ppm, C$_5$D$_5$N(C3) = 123.9 ppm
*s: strong; m: moderate; w: weak; n: not detected; o: obscured by overlapping signals Test Example 2

MTPA Esterification of Pladienolide B

To a pyridine (3.0 ml) solution of pladienolide B (8 mg, 14.9 μmol), 4-dimethylaminopyridine (1 mg, 8.1 μmol) and (S)-MTPA chloride (25 mg, 99.2 μmol) were added and after allowed to stand still at room temperature for 12 hours, pyridine was evaporated and then water (10 ml) was added and the mixture was extracted with ethyl acetate (10 ml). The obtained organic layer was concentrated and then purified by preparative HPLC (J 'sphere ODS M-80, 20 mm I.D.×250 mm, acetonitrile: 0.15% trifluoroacetic acid aqueous solution=80:20→100:0, 9.0 ml/min) and rough MTPA ester fraction was concentrated to 1.5 ml. The concentrated fraction was purified by preparative HPLC (J 'sphere ODS M-80, 20 mm I.D.×250 mm, acetonitrile: water=60:40→100:0, 10.0 ml/min) and 3,21-di-(R)-MTPA ester (12.0 mg, 14.0 μmol, 94.0%) of pladienolide B was obtained.

In the same way, to a pyridine (3.0 ml) solution of pladienolide B (8 mg, 14.9 μmol), 4-dimethylaminopyridine (1 mg, 8.1 μmol) and (R)-MTPA chloride (25 mg, 99.2 μmol) were added and after allowed to stand still at room temperature for 12 hours, pyridine was evaporated and then water (10 ml) was added and the mixture was extracted with ethyl acetate (10 ml). The obtained organic layer was concentrated and then purified by preparative HPLC (J 'sphere ODS M-80, 20 mm I.D.×250 mm, acetonitrile: 0.15% trifluoroacetic acid aqueous solution=80:20→100:0, 9.0 ml/min) and rough MTPA ester fraction was concentrated to 1.5 ml. The concentrated fraction was purified by preparative HPLC (J 'sphere ODS M-80, 20 mm I.D.×250 mm, acetonitrile: water=60: 40→100:0, 10.0 ml/min) and 3,21-di-(S)-MTPA ester (10.0 mg, 11.6 μmol, 82.9%) of pladienolide B was obtained.

Test Example 3

Determination of Absolute Configuration of Pladienolide B by Modified Mosher's Method

[Method]

NMR measurement of 3,21-di-(R)-MTPA ester and 3,21-di-(S)-MTPA ester of pladienolide B was performed under the following conditions.

Device used: JNMα 600 MHz (product of JEOL)

Solvent: deuterated chloroform

Measurement temperature: 30° C.

Sample density: about 5 mg/mL

Measuring method: $^1$H-NMR, COSY

[Results]

Assignment information of $^1$H-NMR signals shown in the following Table 4 for 3,21-di-(R)-MTPA ester and 3,21-di-(S)-MTPA ester of pladienolide B was obtained. As a result of having analyzed Δδ value ($\delta_S - \delta_R$) of each proton signal obtained from these chemical shifts, the absolute configuration of 3-position asymmetric carbon was determined to be R configuration, and the absolute configuration of 21-position asymmetric carbon was determined to be S configuration. From the above results and the results of the relative configuration determined by Test Example 1, the absolute configuration of ten asymmetric carbons present in pladienolide B was determined to be (3R,6R,7S,10S, 11S,16S,18R,19R, 20R,21S).

[Formula 44]

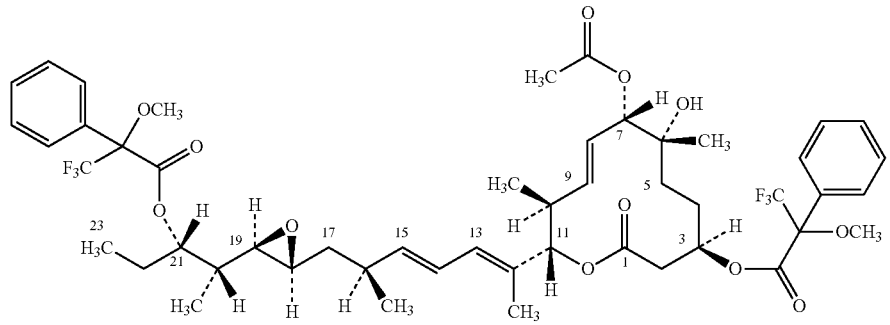

TABLE 4

| position | S-MTPA ester ($\delta_H$) | R-MTPA ester ($\delta_H$) | Δ δ (S − R) |
|---|---|---|---|
| 2α | 2.64 | 2.68 | −0.04 |
| 2β | 2.68 | 2.8 | −0.12 |
| 3 | 5.12 | 5.08 | 0.04 |
| 4α | 1.71 | 1.64 | 0.07 |
| 4β | 1.54 | 1.5 | 0.04 |
| 5α | 1.7 | 1.46 | 0.24 |
| 5β | 1.7 | 1.7 | ±0.00 |
| 7 | 5.08 | 5.04 | 0.04 |
| 8 | 5.65 | 5.63 | 0.02 |
| 9 | 5.69 | 5.68 | 0.01 |
| 10 | 2.52 | 2.52 | ±0.00 |
| 11 | 5.05 | 5.06 | −0.01 |
| 13 | 6.04 | 6.05 | −0.01 |
| 14 | 6.22 | 6.22 | ±0.00 |
| 15 | 5.58 | 5.56 | 0.02 |
| 16 | 2.43 | 2.41 | 0.02 |
| 17α | 1.46 | 1.4 | 0.06 |
| 17β | 1.53 | 1.5 | 0.03 |
| 18 | 2.66 | 2.63 | 0.03 |
| 19 | 2.41 | 2.27 | 0.14 |
| 20 | 1.54 | 1.48 | 0.06 |
| 21 | 5.12 | 5.17 | −0.05 |
| 22α | 1.75 | 1.8 | −0.05 |
| 22β | 1.66 | 1.7 | −0.04 |
| 23 | 0.83 | 0.91 | −0.08 |
| 6-CH₃ | 1.22 | 1.17 | 0.05 |
| 7-COCH₃ | 2.1 | 2.08 | 0.02 |
| 10-CH₃ | 0.87 | 0.86 | 0.01 |
| 12-CH₃ | 1.71 | 1.72 | −0.01 |
| 16-CH₃ | 1.06 | 1.06 | ±0.00 |
| 20-CH₃ | 0.89 | 0.83 | 0.06 | recorded in chloroform-d, 30° C., CHCl₃ = 7.27 ppm

Determination of Absolute Configuration of Pladienolide D

Test Example 4

Determination of Relative Configuration of Pladienolide D by NMR

[Method]

NMR information ($^1$H-$^1$H coupling constant and NOE correlation) which was necessary for determining relative configuration was obtained under the following conditions.

Device used: AVANCE 600 MHz (product of Bruker)

Solvent: deuterated pyridine

Measurement temperature: 30° C.

Sample density: about 20 mg/mL

Measuring method: $^1$H-NMR, $^{13}$C-NMR, COSY, NOESY, HMQC, HMBC

[Results]

NMR information shown in the following Table 5 to Table 6 was obtained. The obtained $^1$H-1H coupling constant and NOE correlation pattern were similar to those of pladienolide B and therefore relative configuration of pladienolide D was determined to be (3R*,6R*,7S*,10S*,11S*,16R*,18R*, 19R*, 20R*, 21S*).

[Formula 44]

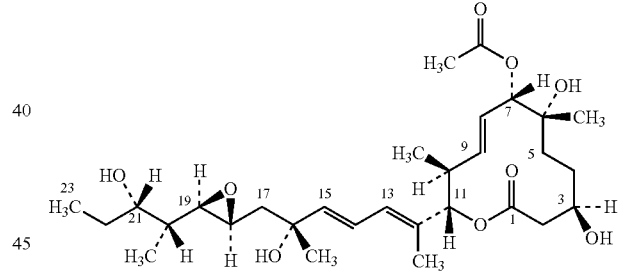

TABLE 5

| position | $\delta_C$ | $\delta_H$ | $J_{HH}$ multiplicity, J = Hz | NOESY* |
|---|---|---|---|---|
| 1 | 171.3 | — | — | — |
| 2α | 40.6 | 2.7 | dd, 14.0, 3.2 | H2β(s), H3(m), H4α(n), H4β(n), H5α(n), H5β(w), |
| 2β | | 2.77 | dd, 14.0, 4.2 | H2α(s), H3(n), H4α(n), H4β(n), H5α(n), H5β(n), |
| 3 | 70.2 | 4.09 | m | H2α(m), H2β(n), H4α(w), H4β(n), H5α(w), H5β(n) |
| 4α | 31.2 | 1.94 | m | H2α(n), H2β(n), H3(w), H4β(s), H5α(w), H5β(o), H7(n), H8(n), H9(n), 6-CH₃(m) |
| 4β | | 1.8 | m | H2α(n), H2β(n), H3(o), H4α(s), H5α(o), H5β(w), H7(s), H8(n), H9(w), 6-CH₃(n) |
| 5α | 38.1 | 1.71 | m | H2α(n), H2β(n), H3(w), H4α(w), H4β(o), H5β(s), H7(n), H8(n), H9(n), 6-CH₃(m) |

TABLE 5-continued

| position | $\delta_C$ | $\delta_H$ | $J_{HH}$ multiplicity, J = Hz | NOESY* |
|---|---|---|---|---|
| 5α | | 2.1 | ddd, 13.5, 13.5, 3.3 | H2α(w), H2β(n), H3(n), H4α(o), H4β(w), H5β(s), H7(n), H8(w), H9(n), 6-CH₃(n) |
| 6 | 73.4 | — | — | — |
| 7 | 80.2 | 5.53 | d, 9.8 | H4α(n), H4β(s), H5α(n), H5β(n), H8(w), H9(n), H10(n), H11(n), 6-CH₃(m), 7-COCH₃(n), 10-CH₃(n) |
| 8 | 127.8 | 6.27 | dd, 15.2, 9.8 | H4α(n), H4β(n), H5α(n), H5β(w), H7(w), H9(w), H10(n), H11(n), 6-CH₃(n), 7-COCH₃(n), 10-CH₃(n) |
| 9 | 140.5 | 5.82 | dd, 15.2, 10.0 | H4α(n), H4β(w), H5α(n), H5β(n), H7(n), H8(w), H10(n), H11(n), 6-CH₃(n), 7-COCH₃(n), 10-CH₃(m) |
| 10 | 41.3 | 2.67 | ddq, 10.7, 10.0, 6.7 | H7(n), H8(w), H9(n), H11(w), 6-CH₃(n), 7-COCH₃(n), 10-CH₃(s), 12-CH₃(s) |
| 11 | 83.3 | 5.35 | d, 10.7 | H2α(n), H2β(n), H7(n), H8(n), H9(n), H10(n), H13(w), 10-CH₃(s), 12-CH₃(w) |
| 12 | 133.3 | — | — | — |

TABLE 6

| position | $\delta_C$ | $\delta_H$ | $J_{HH}$ multiplicity, J = Hz | NOESY* |
|---|---|---|---|---|
| 13 | 131.4 | 6.45 | brd, 11.1 | H10(n), H11(w), H14(m), H15(n), 10-CH₃(w), 12-CH₃(w) |
| 14 | 123.1 | 6.99 | dd, 15.2, 11.1 | H11(n), H13(m), H15(m), 12-CH₃(s), 16-CH₃(m), |
| 15 | 144.5 | 6.16 | d, 15.2 | H13(n), H14(m), H17α(n), H17β(n), H18(w), 12-CH₃(n), 16-CH₃(m) |
| 16 | 72.3 | — | | |
| 17α | 46.5 | 1.96 | dd, 13.8, 6.5 | H15(n), H17β(s), H18(w), H19(m), 16-CH₃(m) |
| 17β | | 2.25 | dd, 13.8, 5.2 | H15(n), H17α(s), H18(m), H19(m), 16-CH₃(m) |
| 18 | 55.3 | 3.38 | ddd, 6.5, 5.2, 2.0 | H15(w), H17α(w), H17β(m), H19(w), H20(s), 16-CH₃(m), 20-CH₃(m) |
| 19 | 62.2 | 3.12 | dd, 7.6, 2.0 | H15(n), H17α(m), H17β(m), H18(w), H20(w), H21(m), 16-CH₃(n), 20-CH₃(s) |
| 20 | 42.3 | 1.58 | m | H17α(n), H17β(o), H18(s), H19(w), H21(s), H22ab(o), H23(s), 20-CH₃(s) |
| 21 | 74.1 | 3.99 | m | H18(n), H19(m), H20(s), H22ab(m), H23(s), 20-CH₃(w) |
| 22ab | 28.9 | 1.80-1.66 | m | H19(n), H20(o), H21(m), H23(s), 20-CH₃(m) |
| 23 | 11.4 | 1.07 | t, 7.4 | H20(s), H21(s), H22ab(s), 20-CH₃(o) |
| 6-CH₃ | 25.2 | 1.46 | s | H4α(m), H4β(n), H5α(m), H5β(n), H7(m), H8(n), 7-COCH₃(o) |
| 7-<u>C</u>OCH₃ | 170.6 | — | — | |
| 7-CO<u>CH₃</u> | 21.5 | 1.96 | s | H7(w), H8(n), H9(n), 6-CH₃(o) |
| 10-CH₃ | 17.1 | 0.87 | d, 6.7 | H8(n), H9(m), H10(s), H11(s), H13(w), 12-CH₃(w) |
| 12-CH₃ | 12.4 | 1.78 | brs | H10(s), H11(w), H13(w), H14(s), H15(n), 10-CH₃(w) |
| 16-CH₃ | 29.7 | 1.63 | s | H14(m), H15(m), H16(s), H17α(m), H17β(m), H18(m) |
| 20-CH₃ | 10.6 | 1.17 | d, 7.0 | H18(m), H19(s), H20(s), H21(w), H22ab(m), H23(o) | recorded in pyridine-d5, 30° C., C₅D₄HN(H3) = 7.22 ppm, C₅D₅N(C3) = 123.9 ppm

*s: strong; m: moderate; w: weak; n: not detected; o: obscured by overlapping signals

Test Example 5

MTPA Esterification of Pladienolide D

A pyridine (262 µl) solution of pladienolide D (5.24 mg, 9.48 µmol) and a dichloromethane solution (2.0 ml) of 4-dimethylaminopyridine (82.2 mg, 0.67 mmol) were prepared. A part (100 µl, 3.62 µmol) of the pyridine solution of pladienolide D was taken and the dichloromethane solution (100 µl, 33.5 µmol) of 4-dimethylaminopyridine and (S)-MTPA chloride (10 mg, 39.7 µmol) were added and after stirred at room temperature for 30 minutes, 4-dimethylaminopyridine solution (100 µl, 33.5 µmol) and (S)-MTPA chloride (10 mg, 39.7 µmol) were further added and stirred at room temperature for 30 minutes. Dichloromethane (2.0 ml) and water (2.0 ml) were added to the reaction mixture and after stirred, the dichloromethane layer was separated and concentrated. The residue was purified by NH-silica gel column chromatography (ethyl acetate/hexane=3:1 mixed solvent), the obtained fraction of MTPA was concentrated by nitrogen gas spraying and then further dried under reduced pressure and 3,21-di-(R)-MTPA ester of pladienolide D was obtained.

In the same way, a part (100 µl, 3.62 µmol) of the pyridine solution of pladienolide D was taken and the dichloromethane solution (100 µl, 33.5 µmol) of 4-dimethylaminopyridine and (R)-MTPA chloride (10 mg, 39.7 µmol) were added and after stirred at room temperature for 30 minutes, 4-dimethylaminopyridine solution (100 µl, 33.5 µmol) and (R)-MTPA chloride (10 mg, 39.7 µmol) were further added and stirred at room temperature for 30 minutes. Dichloromethane (2.0 ml) and water (2.0 ml) were added to the reaction mixture and after stirred, the dichloromethane layer was separated and concentrated. The residue was purified by NH-silica gel column chromatography (ethyl acetate/hexane=3:1 mixed solvent), the obtained fraction of MTPA was concentrated by nitrogen gas spraying and then further dried under reduced pressure and 3,21-di-(S)-MTPA ester of pladienolide D was obtained.

Test Example 6

Determination of Absolute Configuration of Pladienolide D by Modified Mosher's Method

[Method]

NMR measurement of 3,21-di-(R)-MTPA ester and 3,21-di-(S)-MTPA ester of pladienolide D was performed under the following conditions.

Device used: INOVA 500 MHz (product of Varian)

Solvent: deuterated acetonitrile

Measurement temperature: 30° C.

Measuring method: $^1$H-NMR, COSY, TOCSY, ROESY

[Results]

Assignment information of $^1$H-NMR signals shown in the following Table 7 for 3,21-di-(R)-MTPA ester and 3,21-di-(S)-MTPA ester of pladienolide D was obtained. As a result of having analyzed $\Delta\delta$ value ($\delta_S - \delta_R$) of each proton signal obtained from these chemical shifts, the absolute configuration of 3-position asymmetric carbon was determined to be R configuration, and the absolute configuration of 21-position asymmetric carbon was determined to be S configuration. From the above results and the results of the relative configuration determined by Test Example 4, the absolute configuration of ten asymmetric carbons present in pladienolide D was determined to be (3R,6R,7S,10S, 11S,16R,18R,19R, 20R,21S).

[Formula 46]

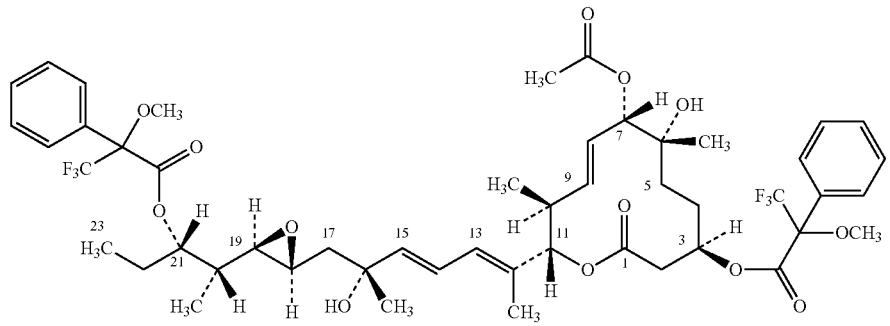

TABLE 7

| position | S-MTPA ester ($\delta_H$) | R-MTPA ester ($\delta_H$) | $\Delta \delta$ (S − R) |
|---|---|---|---|
| $2_\alpha$ | 2.61 | 2.7 | −0.09 |
| $2_\beta$ | 2.67 | 2.71 | −0.04 |
| 3 | 5.12 | 5.14 | −0.02 |
| $4_\alpha$ | 1.54 | 1.49 | 0.05 |
| $4_\beta$ | 1.66 | 1.49 | 0.17 |
| $5_\alpha$ | 1.42 | 1.38 | 0.04 |
| $5_\beta$ | 1.61 | 1.59 | 0.02 |
| 7 | 4.99 | 4.93 | 0.06 |
| 8 | 5.67 | 5.67 | ±0.00 |
| 9 | 5.52 | 5.51 | 0.01 |
| 10 | 2.57 | 2.57 | ±0.00 |
| 11 | 4.91 | 4.94 | −0.03 |
| 13 | 6.03 | 6.02 | 0.01 |
| 14 | 6.45 | 6.42 | 0.03 |
| 15 | 5.81 | 5.73 | 0.08 |
| $17_\alpha$ | 1.57 | 1.45 | 0.12 |
| $17_\beta$ | 1.78 | 1.75 | 0.03 |
| 18 | 2.83 | 2.77 | 0.06 |
| 19 | 2.41 | 2.14 | 0.27 |
| 20 | 1.52 | 1.4 | 0.12 |
| 21 | 5.08 | 5.11 | −0.03 |
| 22 | 1.65 | 1.69 | −0.04 |
| 23 | 0.77 | 0.88 | −0.11 |
| 6-CH$_3$ | 1.14 | 1.1 | 0.04 |
| 7-COCH$_3$ | 2.02 | 2.01 | 0.01 |

TABLE 7-continued

| position | S-MTPA ester ($\delta_H$) | R-MTPA ester ($\delta_H$) | Δ δ (S − R) |
|---|---|---|---|
| 10-CH$_3$ | 0.8 | 0.8 | ±0.00 |
| 12-CH$_3$ | 1.72 | 1.72 | ±0.00 |
| 16-CH$_3$ | 1.27 | 1.24 | 0.03 |
| 20-CH$_3$ | 0.87 | 0.76 | 0.11 | recorded in acetonitrile-d3, 30° C., CHD$_2$CN = 1.93 ppm

Total Synthesis of Pladienolide B

Step 1

Synthesis of (4Z)-6-[(4-methoxybenzyl)oxy]-4-methylhex-4-enal]

[Formula 47]

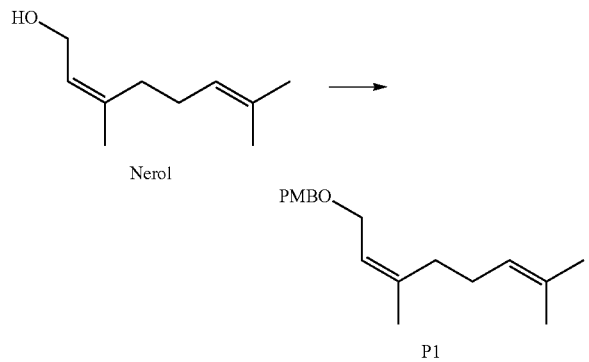

(1) Synthesis of 1-({[(2Z)-3,7-dimethylocta-2,6-dien-1-yl]oxy}methyl)-4-methoxybenzene (P1)

Nerol (150 g, 972 mmol) was added dropwise to a DMF (1.50 l) suspension of sodium hydride (60%, 38.9 g, 973 mmol) under nitrogen gas stream at room temperature. The reaction solution was stirred at room temperature for one hour and then cooled to 0° C. After tetra-n-butyl ammonium iodide (35.9 g, 97.2 mmol) was added to the reaction solution, 4-methoxybenzyl chloride (148 g, 926 mmol) was added dropwise. The reaction solution was stirred at 0° C. for one hour and then at room temperature for six hours. Water was added to the reaction solution, which was then extracted with n-heptane. After the obtained organic layer was washed with water and brine (saturated solution of sodium chloride) sequentially, it was dried over anhydrous magnesium sulfate. After the drying agent was filtered off, the organic layer was concentrated under reduced pressure. The residue was purified by silica gel column chromatography (Kanto Chemical, commercial name Silica gel 60N, granular, neutral, 0.040 mm-0.100 mm; n-heptane:ethyl acetate=1:0→30:1→25:1) to obtain the title compound (246.7 g) as a colorless oil.

400 MHz $^1$H-NMR (CDCl$_3$) δ (ppm) 1.58 (s, 3H), 1.67 (s, 3H), 1.75 (d, J=1.2 Hz, 3H), 2.00-2.12 (m, 4H), 3.80 (s, 3H), 3.97 (dd, J=1.0, 7.0 Hz, 1H), 4.43 (s, 2H), 5.04-5.12 (m, 1H), 5.40 (dt, J=1.2, 6.8 Hz, 2H), 6.85-6.89 (m, 2H), 7.25-7.28 (m, 2H); 100 MHz $^{13}$C-NMR (CDCl$_3$) δ (ppm) 17, 49, 23.36, 25.56, 26.59, 32.13, 55.06, 65.96, 71.62, 113.59, 121.82, 123.79, 129.24, 130.55, 131.69, 140.31, 159.00; IR (neat) 2964, 2913, 2855, 1612, 1512, 1247, 1093, 1067, 1037, 819 cm$^{-1}$; HRMS C$_{18}$H$_{27}$O$_2$ (M+H$^+$) Calcd: 275.2011, Found: 275.2003.

[Formula 48]

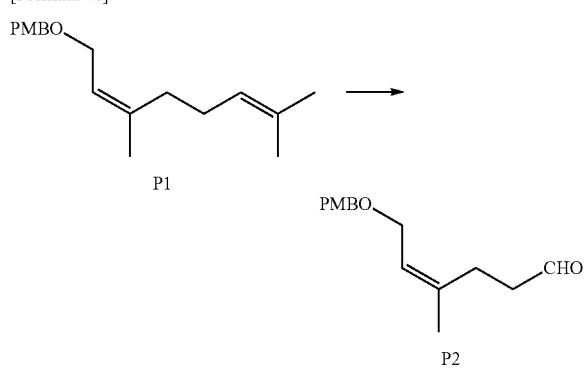

(2) Synthesis of (4Z)-6-[(4-methoxybenzyl)oxy]-4-methylhex-4-enal (P2)

1-({[(2Z)-3,7-dimethylocta-2,6-dien-1-yl]oxy}methyl)-4-methoxybenzene (75.0 g, 273 mmol) was dissolved in dichloromethane (1.13 l) and pyridine (11.3 ml). This reaction solution was cooled to −78° C., to which ozone was bubbled (flow rate 2 l/min, electric voltage 90 V) for 170 minutes with stirring. After addition of dimethylsulfide (80.3 ml, 1.09 mol), the reaction solution was allowed to warm to room temperature and was stirred overnight. The reaction solution was concentrated under reduced pressure and the obtained residue was purified by silica gel column chromatography (Kanto Chemical, commercial name Silica gel 60N, granular, neutral, 0.040 mm-0.100 mm; n-heptane:ethyl acetate=4:1) and the title compound (36.9 g) was obtained as a colorless oil while 1-({[(2Z)-3,7-dimethylocta-2,6-dien-1-yl]oxy}methyl)-4-methoxybenzene (14.1 g) was recovered.

400 MHz $^1$H-NMR (CDCl$_3$) δ (ppm) 1.75 (s, 3H), 2.36 (t, J=7.6 Hz, 2H), 2.47-2.55 (m, 2H), 3.81 (s, 3H), 3.98 (d, J=6.7 Hz, 2H), 4.43 (s, 2H), 5.46 (brt, J=6.7 Hz, 1H), 6.86-6.90 (m, 2H), 7.25-7.27 (m, 2H), 9.75 (t, J=1.2 Hz, 1H); 100 MHz $^{13}$C-NMR (CDCl$_3$) δ (ppm) 22.99, 24.34, 42.11, 55.09, 65.61, 71.82, 113.62, 122.97, 129.29, 130.25, 138.43, 159.04, 201.63; IR (neat) 2935, 2835, 2727, 1722, 1612, 1514, 1249, 1072, 1035, 819 cm$^{-1}$; HRMS C$_{15}$H$_{20}$NaO$_3$ (M+Na$^+$) Calcd: 271.1310, Found: 271.1322

Step 2

Synthesis of methyl (3R,6Z)-3-{[tert-butyl(dimethyl)silyl]oxy-8-[(4-methoxybenzyl)oxy]-6-methyloct-6-enoate

[Formula 49]

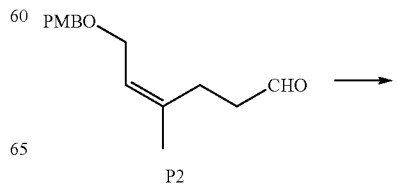

-continued

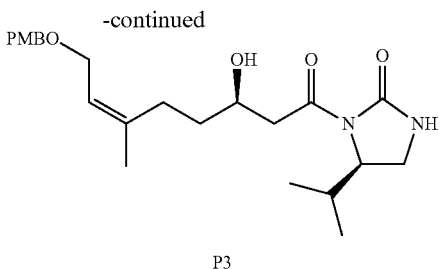

P3

(1) Synthesis of (4R)-3-{(3R,6Z)-3-hydroxy-8-[(4-methoxybenzyl)oxy-6-methyloct-6-enoyl]-4-isopropyl-1,3-oxazolidin-2-one (P3)

This step was performed with reference to the literature (Fukuzawa, S.; Matsuzawa, H.; Yoshimitsu, S.; J. Org. Chem., 2000, 65(6), 1702-1706.). (R)—N-bromoacetyl-4-isopropyl-2-oxazolidinone used in this step was also prepared by the method described in this literature.

Anhydrous THF distilled by using lithium aluminum hydride immediately before use was used in this step.

After diiodomethane (1.20 ml, 14.9 mmol) was added to an anhydrous THF (200 ml) suspension of samarium powder (45.0 g, 299 mmol) at room temperature under nitrogen atmosphere, an anhydrous THF (700 ml) solution of diiodomethane (21.0 ml, 261 mmol) was added dropwise over 100 minutes. After the addition was completed, the reaction solution was stirred at room temperature for two hours and cooled to −78° C. An anhydrous THF (280 ml) solution of (4Z)-6-[(4-methoxybenzyl)oxy]-4-methylhexa-4-enal (28.4 g, 115 mmol) and (R)—N-bromoacetyl-4-isopropyl-2-oxazolidinone (30.1 g, 120 mmol) was added dropwise to the reaction solution at such a rate that the reaction solution temperature was kept below −72° C. After the reaction solution was stirred at −78° C. for one hour, it was warmed to room temperature. 0.5N hydrochloric acid (300 ml) to the reaction solution was added to terminate the reaction. After addition of 0.5N hydrochloric acid (700 ml), the reaction solution was extracted with ethyl acetate. After the obtained organic layer was washed with 5% sodium sulfite aqueous solution, water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate) to obtain the title compound (43.4 g, >98% de) as a yellow oil. Here, the optical purity was determined by HPLC using (DAICEL, commercial name CHIRALCEL OD; n-hexane:isopropylalcohol=4:1).

400 MHz $^1$H-NMR (CDCl$_3$) δ (ppm) 0.87 (d, J=7.2 Hz, 3H), 0.92 (d, J=7.2 Hz, 3H), 1.56-1.64 (m, 2H), 1.76 (s, 3H), 2.08-2.18 (m, 1H), 2.30-2.40 (m, 2H), 2.98 (dd, J=9.2, 16.9 Hz, 1H), 3.13 (dd, J=2.9, 16.9 Hz, 1H), 3.26 (d, J=4.4 Hz, 1H), 3.80 (s, 3H), 3.93 (dd, J=7.2, 10.8 Hz, 1H), 4.01-4.08 (m, 2H), 4.21 (dd, J=3.2, 9.2 Hz, 1H), 4.27 (t, J=9.2 Hz, 1H), 4.40-4.49 (m, 1H), 4.44 (s, 2H), 5.46 (brt, J=6.6 Hz, 1H), 6.86-6.89 (m, 2H), 7.26-7.29 (m, 2H); 100 MHz $^{13}$C-NMR (CDCl$_3$) δ (ppm) 14.55, 17.79, 23.09, 27.73, 28.34, 34.38, 42.58, 55.10, 58.25, 63.37, 65.59, 66.76, 71.75, 113.59, 122.02, 129.39, 130.26, 140.64, 153.95, 159.01, 172.18; IR (neat) 3455, 2963, 1781, 1699, 1514, 1388, 1303, 1248, 1207, 1061, 1034 cm$^{-1}$; HRMS C$_{23}$H$_{34}$N$_2$NaO$_5$ (M+Na$^+$) Calcd: 442.2206, Found: 442.2197; [α]$_D^{22}$ −60.2 (c 1.06, CHCl$_3$)

[Formula 50]

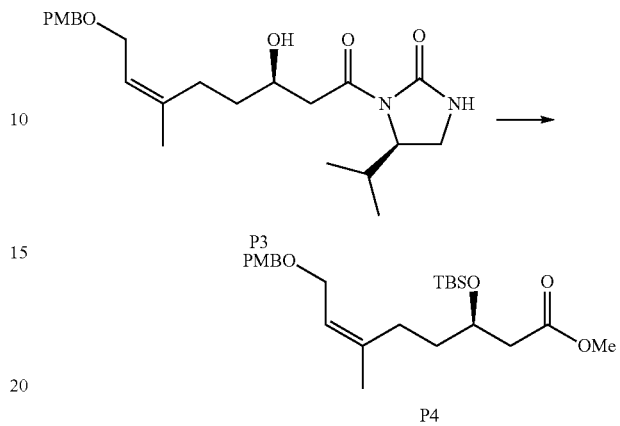

(2) Synthesis of methyl (3R,6Z)-3-{[tert-butyl(dimethyl)silyl]oxy}-8-[(4-methoxybenzyl)oxy]-6-methyloct-6-enoate (P4)

To a THF (175 ml) solution of (4R)-3-{(3R,6Z)-3-hydroxy-8-[(4-methoxybenzyl)oxy]-6-methyloct-6-enoyl}-4-isopropyl-1,3-oxazolidin-2-one (14.6 g, 34.8 mmol), a water (43.0 ml) solution of anhydrous lithium hydroxide (2.50 g, 104 mmol) and 30% hydrogen peroxide solution (11.8 ml) was added at 0° C. The reaction solution was stirred at room temperature for 13 hours. A water (20.0 ml) solution of anhydrous lithium hydroxide (3.75 g, 156 mmol) and 30% hydrogen peroxide solution (17.7 ml) was further added to the reaction solution and the reaction solution was stirred for two hours. After sodium sulfite (21.0 g, 165 mmol) was added to the reaction solution at 0° C., it was stirred at room temperature for five minutes. Water was added to the reaction solution and washed with chloroform. 2N hydrochloric acid was added to the water layer to acidify, which was then extracted with ethyl acetate. The organic layer was washed with water and brine sequentially and then dried over anhydrous magnesium sulfate. After the drying agent was filtered off, the organic layer was concentrated under reduced pressure.

The obtained residue was dissolved in a mixed solvent of THF (220 ml)-methanol (22.0 ml) and cooled to 0° C. and 2M n-hexane solution of trimethylsilyldiazomethane (22.6 ml, 45.1 mmol) was added under stirring. After the reaction solution was stirred at 0° C. for 40 minutes, it was stirred at room temperature for 30 minutes. After acetic acid (1.00 ml) was added to the reaction solution and stirred at room temperature for 30 minutes, the reaction solution was concentrated under reduced pressure.

The obtained residue was dissolved in DMF (80.0 ml), followed by addition of imidazole (7.09 g, 104 mmol) and tert-butyldimethylsilyl chloride (7.85 g, 52.1 mmol), and the mixture was stirred at room temperature for 14 hours. The reaction solution was poured into water, which was then extracted with ethyl acetate. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=6:1) to obtain the title compound (12.9 g) as a colorless oil.

400 MHz $^1$H-NMR (CDCl$_3$) δ (ppm) 0.03 (s, 3H), 0.06 (s, 3H), 0.87 (s, 9H), 1.51-1.58 (m, 2H), 1.74 (brs, 3H), 1.96-2.05 (m, 1H), 2.08-2.18 (m, 1H), 2.39 (dd, J=5.6, 14.1 Hz, 1H), 2.46 (dd, J=7.2, 14.4 Hz, 1H), 3.66 (s, 3H), 3.80 (s, 3H), 3.96 (d, J=6.8 Hz, 2H), 4.08-4.16 (m, 1H), 4.42 (s, 2H), 5.39 (brt, J=6.8 Hz, 1H), 6.86-6.89 (m, 2H), 7.24-7.28 (m, 2H); 100 MHz $^{13}$C-NMR (CDCl$_3$) δ (ppm) −4.95, −4.63, 17.85, 23.38, 25.65, 27.50, 35.97, 42.11, 51.36, 55.10, 65.85, 69.22, 71.77, 113.65, 121.78, 129.31, 130.45, 140.24, 159.06, 171.94; IR (neat) 2952, 2930, 2856, 1740, 1514, 1250, 1083, 1038, 836, 776 cm$^{-1}$; HRMS C$_{24}$H$_{41}$O$_5$Si (M+H$^+$) Calcd: 437.2723, Found: 437.2731; [α]$_D^{22}$−11.1 (c 1.04, CHCl$_3$)

Step 3

Synthesis of methyl 6,7-O-benzylidene-3-O-[tert-butyl(dimethyl)silyl]-2,4,5-trideoxy-6-C-methyl-L-arabino-octonate

[Formula 51]

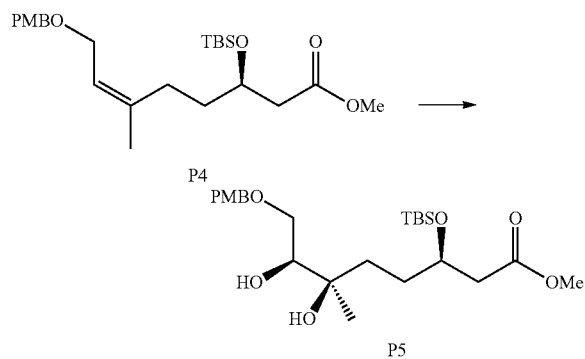

(1) Synthesis of methyl 3-O-[tert-butyl (dimethyl) silyl]-2,4,5-trideoxy-8-O-(4-methoxybenzyl)-6-C-methyl-L-arabino-octonate (P5)

To a mixed solution of tert-butyl alcohol (700 ml)-water (700 ml), AD-mix α (181 g) and methanesulfonamide (12.4 g, 130 mmol) were added at 0° C. and the reaction solution was stirred at 0° C. for 30 minutes. A mixed solution of tert-butyl alcohol (150 ml)-water (150 ml) of methyl (3R,6Z)-3-{[tert-butyl(dimethyl)silyl]oxy-}-8-[(4-methoxybenzyl)oxy]-6-methyloct-6-enoate (56.8 g, 130 mmol) was added to the reaction solution and stirred at 0° C. for 11 hours. Sodium sulfite (197 g, 1.56 mol) was added to the reaction solution and stirred at room temperature. After the reaction solution was diluted with water, it was extracted with ethyl acetate. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; heptane:ethyl acetate=3:1) to obtain the title compound (56.3 g, 76% de) as a colorless oil. The optical purity was determined by HPLC using a chiral column (DAICEL, commercial name CHIRALCEL OD; n-hexane:isopropylalcohol=95:5).

400 MHz $^1$H-NMR (CDCl$_3$) (data of the main product) δ (ppm) 0.04 (s, 3H), 0.06 (s, 3H), 0.86 (s, 9H), 1.17 (s, 3H), 1.24-1.40 (m, 1H), 1.46-1.68 (m, 3H), 2.39 (dd, J=5.6, 14.8 Hz, 1H), 2.45 (dd, J=6.8, 14.8 Hz, 1H), 2.66 (s, 1H), 2.73 (d, J=4.8 Hz, 1H), 3.54-3.66 (m, 3H), 3.66 (s, 3H), 3.81 (s, 3H), 4.09-4.18 (m, 1H), 4.46 (d, J=11.2 Hz, 1H), 4.50 (d, J=11.2 Hz, 1H), 6.87-6.91 (m, 2H), 7.23-7.27 (m, 2H); 100 MHz $^{13}$C-NMR (CDCl$_3$) δ (ppm)−4.99, −4.57, 17.85, 23.03, 25.66, 30.94, 32.86, 42.00, 51.40, 55.14, 69.40, 70.81, 73.24, 73.39, 74.78, 113.81, 129.41, 129.50, 159.32, 172.02; IR (neat) 3481, 2953, 2931, 1739, 1514, 1251, 1173, 1084, 1038, 835, 777 cm$^{-1}$; HRMS C$_{24}$H$_{42}$NaO$_7$Si (M+Na$^+$) Calcd: 493.2598, Found: 493.2556; [α]$_D^{22}$−18.5 (c 2.22, CHCl$_3$)

[Formula 52]

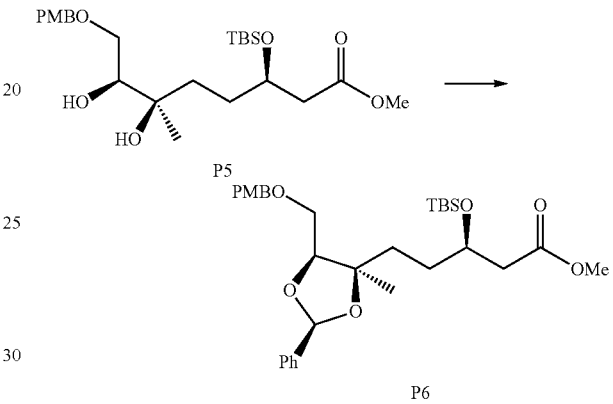

(2) Synthesis of methyl 6,7-O-benzylidene-3-O-[tert-butyl(dimethyl)silyl]-2,4,5-trideoxy-8-O-(4-methoxybenzyl)-6-C-methyl-L-arabino-octonate (P6)

To an anhydrous dichloromethane (90 ml) solution of methyl 3-O-[tert-butyl(dimethyl)silyl]-2,4,5-trideoxy-8-O-(4-methoxybenzyl)-6-C-methyl-L-arabino-octonate (5.00 g, 10.6 mmol), benzaldehyde dimethylacetal (9.55 ml, 63.6 mmol) and pyridinium p-toluene sulfonate (133 mg, 0.53 mmol) were added. The reaction solution was stirred at room temperature for 23 hours. The reaction solution was poured into a saturated sodium hydrogen carbonate aqueous solution, which was then extracted with dichloromethane. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; heptane:ethyl acetate=5:1→2:1) to obtain the title compound (5.92 g) as a colorless oil.

400 MHz $^1$H-NMR (CDCl$_3$) (data of the main product) δ (ppm) 0.00 (s, 3H), 0.01 (s, 3H), 0.85 (s, 9H), 1.19-1.38 (m, 1H), 1.35 (s, 3H), 1.56-1.73 (m, 3H), 2.30 (dd, J=5.2, 14.5 Hz, 1H), 2.40 (dd, J=7.7, 14.5 Hz, 1H), 3.58 (dd, J=5.0, 9.9 Hz, 1H), 3.64 (s, 3H), 3.68 (dd, J=7.1, 9.9 Hz, 1H), 3.81 (s, 3H), 4.06 (dd, J=5.0, 7.1 Hz, 1H), 4.07-4.13 (m, 1H), 4.46 (d, J=11.4 Hz, 1H), 4.56 (d, J=11.4 Hz, 1H), 5.88 (s, 1H), 6.86-6.90 (m, 2H), 7.25-7.28 (m, 2H), 7.33-7.37 (m, 3H), 7.43-7.47 (m, 2H); 100 MHz $^{13}$C-NMR (CDCl$_3$) δ (ppm) −5.04, −4.61, 17.84, 22.73, 25.65, 30.53, 31.18, 42.18, 51.34, 55.13, 67.74, 69.47, 73.17, 81.23, 84.81, 102.27, 113.74, 126.60, 128.14, 129.02, 129.38, 129.71, 137.84, 159.23, 172.03; IR (neat) 2953, 2930, 2857, 1739, 1514, 1250, 1092, 835, 776 cm$^{-1}$; HRMS C$_{31}$H$_{46}$NaO$_7$Si (M+Na$^+$) Calcd: 581.2911, Found: 581.2905; [α]$_D$$^{22}$+5.5 5 (c 1.35, CHCl$_3$)

[Formula 53]

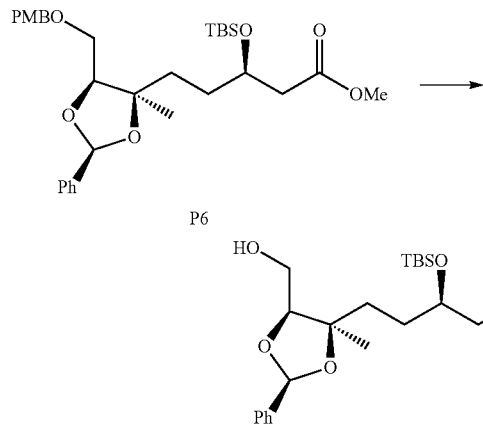

(3) Synthesis of methyl 6,7-O-benzylidene-3-O-[tert-butyl(dimethyl)silyl]-2,4,5-trideoxy-6-C-methyl-L-arabino-octonate (P7)

To a mixed solution of dichloromethane (176 ml)-water (17.6 ml) of methyl 6,7-O-benzylidene-3-O-[tert-butyl(dimethyl)silyl]-2,4,5-trideoxy-8-O-(4-methoxybenzyl)-6-C-methyl-L-arabino-octonate (8.80 g, 15.7 mmol), 2,3-dichloro-5,6-dicyano-1,4-benzoquinone (5.38 g, 23.7 mmol) was added at 0° C. After the reaction solution was stirred at 0° C. for one hour, water (17.6 ml) was added. After the reaction solution was stirred for two hours and a half, 2,3-dichloro-5,6-dicyano-1,4-benzoquinone (2.70 g, 11.9 mmol) was added. The reaction solution was further stirred at 0° C. for three hours. The reaction solution was poured into a sodium hydrogen carbonate aqueous solution, which was then extracted with dichloromethane. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=5:1→4:1→2:1 to obtain the title compound (4.76 g) as a white solid. The title compound (4.44 g) was obtained as a colorless crystal by recrystallization from n-hexane.

400 MHz $^1$H-NMR (CDCl$_3$) δ (ppm) 0.02 (s, 3H), 0.05 (s, 3H), 0.86 (s, 9H), 1.32-1.41 (m, 1H), 1.38 (s, 3H), 1.59-1.82 (m, 3H), 1.88 (dd, J=4.0, 8.4 Hz, 1H), 2.38 (dd, J=5.6, 14.6 Hz, 1H), 2.46 (dd, J=7.2, 14.6 Hz, 1H), 3.65 (s, 3H), 3.73 (dd, J=3.6, 8.4, 11.8 Hz, 1H), 3.84 (ddd, J=4.0, 7.6, 11.8 Hz, 1H), 3.98 (dd, J=3.6, 7.6 Hz, 1H), 4.10-4.18 (m, 1H), 5.91 (s, 1H), 7.36-7.40 (m, 3H), 7.45-7.49 (m, 2H); 100 MHz $^{13}$C-NMR (CDCl$_3$) δ (ppm)-4.94, -4.56, 17.91, 22.66, 25.71, 30.71, 31.38, 42.25, 51.47, 61.42, 69.40, 81.33, 86.38, 102.20, 126.60, 128.36, 129.29, 137.69, 172.07; IR (KBr) 3489, 2951, 2856, 1746, 1087, 1024, 836, 768, 704 cm$^{-1}$; HRMS C$_{23}$H$_{38}$NaO$_6$Si (M+Na$^+$) Calcd: 461.2335, Found: 461.2368; [α]$_D$$^{22}$-4.31 (c 1.21, CHCl$_3$)

Step 4

Synthesis of (3R)-3-{[tert-butyl (dimethyl)silyl]oxy}-5-[(2S,4R,5S)-4-methyl-2-phenyl-5-vinyl-1,3-dioxolan-4-yl]pentanoic acid

[Formula 54]

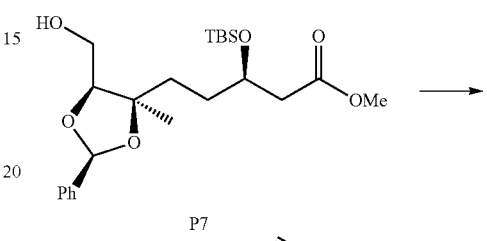

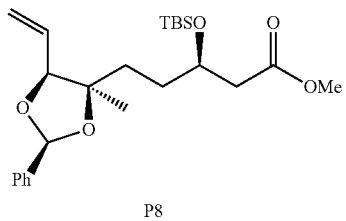

(1) Synthesis of methyl (3R)-3-{[tert-butyl(dimethyl)silyl]oxy}-5-[(2S,4R,5S)-4-methyl-2-phenyl-5-vinyl-1,3-dioxolan-4-yl] pentanoate (P8)

To a dichloromethane (300 ml) solution of methyl 6,7-O-benzylidene-3-O-[tert-butyl(dimethyl)silyl]-2,4,5-trideoxy-6-C-methyl-L-arabino-octonate (10.2 g, 23.3 mmol), Dess-Martin reagent (12.8 g, 30.3 mmol) was added. The reaction solution was stirred at room temperature for one hour. The reaction solution was diluted with ether and washed with a saturated sodium hydrogen carbonate aqueous solution containing sodium sulfite and brine sequentially. The organic layer was dried over anhydrous magnesium sulfate. After the drying agent was filtered off, the organic layer was concentrated under reduced pressure.

The obtained residue was dissolved in anhydrous THF (50.0 ml) and this solution was added dropwise at -15° C. to an anhydrous THF (100 ml) solution of methylenetriphenylphosphorane prepared by a conventional method from methyltriphenylphosphonium iodide (10.4 g, 25.7 mmol) and n-butyllithium (2.59M n-hexane solution 9.94 ml, 25.7 mmol) under nitrogen atmosphere. After the reaction solution was stirred at -15° C. for 20 minutes, it was stirred at room temperature for 30 minutes. The reaction solution was poured into a saturated ammonium chloride aqueous solution, which was then extracted with ethyl acetate. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=19:1→9:1) to obtain the title compound (7.91 g) as a colorless oil.

400 MHz $^1$H-NMR (CDCl$_3$) δ (ppm) 0.00 (s, 3H), 0.02 (s, 3H), 0.85 (s, 9H), 1.25-1.36 (m, 1H), 1.35 (s, 3H), 1.55-1.72 (m, 3H), 2.34 (dd, J=5.4, 14.6 Hz, 1H), 2.42 (dd, J=7.4, 14.6 Hz, 1H), 3.64 (s, 3H), 4.06-4.14 (m, 1H), 4.28 (ddd, J=1.2, 1.2, 6.8 Hz, 1H), 5.31 (ddd, J=1.2, 1.2, 10.6 Hz, 1H), 5.42 (ddd, J=1.2, 1.2, 17.2 Hz, 1H), 5.90 (ddd, J=6.8, 10.6, 17.2 Hz, 1H), 5.92 (s, 1H), 7.35-7.38 (m, 3H), 7.46-7.50 (m, 2H); 100 MHz $^{13}$C-NMR (CDCl$_3$) δ (ppm) −5.05, −4.66, 17.81, 22.36, 25.63, 31.30, 31.93, 42.23, 51.28, 69.50, 82.14, 87.73, 102.12, 118.69, 126.57, 128.15, 128.99, 132.58, 137.90, 171.98; IR (neat) 2954, 2930, 2857, 1740, 1255, 1090, 1065, 1006, 836, 776 cm$^{-1}$; HRMS C$_{24}$H$_{38}$NaO$_5$Si (M+Na$^+$) Calcd: 457.2386, Found: 457.2394; [α]$_D^{22}$−11.5 (c 2.26, CHCl$_3$)

[Formula 55]

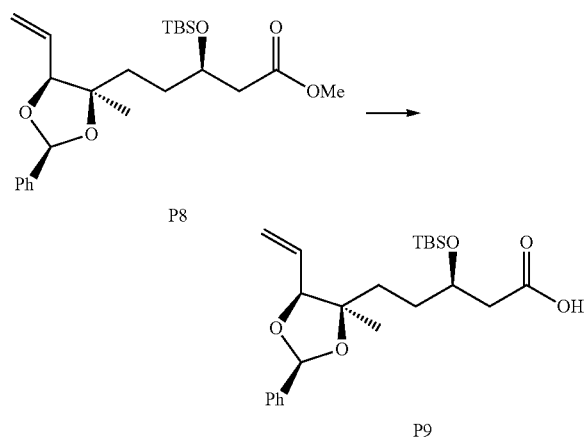

(2) Synthesis of (3R)-3-{[tert-butyl(dimethyl)silyl]oxy}-5-[(2S,4R,5S)-4-methyl-2-phenyl-5-vinyl-1,3-dioxolan-4-yl]pentanoic acid (P9)

Methyl (3R)-3-{[tert-butyl(dimethyl)silyl]oxy}-5-[(2S,4R,5S)-4-methyl-2-phenyl-5-vinyl-1,3-dioxolan-4-yl]pentanoate (14.6 g, 33.6 mmol) was dissolved in a mixed solution of THF (140 ml)-methanol (140 ml)-water (70.0 ml) and anhydrous lithium hydroxide (4.02 g, 168 mmol) was added. The reaction solution was stirred at room temperature for four and a half hours. The reaction solution was poured into 0.5N hydrochloric acid, which was then extracted with ethyl acetate. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=4:1→2:1) to obtain the title compound (14.1 g) as a colorless oil.

400 MHz $^1$H-NMR (CDCl$_3$) δ (ppm) 0.05 (s, 6H), 0.87 (s, 9H), 1.26-1.34 (m, 1H), 1.35 (s, 3H), 1.50-1.68 (m, 2H), 1.73-1.79 (m, 1H), 2.44 (dd, J=5.4, 15.4 Hz, 1H), 2.48 (dd, J=5.4, 15.4 Hz, 1H), 4.00-4.06 (m, 1H), 4.29 (ddd, J=1.2, 1.2, 6.8 Hz, 1H), 5.32 (ddd, J=1.2, 1.2, 10.1 Hz, 1H), 5.44 (ddd, J=1.2, 1.2, 17.2 Hz, 1H), 5.88 (ddd, J=6.8, 10.8, 17.2 Hz, 1H), 5.93 (s, 1H), 7.35-7.38 (m, 3H), 7.47-7.49 (m, 2H); 100 MHz $^{13}$C-NMR (CDCl$_3$) δ (ppm) −5.00, −4.63, 17.88, 22.38, 25.69, 31.18, 32.03, 41.99, 69.40, 82.18, 87.77, 102.17, 118.88, 126.59, 128.25, 129.10, 132.51, 137.90, 177.39; IR (neat) 3036, 2956, 2930, 2886, 2857, 1712, 1254, 1090, 1065, 836, 776 cm$^{-1}$; HRMS C$_{23}$H$_{36}$NaO$_5$Si (M+Na$^+$) Calcd: 443.2230, Found: 443.2212; [α]$_D^{22}$+4.00 (c 1.09, CHCl$_3$)

Step 5

Synthesis of (2E)-4-[(4-methoxybenzyl)oxy]-2-methylbut-2-enal

[Formula 56]

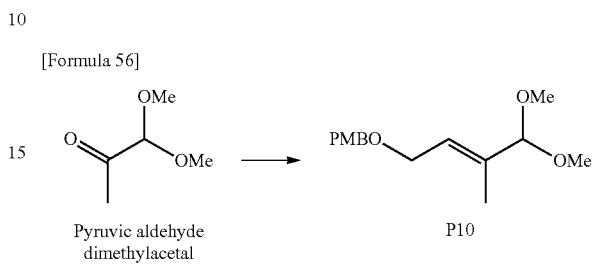

Pyruvic aldehyde
dimethylacetal

P10

(1) Synthesis of 1-({[(2E)-4,4-dimethoxy-3-methylbut-2-en-1-yl]oxy}methyl)-4-methoxybenzene (P10)

Sodium hydride (60%, 407 mg, 10.2 mmol) was added to an anhydrous THF (20.0 ml) solution of triethyl phosphonoacetate (2.28 g, 10.2 mmol) at 0° C. under nitrogen atmosphere. After the reaction solution was stirred at 0° C. for 15 minutes, pyruvaldehyde dimethylacetal (1.00 g, 8.47 mmol) was added. After the reaction solution was stirred at 0° C. for 30 minutes, it was stirred at room temperature for 10 minutes. The reaction solution was poured into water, which was then extracted with n-hexane. After the organic layer was washed with brine, it was dried over anhydrous magnesium sulfate. After the drying agent was filtered off, the organic layer was concentrated under reduced pressure.

The obtained residue was dissolved in anhydrous THF (32.0 ml) and cooled to −78° C. under nitrogen atmosphere. Diisobutylaluminum hydride 0.95M toluene solution (21.3 ml, 20.3 mmol) was added dropwise to this solution. After the reaction solution was stirred at −78° C. for 10 minutes, it was stirred at room temperature for 30 minutes. After the reaction solution was ice cooled, followed by addition of 20% Rochelle salt solution, and vigorously stirred for one hour, it was extracted with ethyl acetate. After the organic layer was washed with water and brine sequentially, it was dried over anhydrous magnesium sulfate. After the drying agent was filtered off, the organic layer was concentrated under reduced pressure.

The obtained residue was dissolved in dimethoxyethane (12.0 ml) and cooled to 0° C. under nitrogen atmosphere. After addition of sodium hydride (60%, 394 mg, 9.85 mmol) to this solution and stirring at 0° C. for 20 minutes, p-methoxybenzyl chloride (1.00 ml, 7.39 mmol) and sodium iodide (1.11 g, 7.39 mmol) were added. After the reaction solution was stirred at room temperature for 45 minutes, it was poured into water, which was then extracted with n-hexane. After the organic layer was washed with a sodium sulfite aqueous solution and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; heptane:ethyl acetate=19:1→9:1→5:1) to obtain the title compound (1.52 g) as a colorless oil. The title compound was determined to be a mixture of E:Z=18:7 by $^1$H-NMR.

400 MHz $^1$H-NMR (CDCl$_3$) δ (ppm) 1.62 (d, J=0.8 Hz, 2.16H), 1.74 (d, J=1.2 Hz, 0.84H), 3.30 (s, 1.68H), 3.31 (s, 4.32H), 3.81 (s, 2.16H), 3.82 (s, 0.84H), 4.09 (d, J=6, 0 Hz, 2H), 4.45 (s, 2H), 4.49 (s, 0.72H), 4.87 (s, 0.28H), 5.66 (brt, J=6.6 Hz, 0.28H), 5.78 (brt, J=6.2 Hz, 0.72H), 6.86-6.91 (m, 2H), 7.25-7.28 (m, 2H); IR (neat) 2934, 2834, 1514, 1249, 1112, 1072, 1036, 820 cm$^{-1}$; HRMS C$_{15}$H$_{22}$AgO$_4$ (M+Ag$^+$) Calcd: 373.0569, Found: 373.0552

[Formula 57]

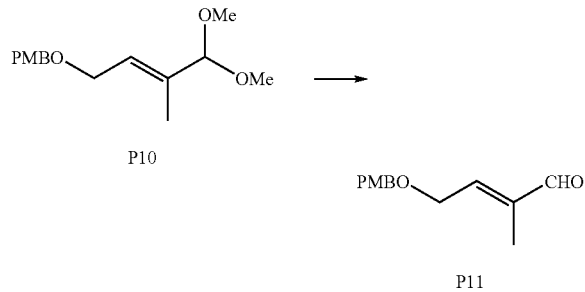

(2) Synthesis of (2E)-4-[(4-methoxybenzyl)oxy]-2-methylbut-2-enal (P11)

1-({[(2E)-4,4-dimethoxy-3-methylbut-2-en-1-yl]oxy}methyl)-4-methoxybenzene (1.52 g, 5.71 mmol) was dissolved in acetonitrile (16.0 ml), followed by addition of 1N hydrochloric acid (4.00 ml) and the reaction solution was stirred at room temperature for one hour. Subsequently, 2N hydrochloric acid (4.00 ml) to the reaction solution was added and it was further stirred for four hours. The reaction solution was poured into a saturated aqueous solution of sodium hydrogen carbonate, which was then extracted with diethyl ether. After the organic layer was washed with water and brine sequentially, it was dried over anhydrous magnesium sulfate. The drying agent was filtered off and the organic layer was concentrated under reduced pressure to obtain the title compound (1.52 g) as a colorless oil.

400 MHz $^1$H-NMR (CDCl$_3$) δ (ppm) 1.73 (dt, J=1.2, 1.2 Hz, 3H), 3.82 (s, 3H), 4.32 (dq, J=1.2, 5.6 Hz, 2H), 4.52 (s, 2H), 6.60 (tq, J=1.2, 5.6 Hz, 1H), 6.88-6.92 (m, 2H), 7.26-7.30 (m, 2H), 9.44 (s, 1H); 100 MHz $^{13}$C-NMR (CDCl$_3$ δ (ppm) 9.20, 54.94, 66.17, 72.45, 113.63, 129.24, 129.32, 139.04, 149.47, 159.18, 194.10; IR (neat) 2837, 1688, 1612, 1512, 1249, 1074, 1033, 820 cm$^{-1}$; HRMS C$_{13}$H$_{16}$NaO$_3$ (M+Na$^+$) Calcd: 243.0997, Found: 243.1044

Step 6

Synthesis of (1S,3R,4S,5E)-4-{[tert-butyl(dimethyl)silyl]oxy}-7-[(4-methoxybenzyl)oxy]-1,3,5-trimethyl-2-oxohept-5-en-1-yl benzoate

[Formula 58]

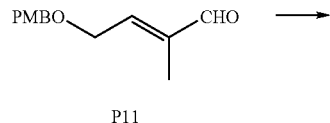

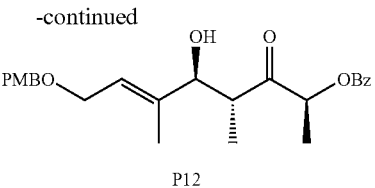

(1) Synthesis of (1S,3R,4S,5E)-4-hydroxy-7-[(4-methoxybenzyl)oxy]-1,3,5-trimethyl-2-oxohept-5-en-1-yl benzoate (P12)

This reaction was performed with reference to the literature (Paterson, I.; Wallac, D.; Cowden, C. J.; Synthesis, 1998, 639-652.). (S)-2-benzoyloxypentane-3-one used in this step was prepared by a method described in this literature.

Anhydrous diethyl ether distilled by using lithium aluminum hydride immediately before use was used in this step.

N,N-dimethylethylamine (24.0 ml, 221 mmol) was added to an anhydrous diethyl ether (500 ml) solution of dicyclohexylboron chloride (38.8 ml, 177 mmol) prepared from a commercial boron monochrolide-methyl sulfide complex by a method described in the literature (Paterson, I.; Temal-Laib, T.; Org. Lett., 2002, 4(15), 2473-2476.) under nitrogen atmosphere −78° C. and the reaction solution was stirred at −78° C. for 15 minutes. An anhydrous diethyl ether (400 ml) solution of (S)-2-benzoyloxy pentane-3-one (30.4 g, 148 mmol) was added dropwise to this reaction solution over 35 minutes, and it was stirred at −78° C. for 10 minutes and then stirred at 0° C. for two hours. The reaction solution was cooled to −78° C. again and an anhydrous diethyl ether (400 ml) solution of (2E)-4-[(4-methoxybenzyl)oxy]-2-methylbut-2-enal (27.0 g, 123 mmol) was added dropwise over 20 minutes and it was stirred at −78° C. for two hours and then stirred at −26° C. overnight. After the reaction solution was warmed to 0° C., methanol (400 ml), phosphate buffer (pH=7, 400 ml) and 30% hydrogen peroxide solution (350 ml) were added sequentially and the reaction solution was stirred at 0° C. for one hour. The reaction solution was poured into water, which was then extracted with ethyl acetate. The organic layer was washed with water and brine sequentially and dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=4:1→2:1). The obtained white solid was recrystallized (n-hexane:ethyl acetate) to obtain the title compound (42.6 g, >99% de) as a colorless needle. The optical purity was determined by HPLC using a chiral column (DAICEL, commercial name CHIRALCEL OD; n-hexane:isopropylalcohol=95:5).

400 MHz $^1$H-NMR (CDCl$_3$) δ (ppm) 1.07 (d, J=7.2 Hz, 3H), 1.57 (d, J=7.2 Hz, 3H), 1.63 (s, 3H), 2.02 (d, J=3.8 Hz, 1H), 3.04 (dq, J=7.2, 9.2 Hz, 1H), 3.81 (s, 3H), 3.80-4.10 (m, 2H), 4.24 (dd, J=3.8, 9.2 Hz, 1H), 4.44 (s, 2H), 5.45 (q, J=7.2 Hz, 1H), 5.65 (brt, J=6.4 Hz, 1H), 6.86-6.90 (m, 2H), 7.24-7.28 (m, 2H), 7.44-7.47 (m, 2H), 7.56-7.61 (m, 1H), 8.07-8.10 (m, 2H); 100 MHz $^{13}$C-NMR (CDCl$_3$) δ (ppm) 11.07, 14.46, 15.46, 45.38, 55.22, 65.75, 72.00, 75.06, 79.48, 113.75, 126.06, 128.38, 129.36, 129.51, 129.74, 130.20, 133.23, 138.19, 159.18, 165.83, 210.72; IR (KBr) 3466, 3050, 2991, 2967, 2932, 2871, 2836, 1731, 1719, 1513, 1453, 1301, 1247, 1121, 1072, 1038, 996, 711 cm$^{-1}$; HRMS C$_{25}$H$_{30}$NaO$_6$ (M+Na$^+$) Calcd: 449.1940, Found: 449.1951, [α]$_D^{25}$ +30.3 (c 1.00, CHCl$_3$)

[Formula 59]

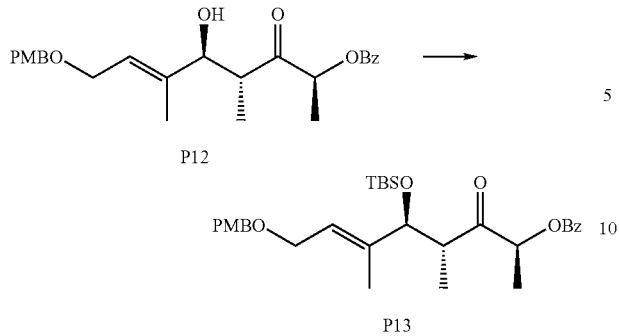

(2) Synthesis of (1S,3R,4S,5E)-4-{[tert-butyl(dimethyl)silyl]oxy}-7-[(4-methoxybenzyl)oxy]-1,3,5-trimethyl-2-oxohept-5-en-1-yl benzoate (P13)

2,6-Lutidine (38.2 ml, 328 mmol) was added to an anhydrous dichloromethane (1.00 l) solution of (1S,3R,4S,5E)-4-hydroxy-7-[(4-methoxybenzyl)oxy]-1,3,5-trimethyl-2-oxohept-5-en-1-yl benzoate (70.0 g, 164 mmol) at −78° C. under nitrogen atmosphere. Trifluoromethanesulfonic acid tert-butyldimethylsilyl ester (56.5 ml, 246 mmol) was added dropwise to the reaction solution over 10 minutes. After the reaction solution was stirred at −78° C. for one and a half hour, a saturated sodium hydrogen carbonate aqueous solution was added at −78° C. The reaction solution was warmed to room temperature, which was then extracted with dichloromethane. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=8:1) to obtain the title compound (89.0 g) as a colorless oil.

400 MHz $^1$H-NMR (CDCl$_3$) δ (ppm) −0.02 (s, 3H), −0.01 (s, 3H), 0.82 (s, 9H), 0.97 (d, J=7.2 Hz, 3H), 1.54 (d, J=7.2 Hz, 3H), 1.58 (s, 3H), 3.00 (dq, J=7.2, 9.6 Hz, 1H), 3.81 (s, 3H), 4.04 (d, J=6.0 Hz, 2H), 4.28 (d, J=9.6 Hz, 1H), 4.43 (s, 2H), 5.43 (q, J=7.2 Hz, 1H), 5.59 (brt, J=6.0 Hz, 1H), 6.86-6.90 (m, 2H), 7.24-7.27 (m, 2H), 7.43-7.47 (m, 2H), 7.56-7.60 (m, 1H), 8.07-8.09 (m, 2H); 100 MHz $^{13}$C-NMR (CDCl$_3$) δ (ppm) −5.17, −4.78, 10.79, 14.54, 15.17, 18.01, 25.75, 46.17, 55.21, 65.83, 71.72, 75.20, 80.54, 113.75, 126.24, 128.36, 129.22, 129.66, 129.76, 130.35, 133.16, 138.11, 159.15, 165.68, 209.02; IR (neat) 2954, 2931, 2856, 1721, 1512, 1453, 1301, 1250, 1117, 1070, 1040, 837, 778, 713 cm$^{-1}$; HRMS C$_{31}$H$_{44}$NaO$_6$Si (M+Na$^+$) Calcd: 563.2805, Found: 563.2786; [α]$_D^{25}$ +12.6 (c 1.01, CHCl$_3$)

Step 7

(3S,4S,5E)-7-[(4-methoxybenzyl)oxy]-3,5-dimethylhepta-1,5-dien-4-ol

[Formula 60]

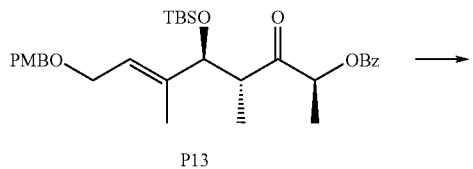

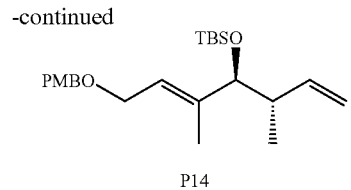

(1) Synthesis of tert-butyl({(1S,2E)-4-[(4-methoxybenzyl)oxy]-2-methyl-1-[(1S)-1-methylprop-2-en-1-yl]but-2-en-1-yl}oxy)dimethylsilane (P14)

To an anhydrous THF (10.0 ml) solution of (1S,3R,4S,5E)-4-{[tert-butyl(dimethyl)silyl]oxy}-7-[(4-methoxybenzyl)oxy]-1,3,5-trimethyl-2-oxohept-5-en-1-yl benzoate (1.00 g, 1.85 mmol), lithium boron hydride 2M THF (18.5 ml, 37.0 mmol) solution was added at −78° C. under nitrogen atmosphere. The reaction solution was stirred overnight while warmed to room temperature. After the reaction solution was ice cooled and water was added thereto, it was extracted with ethyl acetate. After the organic layer was washed with water and brine sequentially, it was dried over anhydrous magnesium sulfate. The drying agent was filtered off and the organic layer was concentrated under reduced pressure to obtain a white solid (611 mg).

300 mg from the obtained white solid was dissolved in a mixed solvent of THF-water (4:1, 6.00 ml). Sodium periodate (438 mg, 2.05 mmol) was added to the reaction solution. After the reaction solution was stirred to at room temperature for one and a half hour, it was poured into water, which was then extracted with ethyl acetate. After the organic layer was washed with water and brine sequentially, it was dried over anhydrous magnesium sulfate. After the drying agent was filtered off, the organic layer was concentrated under reduced pressure.

The obtained residue was dissolved in anhydrous THF (4.00 ml) and added dropwise at under nitrogen atmosphere at −15° C. to an anhydrous THF (4.00 ml) solution of methylenetriphenylphosphorane prepared by a conventional method from methyl iodide triphenylphosphonium (415 mg, 1.02 mmol) and 2.59M n-butyllithium n-hexane (397 μl, 1.03 mmol) solution. After the reaction solution was stirred at −15° C. for one hour, it was poured into water, which was then extracted with ethyl acetate. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=19:1) to obtain the title compound (258 mg) as a colorless oil.

400 MHz $^1$H-NMR (CDCl$_3$) δ (ppm) −0.03 (s, 3H), 0.02 (s, 3H), 0.87 (d, J=7.2 Hz, 3H), 0.88 (s, 9H), 1.58 (s, 3H), 2.24-2.33 (m, 1H), 3.72 (d, J=7.2 Hz, 1H), 3.81 (s, 3H), 4.05 (d, J=6.4 Hz, 2H), 4.42 (s, 2H), 4.98 (brd, J=10.4 Hz, 1H), 4.99 (brd, J=17.4 Hz, 1H), 5.50 (brt, J=6.4 Hz, 1H), 5.84 (ddd, J=7.6, 10.4, 17.4 Hz, 1H), 6.87-6.89 (m, 2H), 7.25-7.27 (m, 2H); 100 MHz $^{13}$C-NMR (CDCl$_3$) δ (ppm) −5.02, −4.55, 11.74, 16.65, 18.16, 25.81, 42.07, 55.12, 65.84, 71.32, 82.35, 113.68, 113.91, 123.76, 129.19, 130.55, 140.26, 141.67, 159.07; IR (neat) 2956, 2929, 2856, 1514, 1249, 1065, 1040, 836, 775 cm$^{-1}$; HRMS C$_{23}$H$_{38}$NaO$_3$Si (M+Na$^+$) Calcd: 413.2488, Found: 413.2504; [α]$_D^{26}$ −2.26 (c 1.02, CHCl$_3$)

[Formula 61]

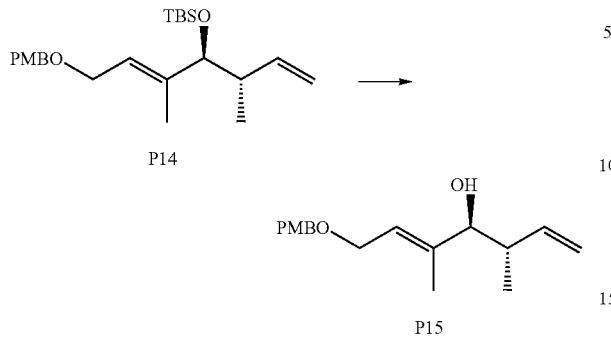

(2) Synthesis of (3S,4S,5E)-7-[(4-methoxybenzyl)oxy]-3,5-dimethylhepta-1,5-dien-4-ol (P15)

1N hydrochloric acid (100 ml) was added to an acetonitrile (300 ml) solution of tert-butyl({(1S,2E)-4-[(4-methoxybenzyl)oxy]-2-methyl-1-[(1S)-1-methylprop-2-en-1-yl]but-2-en-1-yl}oxy)dimethylsilane (41.8 g, 107 mmol). After the reaction solution was stirred at room temperature for ten and a half hours, it was poured into brine and extracted with ethyl acetate. After the organic layer was washed with brine, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=4:1→3:1→2:1) and was obtained title compound (26.8 g) as a colorless oil.

400 MHz $^1$H-NMR (CDCl$_3$) δ (ppm) 0.93 (d, J=6.4 Hz, 3H), 1.64 (s, 3H), 1.77 (brs, 1H), 2.28-2.39 (m, 1H), 3.71 (d, J=8.0 Hz, 1H), 3.81 (s, 3H), 4.07 (d, J=6.4 Hz, 2H), 4.45 (s, 2H), 5.15 (brd, J=10.4 Hz, 1H), 5.16 (brd, J=17.1 Hz, 1H), 5.62 (brt, J=6.4 Hz, 1H), 5.75 (ddd, J=8.4, 10.4, 17.1 Hz, 1H), 6.86-6.90 (m, 2H), 7.25-7.29 (m, 2H); 100 MHz $^{13}$C-NMR (CDCl$_3$) δ (ppm) 11.44, 16.62, 41.60, 55.04, 65.74, 71.58, 80.52, 113.59, 116.10, 124.73, 129.19, 130.24, 138.94, 140.67, 159.00; IR (neat) 3443, 2962, 2931, 2862, 1613, 1513, 1456, 1301, 1249, 1174, 1065, 1035, 913, 820 cm$^{-1}$; HRMS C$_{17}$H$_{24}$NaO$_3$ (M+Na$^+$) Calcd: 299.1623, Found: 299.1612; [α]$_D^{26}$ −14.1 (c 1.02, CHCl$_3$)

Step 8

Synthesis of (2S,3aS,4E,6S,7S,13aR)-11-{[tert-butyl(dimethyl)silyl]oxy}-7-{(1E)-3-[(4-methoxybenzyl)oxy]-1-methylprop-1-en-1-yl}-6,13a-dimethyl-2-phenyl-3a,6,7,10,11,12,13,13a-octahydro-9H-[1,3]dioxolo[4,5-f]oxacyclododecin-9-one

[Formula 62]

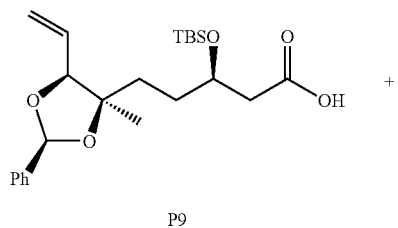

(1) Synthesis of (1S,2E)-4-[(4-methoxybenzyl)oxy]-2-methyl-1-[(1S)-1-methylprop-2-en-1-yl]but-2-en-1-yl 3-{[tert-butyl(dimethyl)silyl]oxy}-5-[(2S,4R,5S)-4-methyl-2-phenyl-5-vinyl-1,3-dioxolan-4-yl]pentanoate (P16)

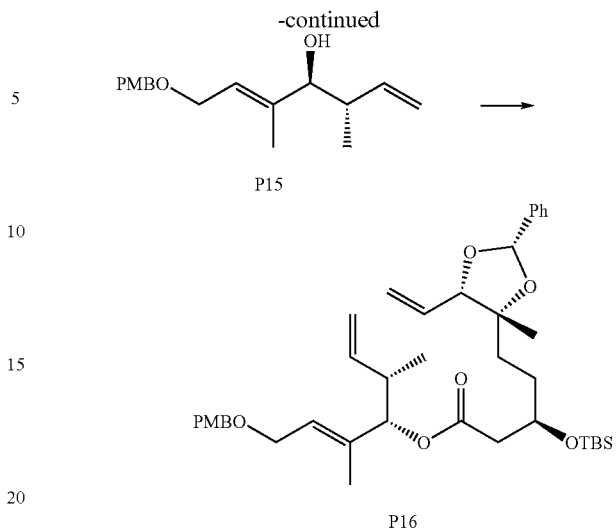

This reaction was performed with reference to the literature (Inanaga, J.; Hirata, K.; Saeki, H; Katsuki, T.; Yamaguchi, M.; Bull. Chem. Soc. Jpn. 1979, 52(7), 1989-1993.).

To an anhydrous THF (130 ml) solution of (3R)-3-{[tert-butyl(dimethyl)silyl]oxy}-5-[(2S,4R,5S)-4-methyl-2-phenyl-5-vinyl-1,3-dioxolan-4-yl] pentanoic acid (6.50 g, 15.5 mmol) was added triethylamine (2.80 ml, 20.2 mmol) under nitrogen atmosphere and cooled to 0° C. 2,4,6-Trichlorobenzoyl chloride (2.65 ml, 17.0 mmol) was added to the reaction solution. After the reaction solution was stirred at 0° C. for 10 minutes, it was stirred at room temperature for two hours. After the reaction solution was filtered with celite, the organic layer was concentrated under reduced pressure. To the obtained residue, an anhydrous toluene (130 ml) solution of (3S,4S,5E)-7-[(4-methoxybenzyl)oxy]-3,5-dimethylhepta-1,5-dien-4-ol (4.71 g, 17.0 mmol) and 4-dimethylaminopyridine (2.46 g, 20.2 mmol) were added under nitrogen atmosphere. After the reaction solution was stirred at room temperature for two hours, it was poured into 0.5N hydrochloric acid and extracted with ethyl acetate. After the organic layer was washed with a saturated sodium hydrogen carbonate aqueous solution, water and brine sequentially, it was dried over magnesium sulfate anhydrous. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=10:1→5:1) to obtain the title compound (9.81 g) as a colorless oil.

400 MHz $^1$H-NMR (CDCl$_3$) δ (ppm) 0.01 (s, 3H), 0.02 (s, 3H), 0.86 (s, 9H), 0.94 (d, J=6.8 Hz, 3H), 1.22-1.32 (m, 1H), 1.32 (s, 3H), 1.57-1.65 (m, 2H), 1.60 (s, 3H), 1.65-1.79 (m, 1H), 2.32 (dd, J=6.0, 15.2 Hz, 1H), 2.43 (dd, J=6.0, 15.2 Hz, 1H), 2.42-2.52 (m, 1H), 3.80 (s, 3H), 4.02 (d, J=6.4 Hz, 2H), 4.01-4.08 (m, 1H), 4.26 (dt, J=1.0, 7.0 Hz, 1H), 4.40 (s, 2H), 4.96-5.05 (m, 3H), 5.29 (ddd, J=1.0, 1.6, 10.5 Hz, 1H), 5.41 (dt, J=1.6, 17.5 Hz, 1H), 5.62 (brt, J=6.2 Hz, 1H), 5.69 (ddd, J=8.0, 10.4, 17.2 Hz, 1H), 5.88 (ddd, J=7.0, 10.5, 17.5 Hz, 1H), 5.90 (s, 1H), 6.85-6.89 (m, 2H), 7.23-7.26 (m, 2H), 7.26-7.37 (m, 3H), 7.48-7.52 (m, 2H); 100 MHz $^{13}$C-NMR (CDCl$_3$) δ (ppm) −4.83, −4.76, 12.65, 16.63, 17.85, 22.32, 25.73, 31.21, 32.28, 39.94, 42.72, 55.09, 65.60, 69.21, 71.53, 81.37, 82.18, 87.72, 102.16, 113.65, 115.17, 118.64, 126.03, 126.67, 128.14, 129.00, 129.27, 130.25, 132.66, 135.33, 137.90, 139.83, 159.08, 170.36; IR (neat) 2957, 2931, 2856, 1736, 1612, 1250, 1173, 1090, 1065, 1036, 836 cm$^{-1}$; HRMS C$_{40}$H$_{58}$NaO$_7$Si (M+Na$^+$) Calcd: 701.3849, Found: 701.3824; [α]$_D^{23}$ −2.69 (c 1.09, CHCl$_3$)

[Formula 63]

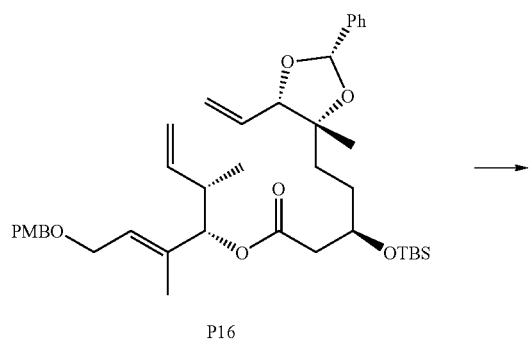

P16

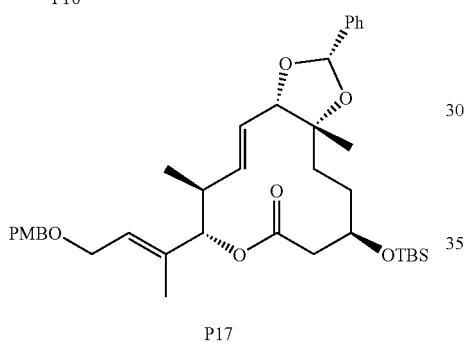

P17

(2) Synthesis of (2S,3aS,4E,6S,7S,13aR)-11-{[tert-butyl(dimethyl)silyl]oxy}-7-{(1E)-3-[(4-methoxybenzyl)oxy]-1-methylprop-1-en-1-yl}-6,13a-dimethyl-2-phenyl-3a,6,7,10,11,12,13,13a-octahydro-9H-[1,3]dioxolo[4,5-f]oxacyclododecin-9-one (P17)

Anhydrous toluene distilled by using benzophenone ketyl immediately before use under Ar atmosphere was used in this step.

(1S,2E)-4-[(4-methoxybenzyl)oxy]-2-methyl-1-[(1S)-1-methylprop-2-en-1-yl]but-2-en-1-yl 3-{[tert-butyl(dimethyl)silyl]oxy}-5-[(2S,4R,5S)-4-methyl-2-phenyl-5-vinyl-1,3-dioxolan-4-yl]pentanoate (1.10 g, 1.63 mmol) and 2,6-di-tert-butyl-4-methylphenol (35.9 mg, 0.16 mmol) were dissolved in anhydrous toluene under Ar atmosphere. The reaction solution was heated to reflux for one hour. An anhydrous toluene (330 ml) solution of the second generation Hoveyda-Grubbs catalyst; [1,3-bis-(2,4,6-trimethylphenyl)-2-imidazolidinylidene]dichloro(O-isopropoxyphenylmethylene)ruthenium (102 mg, 0.16 mmol) was added to the reaction solution. After the reaction solution was heated to reflux for five hours, it was cooled to room temperature. The reaction solution was filtered with silica gel (Fuji Silysia, commercial name Chromatorex, NH, 200-350 mesh) and the filtrate was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=8:1) to obtain the title compound (486.1 mg) as a white solid. This was obtained as a colorless needle by recrystallization (hexane:ethyl acetate).

400 MHz $^1$H-NMR (CDCl$_3$) δ (ppm) 0.07 (s, 3H), 0.09 (s, 3H), 0.88 (s, 9H), 0.91 (d, J=6.8 Hz, 3H), 1.38 (s, 3H), 1.38-1.46 (m, 1H), 1.48-1.56 (m, 1H), 1.61 (s, 3H), 1.62-1.68 (m, 1H), 1.99-2.10 (m, 1H), 2.31 (dd, J=10.4, 14.7 Hz, 1H), 2.52-2.58 (m, 1H), 2.58 (dd, J=4.4, 14.7 Hz, 1H), 3.81 (s, 3H), 3.92-4.01 (m, 1H), 4.04 (d, J=6.4 Hz, 2H), 4.19 (d, J=9.4 Hz, 1H) 4.42 (s, 2H), 4.97 (d, J=10.8 Hz, 1H), 5.41 (dd, J=9.8, 15.2 Hz, 1H), 5.63 (dd, J=9.4, 15.2 Hz, 1H), 5.74 (brt, J=6.4 Hz, 1H), 5.91 (s, 1H), 6.87-6.90 (m, 2H), 7.24-7.26 (m, 2H), 7.36-7.40 (m, 3H), 7.49-7.51 (m, 2H); 100 MHz $^{13}$C-NMR (CDCl$_3$) δ (ppm) −4.73, −4.61, 11.50, 16.72, 17.80, 22.69, 25.62, 31.44, 34.31, 39.97, 43.98, 55.02, 65.45, 71.51, 71.69, 81.55, 83.44, 85.18, 101.07, 113.61, 126.62, 128.18, 128.41, 129.12, 129.21, 129.47, 130.05, 134.39, 137.55, 137.63, 159.05, 168.89; IR (neat) 2932, 2856, 1735, 1513, 1460, 1247, 1066, 1034, 1006, 978, 836 cm$^{-1}$; HRMS C$_{38}$H$_{54}$NaO$_7$Si (M+Na$^+$) Calcd: 673.3536, Found: 673.3505; [α]$_D^{28}$ −14.8 (c 1.03, CHCl$_3$)

Step 9

Synthesis of (2E)-3-((2S,3aS,4E,6S,7S,13aR)-11-{[tert-butyl (dimethyl)silyl]oxy}-6,13a-dimethyl-9-oxo-2-phenyl-6,7,9,10,11,12,13,13a-octahydro-3aH-[1,3]dioxolo[4,5-f]oxacyclododecin-7-yl)but-2-enal

[Formula 64]

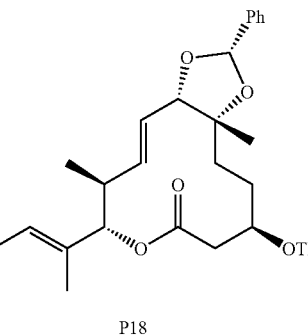

P17

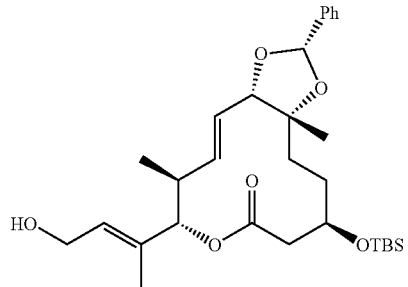

P18

(1) Synthesis of (2S,3aS,4E,6S,7S,13aR)-11-{[tert-butyl(dimethyl)silyl]oxy}-7-{(1E)-3-hydroxy-1-methylprop-1-en-1-yl}-6,13a-dimethyl-2-phenyl-3a, 6,7,10,11,12,13,13a-octahydro-9H-[1,3]dioxolo[4,5-f]oxacyclododecin-9-one (P18)

(2S,3aS,4E,6S,7S,13aR)-11-{[tert-butyl(dimethyl)silyl]oxy}-7-{(1E)-3-[(4-methoxybenzyl)oxy]-1-methylprop-1- en-1-yl}-6,13a-dimethyl-2-phenyl-3a,6,7,10,11,12,13,13a-octahydro-9H-[1,3]dioxolo[4,5-f]oxacyclododecin-9-one (710 mg, 1.09 mmol) was dissolved in dichloromethane (14.0 ml) and a phosphate buffer (pH=7, 1.40 ml). 2,3-Dichloro-5,6-dicyano-1,4-benzoquinone (297 mg, 1.31 mmol) was added to the reaction solution at 0° C. and stirred for three hours. 2,3-Dichloro-5,6-dicyano-1,4-benzoquinone (74.3 mg, 0.33 mmol) was added and the reaction solution was stirred at 0° C. for one and a half hour. After 2,3-dichloro-5,6-dicyano-1,4-benzoquinone (74.3 mg, 0.33 mmol) was added and the reaction solution was stirred at 0° C. for further 30 minutes, the reaction solution was filtered with silica gel (Fuji Silysia, commercial name Chromatorex, NH, 200-350 mesh). The filtrate was washed with a saturated sodium hydrogen carbonate aqueous solution, distilled water and brine sequentially and dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=4:1→3:1) to obtain the title compound (460 mg) as a colorless needle.

400 MHz $^1$H-NMR (CDCl$_3$) δ (ppm) 0.08 (s, 3H), 0.09 (s, 3H), 0.88 (s, 9H), 0.90 (d, J=6.8 Hz, 3H), 1.25 (t, J=5.6 Hz, 1H), 1.38-1.46 (m, 2H), 1.39 (s, 3H), 1.60-1.68 (m, 1H), 1.65 (s, 3H), 2.00-2.09 (m, 1H), 2.32 (dd, J=10.2, 14.6 Hz, 1H), 2.52-2.59 (m, 1H), 2.59 (dd, J=4.2, 14.6 Hz, 1H), 3.92-4.01 (m, 1H), 4.16-4.27 (m, 3H), 4.95 (d, J=10.4 Hz, 1H), 5.41 (dd, J=9.8, 15.2 Hz, 1H), 5.64 (dd, J=9.6, 15.2 Hz, 1H), 5.75 (brt, J=5.8 Hz, 1H), 5.91 (s, 1H), 7.36-7.41 (m, 3H), 7.49-7.52 (m, 2H); 100 MHz $^{13}$C-NMR (CDCl$_3$) δ (ppm) −4.67, −4.56, 11.24, 16.69, 17.88, 22.75, 25.67, 31.50, 34.33, 39.92, 43.98, 58.64, 71.49, 81.86, 83.55, 85.25, 101.15, 126.70, 128.28, 129.25, 129.56, 130.77, 133.52, 137.58, 169.25; IR (KBr) 3232, 2937, 2858, 1730, 1243, 1107, 1082, 1067, 1007, 973, 836, 776, 700 cm$^{-1}$; HRMS C$_{30}$H$_{46}$NaO$_6$Si (M+Na$^+$) Calcd: 553.2961, Found: 553.2948; [α]$_D^{23}$ −11.5 (c 1.02, CHCl$_3$)

[Formula 65]

(2) Synthesis of (2S,3aS,4E,6S,7S,13aR)-11-{[tert-butyl(dimethyl)silyl]oxy}-7-[(E)-2-formyl-1-methyl-eth-1-en-1-yl]-6,13a-dimethyl-2-phenyl-3a,6,7,10,11,12,13,13a-octahydro-9H-[1,3]dioxolo[4,5-f]oxacyclododecin-9-one (P19)

Dess-Martin reagent (565 mg, 1.33 mmol) was added to a dichloromethane (12.0 ml) solution of (2S,3aS,4E,6S,7S,13aR)-11-{[tert-butyl(dimethyl)silyl]oxy}-7-{(1E)-3-hydroxy-1-methylprop-1-en-1-yl}-6,13a-dimethyl-2-phenyl-3a,6,7,10,11,12,13,13a-octahydro-9H-[1,3]dioxolo[4,5-f]oxacyclododecin-9-one (587 mg, 1.11 mmol). The reaction solution was stirred at room temperature for 30 minutes. The reaction solution was diluted with ether and washed with a saturated sodium hydrogen carbonate aqueous solution containing sodium sulfite, water and brine sequentially and dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=10:1→8:1→6:1) to obtain the title compound (587 mg) as a white solid. This was obtained as a colorless crystal by recrystallization (hexane:ethyl acetate).

400 MHz $^1$H-NMR (CDCl$_3$) δ (ppm) 0.09 (s, 3H), 0.10 (s, 3H), 0.89 (s, 9H), 0.95 (d, J=6.8 Hz, 3H), 1.38-1.50 (m, 2H), 1.40 (s, 3H), 1.63-1.70 (m, 1H), 1.96-2.10 (m, 1H), 2.17 (d, J=1.2 Hz, 3H), 2.37 (dd, J=9.6, 14.4 Hz, 1H), 2.60 (dd, J=4.0, 14.4 Hz, 1H), 2.61 (m, 1H), 3.93-4.03 (m, 1H), 4.20 (d, J=9.6 Hz, 1H), 4.92 (d, J=10.4 Hz, 1H), 5.41 (dd, J=9.2, 15.2 Hz, 1H), 5.69 (dd, J=9.6, 15.2 Hz, 1H), 5.92 (s, 1H), 6.07 (dd, J=1.2, 7.6 Hz, 1H), 7.34-7.42 (m, 3H), 7.48-7.52 (m, 2H), 10.0 (d, J=7.6 Hz, 1H); 100 MHz $^{13}$C-NMR (CDCl$_3$) δ (ppm) −4.70, −4.60, 13.20, 16.31, 17.87, 22.66, 25.64, 31.46, 34.14, 40.40, 43.19, 71.13, 80.52, 83.52, 85.00, 101.22, 126.63, 128.28, 129.25, 129.84, 130.58, 136.19, 137.59, 155.92, 168.80, 190.56; IR (KBr) 2954, 2935, 2880, 2858, 2787, 2755, 1739, 1674, 1461, 1401, 1240, 1224, 1101, 1004, 980, 830, 775, 698 cm$^{-1}$; HRMS C$_{30}$H$_{44}$NaO$_6$Si (M+Na$^+$) Calcd: 551.2805, Found: 551.2803; [α]$_D^{27}$ +4.00 (c 1.06, CHCl$_3$)

Step 10

Synthesis of (3S)-4-(benzyloxy)-3-methylbutan-1-ol

[Formula 66]

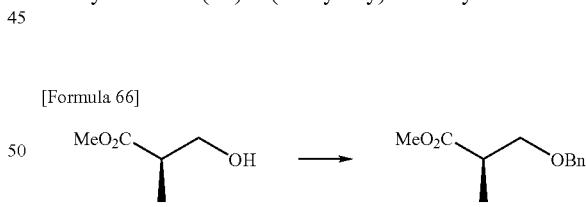

(1) Synthesis of methyl (2R)-3-(benzyloxy)-2-methylpropanoate (P20)

This reaction was performed with reference to the literature (Widmer, U.; Synthesis, 1987, 568-570.).

Methyl (R)-3-hydroxy-isobutyrate (6.30 g, 53.3 mmol) was dissolved in a mixed solution (180 ml) of dichloromethane-cyclohexane (1:1), followed by addition of benzyl-2,2,2-trichloroacetimidate (12.0 ml, 64.6 mmol) at room temperature. After trifluoromethanesulfonic acid (0.80 ml, 5.40 mmol) was added dropwise to this, the reaction solution

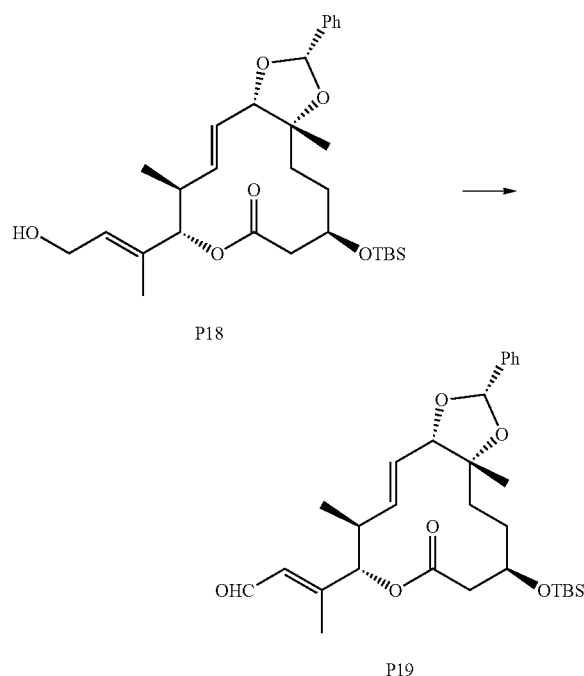

was stirred at room temperature for three hours. After the reaction solution was diluted with dichloromethane, it was washed with a sodium hydrogen carbonate aqueous solution and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=30:1) and the title compound (9.79 g) was obtained as a colorless oil.

400 MHz $^1$H-NMR (CDCl$_3$) δ (ppm) 1.19 (d, J=7.2 Hz, 3H), 2.74-2.84 (m, 1H), 3.50 (dd, J=6.0, 9.2 Hz, 1H), 3.66 (dd, J=7.2, 9.2 Hz, 1H), 3.69 (s, 3H), 4.52 (s, 2H), 7.20-7.37 (m, 5H); 100 MHz $^{13}$C-NMR (CDCl$_3$) δ (ppm) 13.91, 40.12, 51.65, 71.89, 73.02, 127.51, 127.53, 128.28, 138.09, 175.24; IR (neat) 2977, 2946, 2862, 2362, 2323, 1738, 1458, 1202 cm$^{-1}$; HRMS C$_{12}$H$_{16}$NaO$_3$ (M+Na$^+$) Calcd: 231.0997, Found: 231.0989; $[\alpha]_D^{28}$ −10.9 (c 2.10, CHCl$_3$)

[Formula 67]

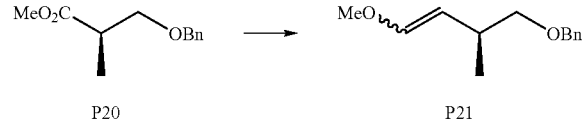

P20    P21

(2) Synthesis of ({[(2S)-4-methoxy-2-methylbut-3-en-1-yl]oxy}methyl)benzene (P21)

This reaction was performed with reference to the literature (Rich, D. H.; Sun, E. T.; Boparai, A. S.; J. Org. Chem., 1978, 43(18) 3624-3626. Feng, X.; Edstrom, E. D., Tetrahedron Asymmetry, 1999, 10(1), 99-105. Gibson, S. E.; Guillo, N.; Middleton, R. J.; Thuilliez, A.; Tozer, M. J.; J. Chem. Soc. Perkin Trans., 1997, 1, 447-455.).

1.0M diisobutylaluminum hydride toluene solution (3.78 ml) was added dropwise to a toluene (32 ml) solution of methyl (2R)-3-(benzyloxy)-2-methylpropanoate (0.81 g, 3.88 mmol) at −78° C. and the reaction solution was stirred at the same temperature for 1.5 hours. After addition of methanol (0.5 ml, 12.3 mmol), the reaction solution was warmed to room temperature. The reaction solution was stirred for further two hours. The reaction solution was filtered through celite and the filtrate was dried over sodium sulfate. The drying agent was filtered off, the solvent was evaporated under reduced pressure and aldehyde was obtained as a crude product.

After potassium tert-butoxide (0.76 g, 6.76 mmol) was added to a THF (20 ml) solution of (methoxymethyl)triphenylphosphonium chloride (2.54 g, 7.40 mmol) while ice cooling, the mixture was stirred at room temperature for 30 minutes. Subsequently a THF (5 ml) solution of the above aldehyde was added dropwise to this reaction solution at room temperature and stirred for 12 hours. After the reaction solution was diluted with ethyl acetate, it was washed with water and brine. After the organic layer was dried over anhydrous magnesium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=100:1) to obtain the title compound (0.44 g) as a colorless oil. Title compound was determined to be a mixture of E:Z=2:1 by $^1$H-NMR.

400 MHz $^1$H-NMR (CDCl$_3$) δ (ppm) 1.01 (d, J=6.8 Hz, 0.9H), 1.04 (d, J=6.8 Hz, 2.1H), 2.36-2.47 (m, 0.7H), 2.92-3.00 (m, 0.3H), 3.22-3.37 (m, 2H), 3.50 (s, 2.1H), 3.58 (s, 0.9H), 4.23 (dd, J=6.4, 9.2 Hz, 0.3H), 4.52 (s, 2.0H), 4.65 (dd, J=8.0, 12.8 Hz, 0.7H), 5.89 (dd, J=0.8, 6.4 Hz, 0.3H), 6.35 (dd, J=0.8, 12.8 Hz, 0.7H), 7.25-7.36 (m, 5H); 100 MHz $^{13}$C-NMR (CDCl$_3$) δ (ppm) 17.97, 18.43, 29.60, 33.22, 55.67, 59.50, 72.67, 72.88, 75.24, 76.16, 105.60, 109.51, 127.34, 127.45, 127.53, 128.25, 128.31, 138.72, 138.92, 146.35, 147.31; IR (neat) 3060, 3033, 2956, 2935, 2856, 1655, 1454, 1207, 1098, 737 cm$^{-1}$; HRMS C$_{13}$H$_{18}$NaO$_2$ (M+Na$^+$) Calcd: 229.1204, Found: 229.1207.

[Formula 68]

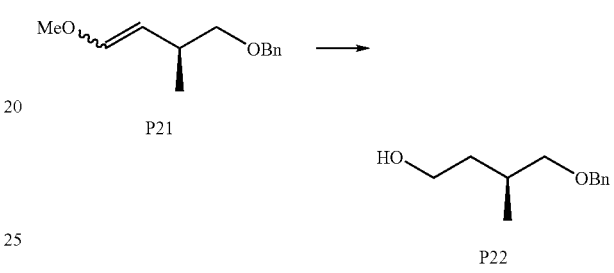

P21

P22

(3) Synthesis of (3S)-4-(benzyloxy)-3-methylbutan-1-ol (P22)

This reaction was performed with reference to the literature (Gibson, S. E.; Guillo, N.; Middleton, R. J.; Thuilliez, A.; Tozer, M. J.; J. Chem. Soc., Perkin Trans., 1997, 1, 447-455.).

Water (10 ml) and formic acid (1 ml) were added to ({[(2S)-4-methoxy-2-methylbut-3-en-1-yl]oxy}methyl)benzene (3.73 g, 18 mmol) and the reaction solution was stirred at room temperature for 10 minutes. The reaction solution was diluted with ethyl acetate and washed with water, a sodium hydrogen carbonate aqueous solution and brine sequentially. After the organic layer was dried over anhydrous sodium sulfate and the drying agent was filtered off, the organic layer was concentrated under reduced pressure.

Sodium borohydride (0.68 g, 18 mmol) was added to a methanol (40 ml) solution of the obtained crude product while ice cooling. After the reaction solution was stirred at the same temperature for 10 minutes, acetone was added thereto. The reaction solution was diluted with ethyl acetate and washed with brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=5:1) to obtain the title compound (3.30 g) as a colorless oil.

400 MHz $^1$H-NMR (CDCl$_3$) δ (ppm) 0.95 (d, J=7.2 Hz, 3H), 1.51-1.68 (m, 2H), 1.89-1.99 (m, 1H), 3.31 (dd, J=7.6, 9.2 Hz, 1H), 3.39 (dd, J=4.8, 9.2 Hz, 1H), 3.61-3.75 (m, 2H), 4.52 (s, 2H), 7.26-7.37 (m, 5H); 100 MHz $^{13}$C-NMR (CDCl$_3$) δ (ppm) 17.51, 31.18, 37.74, 60.88, 73.08, 75.96, 127.57, 127.58, 128.31, 137.99; IR (neat) 3389, 3086, 3058, 3030, 2951, 2929, 2872, 1454, 1363, 1205, 1095, 738, 698 cm$^{-1}$; HRMS C$_{12}$H$_{18}$NaO$_2$ (M+Na$^+$) Calcd: 217.1204, Found: 217.1190; $[\alpha]_D^{29}$ −4.52 (c 2.41, CHCl$_3$)

Step 11

Synthesis of 5-{[(3S)-4-(benzyloxy)-3-methylbutyl]sulfonyl}-1-phenyl-1H-tetrazole

[Formula 69]

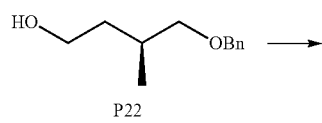

P22

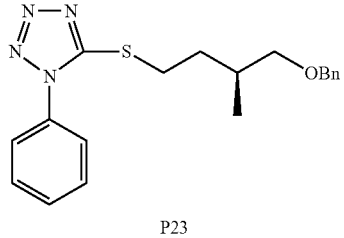

P23

(1) Synthesis of 5-{[(3S)-4-(benzyloxy)-3-methylbutyl]thio}-1-phenyl-1H-tetrazole (P23)

This reaction was performed with reference to the literature (Mitsunobu, O., Synthesis, 1981, 1-28.).

To a THF (60 ml) solution of (3S)-4-(benzyloxy)-3-methylbutan-1-ol (2.76 g, 14.2 mmol), 5-mercapto-1-phenyltetrazole (3.03 g, 17 mmol), triphenylphosphine (4.47 g, 17 mmol) and diethyl azodicarboxylate 40% toluene solution (8.04 ml, 18 mmol) were added while ice cooling. The reaction solution was warmed to room temperature and was stirred for three hours. After the reaction solution was diluted with ethyl acetate, it was washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=15:1→5:1) to obtain the title compound (5.38 g) as a colorless oil.

400 MHz $^1$H-NMR (CDCl$_3$) δ (ppm) 0.99 (d, J=6.8 Hz, 3H), 1.65-1.74 (m, 1H), 1.92-2.03 (m, 2H), 3.26-3.52 (m, 4H), 4.49 (s, 2H), 7.21-7.35 (m, 5H), 7.49-7.58 (m, 5H); 100 MHz $^{13}$C-NMR (CDCl$_3$) δ (ppm) 16.72, 31.23, 32.82, 33.13, 73.02, 75.07, 123.78, 127.48, 128.30, 129.70, 129.99, 133.67, 138.39, 154.37; IR (neat) 3067, 3036, 2956, 2925, 2858, 1598, 1499, 1386, 1092, 761, 696 cm$^{-1}$; HRMS C$_{19}$H$_{23}$N$_4$OS (M+H$^+$) Calcd: 355.1593, Found: 355.1583; $[\alpha]_D^{27}$ −2.62 (c 1.56, CHCl$_3$)

[Formula 70]

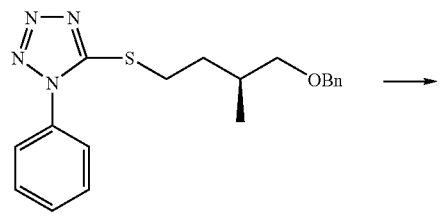

23

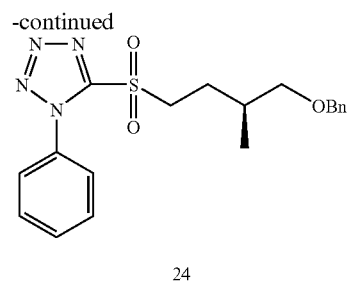

24

(2) Synthesis of 5-{[(3S)-4-(benzyloxy)-3-methylbutyl]sulfonyl}-1-phenyl-1H-tetrazole (P24)

This reaction was performed with reference to the literature (Shultz, H. S.; Freyermuth, H. B.; Buc, S. R., J. Org. Chem., 1963, 28(4), 1140-1142.).

About 30% hydrogen peroxide solution (16.5 ml, 146 mmol) of hexaammonium heptamolybdate tetrahydrate (1.80 g, 1.46 mmol) was added to an ethanol (20 ml) solution of 5-{[(3S)-4-(benzyloxy)-3-methylbutyl]thio}-1-phenyl-1H-tetrazole (5.17 g, 14.6 mmol) at room temperature. After the reaction solution was stirred at room temperature for 24 hours, it was diluted with ethyl acetate and washed with water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=10:1) to obtain the title compound (5.68 g) as a colorless oil.

400 MHz $^1$H-NMR (CDCl$_3$) δ (ppm) 0.98 (d, J=6.8 Hz, 3H), 1.83-2.13 (m, 3H), 3.29 (dd, J=6.8, 9.6 Hz, 1H), 3.40 (dd, J=4.8, 9.6 Hz, 1H), 3.74-3.87 (m, 2H), 4.49 (s, 2H), 7.25-7.36 (m, 5H), 7.55-7.68 (m, 5H); 100 MHz $^{13}$C-NMR (CDCl$_3$) δ (ppm) 16.72, 26.23, 32.49, 54.30, 73.11, 74.70, 125.05, 127.55, 127.62, 128.39, 129.63, 131.37, 132.99, 138.09, 153.38; HRMS C$_{19}$H$_{23}$N$_4$O$_3$S (M+H$^+$) Calcd: 387.1491, Found: 387.1468; $[\alpha]_D^{26}$ −5.28 (c 1.00, CHCl$_3$)

Step 12

Synthesis of (4R)-4-benzyl-3-[(2R,3S)-3-hydroxy-2-methylpentanoyl]-1,3-oxazolidin-2-one

[Formula 71]

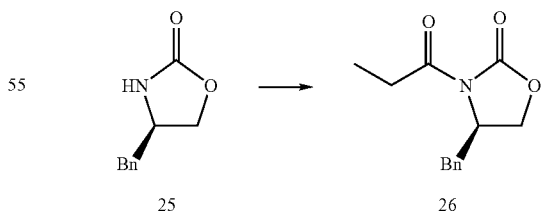

(1) Synthesis of (4R)-4-benzyl-3-propionyl-1,3-oxazolidin-2-one (P26)

This reaction was performed with reference to the literature (Gage, J. R.; Evans, D. A., Organic Synthesis, 1989, 68, 83-91. Chan, P. C.-M.; Chong. J. M.; Kousha, K., Tetrahedron, 1994, 150(9), 2703-2714.).

1.57M n-butyllithium hexane solution (96 ml, 150 mmol) was slowly added dropwise to a THF (400 ml) solution of (R)-4-benzyl-2-oxazolidinone (25.36 g, 143 mmol) at −78° C. under stirring. Subsequently propionyl chloride (13.7 ml, 157 mmol) was added at once and the reaction solution was stirred at the same temperature for 30 minutes. After the reaction solution was warmed to room temperature for 30 minutes, it was diluted with ethyl acetate and washed with water and brine. The organic layer was dried over anhydrous sodium sulfate. After the drying agent was filtered off, the organic layer was concentrated under reduced pressure. The obtained residue was purified by silica gel column chromatography (Merck, commercial name Silica Gel 60, 230-400 mesh; heptane:ethyl acetate=5:1) to obtain the title compound (36.58 g) as a white solid.

400 MHz $^1$H-NMR (CDCl$_3$) δ (ppm) 1.21 (t, J=7.2 Hz, 3H), 2.77 (dd, J=9.6, 13.2 Hz, 1H), 2.88-3.05 (m, 2H), 3.31 (dd, J=3.2, 13.2 Hz, 1H), 4.11-4.23 (m, 2H), 4.65-4.70 (m, 1H), 7.20-7.36 (m, 5H); 100 MHz $^{13}$C-NMR (CDCl$_3$) δ (ppm) 8.52, 29.42, 38.15, 55.39, 66.44, 127.56, 129.17, 129.64, 135.55, 164.52, 174.30; IR (KBr) 3082, 3026, 2984, 2942, 2872, 2360, 2338, 1787, 1702, 1496 cm$^{-1}$; HRMS C$_{13}$H$_{15}$NNaO$_3$ (M+Na$^+$) Calcd: 256.0950, Found: 256.0928; [α]$_D^{27}$ −101.20 (c 1.11, CH$_3$CH$_2$OH), [α]$_D^{25}$ −63.9 (c 1.00, CHCl$_3$)

[Formula 72]

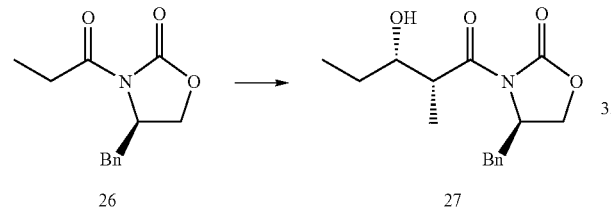

(2) Synthesis of (4R)-4-benzyl-3-[(2R,3S)-3-hydroxy-2-methylpentanoyl]-1,3-oxazolidin-2-one (P27)

This reaction was performed with reference to the literature (Gage, J. R.; Evans, D. A., Organic Synthesis, 1989, 68, 83-91. Chan, P. C.-M.; Chong. J. M.; Kousha, K., Tetrahedron, 1994, 50(9), 2703-2714. Cane, D. E.; Tan, W.; Ott, W. R., J. Am. Chem. Soc., 1993, 115(2) 527-535.).

To a dichloromethane (120 ml) solution of (4R)-4-benzyl-3-propionyl-1,3-oxazolidin-2-one (17.22 g, 73.8 mmol), 1M dibutylboron triflate dichloromethane solution (150 ml, 150 mmol) and triethylamine (24.4 ml, 179 mmol) were added dropwise while ice cooling. Subsequently the reaction solution was cooled to −78° C. and propioaldehyde (10.5 ml, 145 mmol) was added dropwise over five minutes. After the reaction solution was stirred at the same temperature for one hour, it was stirred at 0° C. for two hours. The reaction solution was ice cooled again, followed by addition of a mixed solution of phosphate buffer (pH=7)-distilled water (1:3, 160 ml). After further cooled to −10° C., a mixed solution of methanol −30% hydrogen peroxide solution (2:1, 120 ml) was added thereto, and the mixture was stirred for one hour. After the reaction solution was concentrated under reduced pressure, it was diluted with diethyl ether and washed with a saturated sodium hydrogen carbonate aqueous solution and brine. The organic layer was dried over anhydrous sodium sulfate. After the drying agent was filtered off, the organic layer was concentrated under reduced pressure. The obtained residue was purified by silica gel column chromatography (Merck, commercial name Silica Gel 60, 230-400 mesh; hexane:ethyl acetate=5:1) to obtain the title compound (16.4 g) as a white solid.

400 MHz $^1$H-NMR (CDCl$_3$) δ (ppm) 0.98 (t, J=7.3 Hz, 3H), 1.25 (d, J=6.9 Hz, 3H), 1.40-1.64 (m, 2H), 2.77 (dd, J=9.5, 13.4 Hz, 1H), 2.88 (brs, 1H), 3.25 (dd, 3.1, 13.4 Hz, 1H), 3.80 (dq, J=2.7, 6.8 Hz, 1H), 3.85-3.89 (m, 1H), 4.17-4.25 (m, 2H), 4.68-4.74 (m, 1H), 7.19-7.36 (m, 5H); 100 MHz $^{13}$C-NMR (CDCl$_3$) δ (ppm) 10.24, 10.41, 26.72, 37.75, 41.64, 55.07, 66.13, 72.93, 127.39, 128.93, 129.38, 134.99, 152.98, 177.53; IR (KBr) 3654, 3526, 3375, 3086, 3030, 2976, 2937, 2341, 1760, 1700, 1455, 1376, 1265, 1220, 1117, 1071, 971, 930, 851, 767 cm$^{-1}$; HRMS C$_{16}$H$_{21}$NNaO$_4$ (M+Na$^+$) Calcd: 314.1368, Found: 314.1381; [α]$_D^{28}$ −52.2 (c 1.00, CHCl$_3$)

Step 13

Synthesis of (2R,3S)-2-methyl-3-[(trietylsilyl)oxy]pentanal

[Formula 73]

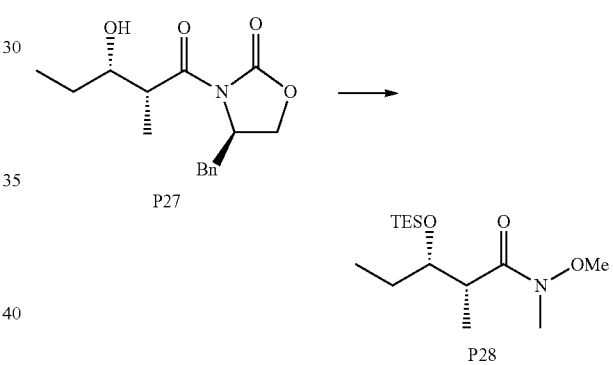

(1) Synthesis of (2R,3S)—N-methoxy-N,2-dimethyl-3-[(triethylsilyl)oxy]pentanamide (P28)

This reaction was performed with reference to the literature (Nahm, S.; Weinreb, S. M., Tetrahedron Lett., 1981, 22(39), 3815-3818. Cane, D. E.; Tan, W.; Ott, W. R., J. Am. Chem. Soc., 1993, 115(2) 527-535. DiBattista, J. P.; Webster, F. X., Bioorg. Med. Chem., 1996, 4(3), 423-428.).

2M trimethylaluminum toluene solution (90 ml, 180 mmol) was added to a THF (180 ml) solution of N,O-dimethylhydroxyamine hydrochloride (18.3 g, 187.6 mmol) at −10° C. under stirring. After the reaction solution was warmed to 0° C. and stirred for 10 minutes, it was warmed to room temperature and further stirred for 30 minutes. The reaction solution was cooled to −10° C. again, and a THF-dichloromethane solution (4:5, 180 ml) of (4R)-4-benzyl-3-[(2R,3S)-3-hydroxy-2-methylpentanoyl]-1,3-oxazolidin-2-one (21.85 g, 75 mmol) was added dropwise to the reaction solution. After the reaction solution was warmed to 0° C. and stirred for two hours, a mixed solution of dichloromethane −0.5N hydrochloric acid (1:1, 80 ml) was added slowly, and the mixture was stirred for one hour at 0° C. The reaction solution was filtered through celite and the filtrate was dried over anhydrous sodium sulfate. After the drying agent was filtered off, the organic layer was concentrated under reduced pressure. The obtained residue was purified by silica gel column chromatography (Merck, commercial name Silica Gel 60; heptane:ethyl acetate=1.5:1) to obtain (2R,3S)-3-hydroxy-N-methoxy-N,2-dimethylpentanamide (13.0 g) as a colorless oil.

400 MHz $^1$H-NMR (CDCl$_3$) δ (ppm) 0.96 (t, J=7.2 Hz, 3H), 1.16 (d, J=7.2 Hz, 3H), 1.34-1.45 (m, 1H), 1.53-2.04 (m, 1H), 2.84-2.94 (m, 1H), 3.19 (s, 3H), 3.71 (s, 3H), 3.74-3.80 (m, 1H); 100 MHz $^{13}$C-NMR (CDCl$_3$) δ (ppm) 10.08, 10.21, 26.64, 31.73, 38.09, 61.35, 72.95, 177.21; IR (neat) 3433, 2971, 2943, 2881, 2361, 2337, 1638, 1461, 993 cm$^{-1}$; HRMS C$_8$H$_{17}$NNaO$_3$ (M+Na$^+$) Calcd: 198.1106, Found: 198.1100; [α]$_D^{25}$ −17.3 (c 1.11, CHCl$_3$)

The above (2R,3S)-3-hydroxy-N-methoxy-N,2-dimethylpentanamide (7.3 g, 41.7 mmol) was dissolved in dichloromethane (150 ml), followed by addition of 2,6-lutidine (10.2 ml, 87 mmol) and trifluoromethanesulfonic acid triethylsilyl ester (14.1 ml, 62 mmol) while ice cooling, and the reaction solution was stirred for five hours. The reaction solution was diluted with dichloromethane and washed with a saturated ammonium chloride aqueous solution and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=10:1) to obtain the title compound (11.95 g) as a colorless oil.

400 MHz $^1$H-NMR (CDCl$_3$) δ (ppm) 0.62 (q, J=8.0 Hz, 6H), 0.90 (t, J=7.2 Hz, 3H), 0.98 (t, J=8.0 Hz, 9H), 1.17 (d, J=6.8 Hz, 3H), 1.40-1.59 (m, 2H), 2.90-3.08 (m, 1H), 3.18 (s, 3H), 3.69 (s, 3H), 3.90 (dt, J=4.8, 8.4 Hz, 1H); 100 MHz $^{13}$C-NMR (CDCl$_3$) δ (ppm) 4.96, 6.74, 8.60, 14.35, 28.25, 31.86, 40.21, 61.16, 74.50, 176.51; IR (neat) 3483, 2958, 2918, 2879, 1743, 1663, 1460, 1384, 1118, 1049, 1007, 857, 741 cm$^{-1}$; HRMS C$_{14}$H$_{32}$NO$_3$Si (M+H$^+$) Calcd: 290.2151, Found: 290.2150; [α]$_D^{27}$ −7.39 (c 1.04, CHCl$_3$)

[Formula 74]

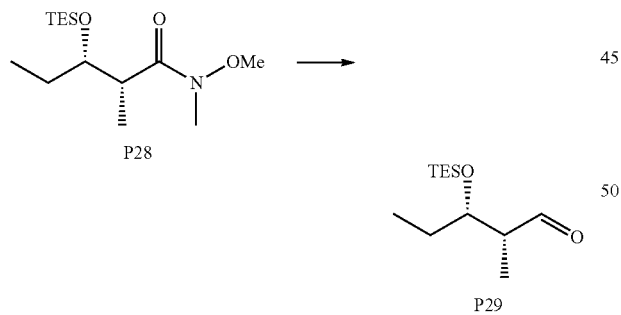

(2) Synthesis of (2R,3S)-2-methyl-3-[(triethylsilyl)oxy]pentanal (P29)

This reaction was performed with reference to the literature (Nahm, S.; Weinreb, S. M., Tetrahedron Lett., 1981, 22(39), 3815-3818).

To a THF (20 ml) solution of (2R,3S)—N-methoxy-N,2-dimethyl-3-[(triethylsilyl)oxy]pentanamide (1.06 g, 3.66 mmol), 1M diisobutylaluminum hydride toluene solution (18 ml) was added dropwise at −78° C. and it was stirred at the same temperature for one hour. After 5% hydrogen chloride methanol solution (2 ml) was added to the reaction solution, the mixture was warmed to room temperature and stirred for one hour. The reaction solution was filtered through celite and the filtrate was concentrated under reduced pressure. The obtained residue was purified by silica gel column chromatography (Merck, commercial name Silica Gel 60, 230-400 mesh; hexane:ethyl acetate=40:1) to obtain the title compound (0.75 g) as a colorless oil.

400 MHz $^1$H-NMR (CDCl$_3$) δ (ppm) 0.60 (q, J=8.0 Hz, 6H), 0.89 (t, J=7.2 Hz, 3H), 0.94 (t, J=8.0 Hz, 9H), 1.06 (d, J=6.8 Hz, 3H), 1.43-1.62 (m, 2H), 2.40-2.49 (m, 1H), 4.05 (ddd, J=3.4, 6.4, 9.6 Hz, 1H), 9.77 (s, 1H); 100 MHz $^{13}$C-NMR (CDCl$_3$) δ (ppm) 5.01, 6.74, 7.43, 10.01, 27.47, 50.82, 73.33, 205.26; IR (neat) 3455, 2958, 2914, 2872, 2715, 2356, 2341, 1726, 1460, 1239, 1011, 740 cm$^{-1}$; HRMS C$_{12}$H$_{26}$NaO$_2$Si (M+Na$^+$) Calcd: 253.1600, Found: 253.1596; [α]$_D^{24}$ −55.3 (c 1.19, CHCl$_3$)

Step 14

Synthesis of (2S,4E,6S,7S)-2,6-dimethyl-7-[(triethylsilyl)oxy]non-4-en-1-ol

[Formula 75]

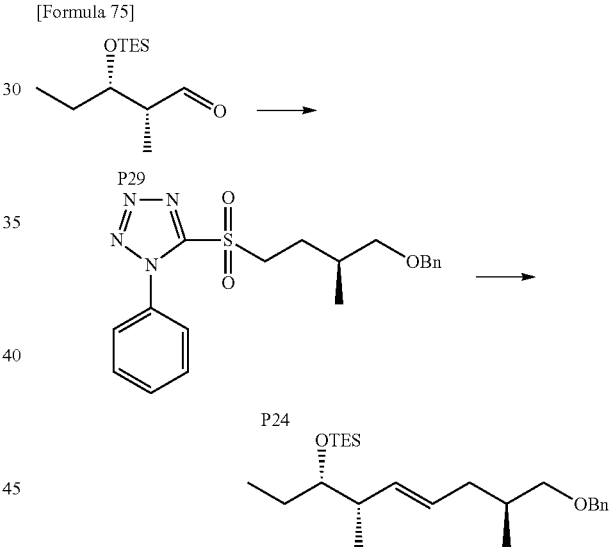

(1) Synthesis of {[(1S,2S,3E,6S)-7-(benzyloxy)-1-ethyl-2,6-dimethylhept-3-en-1-yl]oxy}(triethyl)silane (P30)

This reaction was performed with reference to the literature (Blakemore, P. R.; Cole, W. J.; Kociensky, P. J.; Morley, A., Synlett, 1998, 26-28.).

THF distilled by using lithium aluminum hydride immediately before use was used at this step.

15% toluene solution (0.65 ml) of potassium bis(trimethylsilyl)amide was added dropwise to THF (2 ml) solution of 5{[(3S)-4-(benzyloxy)-3-methylbutyl]sulfonyl}-1-phenyl-1H-tetrazole (100 mg, 0.244 mmol) at −78° C. and it was stirred at the same temperature for one hour. Subsequently a THF (0.5 ml) solution of (2R,3S)-2-methyl-3-[(triethylsilyl)oxy]pentanal (112 mg, 0.49 mmol) was added dropwise to the reaction solution at −78° C. and it was stirred for one hour. After the reaction solution was warmed to room temperature, an appropriate amount of water was added. The reaction solution was diluted with ethyl acetate and washed with brine. After the organic layer after was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:diethyl ether=100:1) to obtain the title compound (66 mg) as a colorless oil.

400 MHz $^1$H-NMR (CDCl$_3$) δ (ppm) 0.60 (q, J=8.0 Hz, 6H), 0.86 (t, J=7.2 Hz, 3H), 0.91 (d, J=6.4 Hz, 3H), 0.94 (d, J=6.8 Hz, 3H), 0.96 (t, J=8.0 Hz, 9H), 1.34-1.49 (m, 2H), 1.78-1.93 (m, 2H), 2.11-2.19 (m, 1H), 2.20-2.27 (m, 1H), 3.24 (dd, J=6.0, 8.8 Hz, 1H), 3.33 (dd, J=6.0, 8.8 Hz, 1H), 3.42 (dt, J=5.2, 5.6 Hz, 1H), 4.49 (s, 2H), 5.31-5.41 (m, 2H), 7.26-7.36 (m, 5H); IR (neat) 3086, 3067, 3033, 2958, 2903, 2879, 1500, 1456, 1102, 1011, 737 cm$^{-1}$; HRMS C$_{24}$H$_{42}$AgO$_2$Si (M+Ag$^+$) Calcd: 497.2005, Found: 497.1981

100 MHz $^{13}$C-NMR (CDCl$_3$) δ (ppm) 5.18, 6.97, 9.35, 16.15, 16.84, 26.81, 33.80, 36.83, 41.73, 72.92, 75.33, 77.44, 127.34, 127.44, 127.48, 128.23, 134.81, 138.77; $[α]_D^{25}$ −16.07 (c 1.28, CHCl$_3$).

[Formula 76]

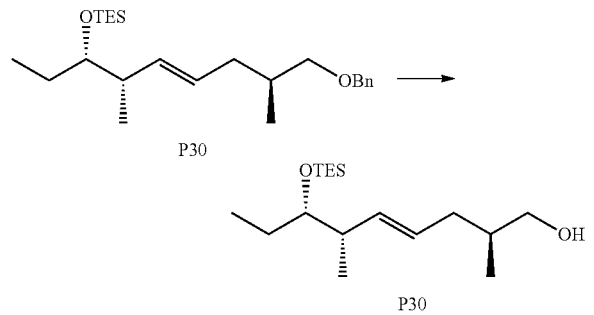

(2) Synthesis of (2S,4E,6S,7S)-2,6-dimethyl-7-[(triethylsilyl)oxy]non-4-en-1-ol (P31)

This reaction was performed with reference to the literature (Shimshock, S. J.; Waltermire, R. E.; DeShong, P., J. Am. Chem. Soc., 1991, 113, 8791-8796.).

Lithium (39.4 mg, 5.62 mmol) was added to a THF (25 ml) solution of di-tert-butyldiphenyl (1.87 g, 7.02 mmol) while ice cooling and the reaction solution was stirred at room temperature for three hours. The reaction solution turned dark green during stirring. This solution was added dropwise to THF (5 ml) solution of {[(1S,2S,3E,6S)-7-benzyloxy-1-ethyl-2,6-dimethylhept-3-en-1-yl]oxy}(triethyl)silane (500 mg, 1.28 mmol) slowly (at such a rate that green of the reaction solution was maintained) cooled to −78° C. under stirring. After the reaction solution was stirred at the same temperature for three hours, a saturated ammonium chloride aqueous solution was added thereto and the mixture was warmed to room temperature. After the reaction solution was diluted with ethyl acetate, it was washed with brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=15:1) to obtain the title compound (296 mg) as a colorless oil.

400 MHz $^1$H-NMR (CDCl$_3$) δ (ppm) 0.60 (q, J=8.0 Hz, 6H), 0.87 (t, J=7.6 Hz, 3H), 0.90 (d, J=6.8 Hz, 3H), 0.95 (d, J=7.6 Hz, 3H), 0.96 (t, J=8.0 Hz, 9H), 1.34-1.50 (m, 2H), 1.65-1.76 (m, 1H), 1.87-1.94 (m, 1H), 2.09 (ddd, 5.6, 5.6, 14.0 Hz, 1H), 2.21-2.29 (m, 1H), 3.42-3.48 (m, 2H), 3.51 (dd, J=6.0, 10.4 Hz, 1H), 5.30-5.46 (m, 2H); IR (neat) 3342, 2958, 2916, 2877, 1459, 1415, 1380, 1013, 741 cm$^{-1}$; HRMS C$_{17}$H$_{36}$AgO$_2$Si (M+Ag$^+$) Calcd: 407.1536, Found: 407.1512

100 MHz $^{13}$C-NMR (CDCl$_3$) δ (ppm) 5.11, 6.90, 9.39, 16.05, 16.37, 26.67, 35.96, 36.69, 41.71, 67.81, 77.46, 127.57, 134.84; $[α]_D^{25}$ −24.74 (c 1.36, CHCl$_3$).

Step 15

Synthesis of (3S,4S,5E,8S)-4,8-dimethyl-9-[(1-phenyl-1H-tetrazol-5-yl)sulfonyl]non-5-en-3-ol

[Formula 77]

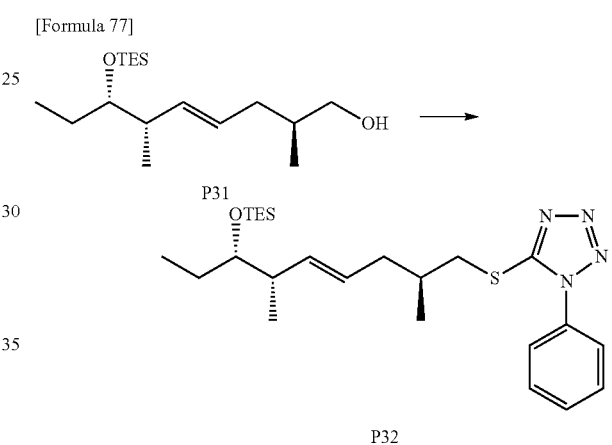

(1) Synthesis of 5-{(2S,4E,6S,7S)-2,6-dimethyl-7-[(triethylsilyl)oxy]non-4-en-1-yl}thio)-1-phenyl-1H-tetrazole (P32)

This reaction was performed with reference to the literature (Mitsunobu, O., Synthesis, 1981, 1-28.).

After 5-mercapto-1-phenyltetrazole (237 mg, 1.33 mmol) and triphenylphosphine (350 mg, 1.33 mmol) were added to a THF (10 ml) solution of (2S,4E,6S,7S)-2,6-dimethyl-7-[(triethylsilyl)oxy]non-4-en-1-ol (334 mg, 1.11 mmol) at room temperature, 40% toluene solution of diethyl azodicarboxylate (0.63 ml, 1.44 mmol) was added dropwise to while ice cooling. After the reaction solution was stirred at room temperature for three hours, it was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=40:1) to obtain the title compound (457 mg) as a colorless oil.

400 MHz $^1$H-NMR (CDCl$_3$) δ (ppm) 0.59 (q, J=8.0 Hz, 6H), 0.85 (t, J=7.6 Hz, 3H), 0.95 (d, J=6.8 Hz, 3H), 0.95 (t, J=8.0 Hz, 9H), 1.03 (d, J=6.0 Hz, 3H), 1.32-1.52 (m, 2H), 1.97-2.06 (m, 2H), 2.18-2.29 (m, 2H), 3.28 (dd, J=6.4, 12.8 Hz, 1H), 3.41-3.45 (m, 2H), 5.32-5.39 (m, 1H), 5.45 (dd, J=7.2, 15.2 Hz, 1H), 7.52-7.60 (m, 5H); IR (neat) 2958, 2883, 1594, 1500, 1459, 1383, 1240, 1013, 742 cm$^{-1}$; HRMS C$_{24}$H$_{41}$N$_{4}$OSSi (M+H$^{+}$) Calcd: 461.2770, Found: 461.2787

100 MHz $^{13}$C-NMR (CDCl$_{3}$) δ (ppm) 5.09, 6.90, 9.40, 16.05, 15.86, 18.80, 26.64, 33.09, 38.84, 39.71, 41.68, 77.29, 123.75, 126.09, 129.66, 129.95, 133.68, 135.96, 154.56; [α]$_{D}$$^{25}$ −22.0 (c 1.51, CHCl$_{3}$).

[Formula 78]

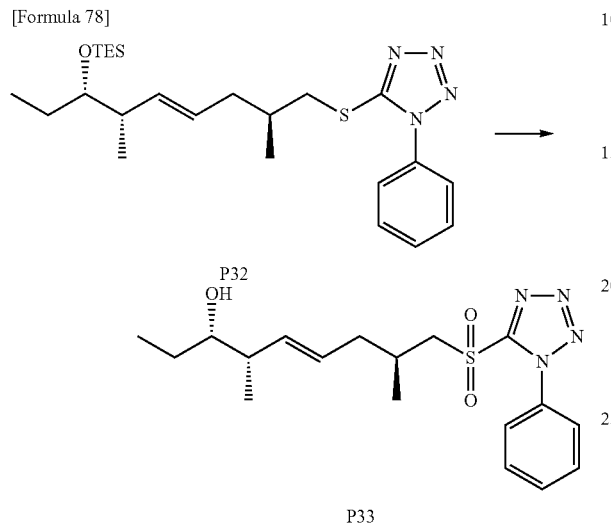

P33

(2) Synthesis of (3S,4S,5E,8S)-4,8-dimethyl-9-[(1-phenyl-1H-tetrazol-5-yl)sulfonyl]non-5-en-3-ol (P33)

This reaction was performed with reference to the literature (Shultz, H. S.; Freyermuth, H. B.; Buc, S. R., J. Org. Chem., 1963, 28(4), 1140-1142.).

About 30% hydrogen peroxide solution (1.29 ml, 11.4 mmol) solution of hexaammonium heptamolybdate tetrahydrate (140 mg, 0.12 mmol) was added to an ethanol (10 ml) solution of 5-{(2S,4E,6S,7S)-2,6-dimethyl-7-[(triethylsilyl)oxy]non-4-en-1-yl}thio)-1-phenyl-1H-tetrazole (444 mg, 1.14 mmol) at room temperature and the reaction solution was stirred for 24 hours. The reaction solution was diluted with ethyl acetate and washed with water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=5:1-1:1) to obtain the title compound (300 mg) as a colorless oil. (The title compound crystallized from hexane-ethyl acetate.)

400 MHz $^{1}$H-NMR (CDCl$_{3}$) δ (ppm) 0.95 (t, J=7.3 Hz, 3H), 1.01 (d, J=6.8 Hz, 3H), 1.16 (d, J=6.6 Hz, 3H), 1.31-1.42 (m, 1H), 1.42-1.49 (m, 1H), 1.49-1.59 (m, 1H), 2.20 (dd, J=6.2, 6.4 Hz, 2H), 2.23-2.31 (m, 1H), 2.37-2.47 (m, 1H), 3.34-3.42 (m, 1H), 3.53 (dd, J=7.4, 14.5 Hz, 1H), 3.88 (dd, J=4.8, 14.5 Hz, 1H), 5.39-5.47 (m, 1H), 5.50 (dd, J=7.2, 15.6 Hz, 1H), 7.57-7.70 (m, 5H); 100 MHz $^{13}$C-NMR (CDCl$_{3}$) δ (ppm) 10.24, 14.79, 19.60, 26.92, 28.25, 39.35, 42.14, 60.73, 76.35, 125.02, 126.09, 129.55, 131.34, 132.92, 137.02, 153.88; IR (KBr) 3384, 3351, 3316, 2961, 2939, 2879, 2356, 2338, 1593, 1499, 1459, 1332, 1156, 1098, 1019, 967, 840, 768, 691, 633 cm$^{-1}$; HRMS C$_{18}$H$_{27}$N$_{4}$O$_{3}$S (M+H$^{+}$) Calcd: 379.1804, Found: 379.1806; [α]$_{D}$$^{23}$ −29.5 (c 1.20, CHCl$_{3}$)

Step 16

Synthesis of 5-({(2S)-3-[(2R,3R)-3-((1S,2S)-2-{[diethyl(isopropyl)silyl]oxy}-1-methylbutyl)oxiran-2-yl]-2-methylpropyl}sulfonyl)-1-phenyl-1H-tetrazole)

[Formula 79]

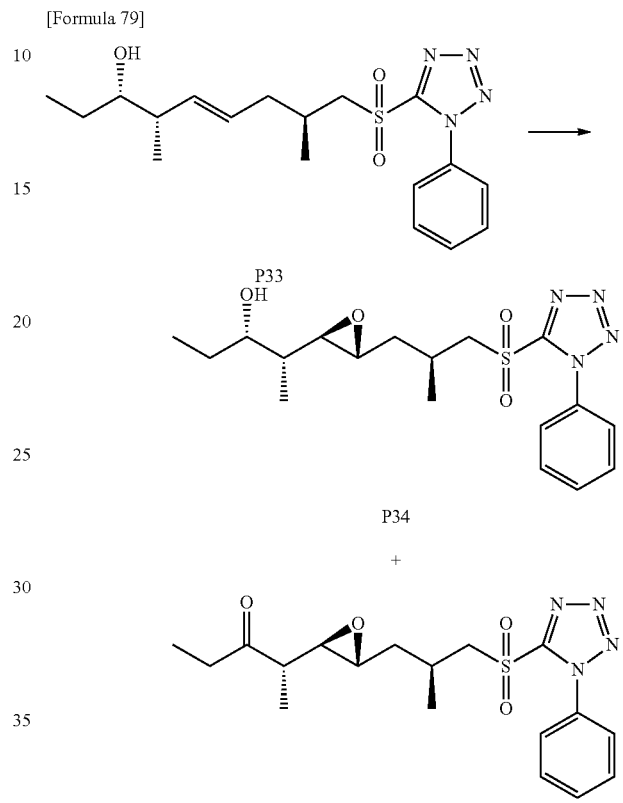

(1) Synthesis of (2R,3S)-2-((2R,3R)-3-{(2S)-2-methyl-3-[(1-phenyl-1H-tetrazol-5-yl)sulfonyl]propyl}oxiran-2-yl)pentane-3-ol (P34)

This reaction was performed with reference to the literature (Wang, Z., -X.; Tu, Y.; Frohn, M.; Zhang, J.-R.; Shi, Y., J. Am. Chem. Soc., 1997, 119, 11224-11235. Wang, Z., -X.; Tu, Y.; Frohn, M.; Zhang, J.-R.; Shi, Y., J. Org. Chem., 1997, 62, 2328-2329.).

(3S,4S,5E,8S)-4,8-dimethyl-9-[(1-phenyl-1H-tetrazol-5-yl)sulfonyl]non-5-en-3-ol (190 mg, 0.50 mmol) was dissolved in acetonitrile (7.5 ml) and 0.05M sodium tetraborate decahydrate −0.4 mM disodium ethylenediaminetetraacetate salt solution (5 ml). 1,2:4,5-di-O-isopropylidene-D-erythro-2,3-hexodiuro-2,6-pyranose (450 mg, 1.74 mmol) was added while ice cooling. Subsequently, a mixed powder of potassium carbonate (0.85 mg, 6.16 mmol) and oxone (1.27 g, 2.06 mmol) was added at the same temperature over one hour. The reaction solution was stirred at the same temperature for further one hour. The reaction solution was diluted with ethyl acetate and washed with water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=3:1) to obtain the title compound (160 mg, 94% ee) as a colorless oil.

The optical purity was determined by HPLC using a chiral column (DAICEL, commercial name CHIRALCEL OD; n-hexane:isopropylalcohol=75:25).

This oil was crystallized from hexane at −78° C. and recrystallized further from a mixed solvent of hexane-ethyl acetate and the title compound (140 mg, >99% ee) was obtained as a colorless prism. In addition, (2S)-2-((2R,3R)-3-{(2S)-2-methyl-3-[(1-phenyl-1H-tetrazol-5-yl)sulfonyl]propyl}oxiran-2-yl)pentan-3-one (P34b, 34 mg) was obtained as colorless oil, as a by-product of this procedure.

Compound P34: 400 MHz $^1$H-NMR (CD$_3$OD) δ (ppm) 0.98 (d, J=7.1 Hz, 3H), 0.99 (t, J=7.3 Hz, 3H), 1.26 (d, J=6.8 Hz, 3H), 1.29-1.37 (m, 1H), 1.45-1.63 (m, 3H), 1.89 (ddd, J=4.6, 5.8, 14.3 Hz, 1H), 2.45-2.57 (m, 1H), 2.69 (dd, J=2.2, 7.9 Hz, 1H), 2.86 (ddd, J=2.2, 4.6, 6.9 Hz, 1H), 3.57 (dt, J=4.6, 8.8 Hz, 1H), 3.69 (dd, J=7.3, 14.8 Hz, 1H), 3.91 (dd, J=5.2, 14.8 Hz, 1H), 7.66-7.77 (m, 5H); 100 MHz $^{13}$C-NMR (CD$_3$OD) δ (ppm) 10.54, 10.87, 20.29, 28.32, 28.57, 39.26, 42.23, 56.63, 61.67, 62.23, 75.15, 126.94, 130.58, 132.54, 134.54, 155.41; IR (KBr) 3336, 3245, 2961, 2925, 2900, 2869, 1779, 1594, 1460, 1334, 1154, 1109, 1071, 981, 955, 828, 765, 688, 634, 524, 456 cm$^{-1}$; HRMS C$_{18}$H$_{27}$N$_4$O$_4$S (M+H$^+$) Calcd: 395.1753, Found: 395.1721; [α]$_D^{20}$ −21.0 (c 1.00, CH$_3$OH)

Compound P34b: 400 MHz $^1$H-NMR (CDCL$_3$) δ (ppm) 1.03 (t, J=7.3 Hz, 3H), 1.12 (d, J=7.1 Hz, 3H), 1.28 (d, J=6.9 Hz, 3H), 1.56 (ddd, J=7.4, 7.4, 14.8 Hz, 1H), 1.96 (ddd, J=4.6, 5.8, 14.8 Hz, 1H), 2.31-2.45 (m, 1H), 2.45-2.65 (m, 3H), 2.75-2.83 (m, 2H), 3.65 (dd, J=7.1, 14.6 Hz, 1H), 3.93 (dd, J=5.3, 14.6 Hz, 1H), 7.56-7.71 (m, 5H); 100 MHZ $^{13}$C-NMR (CD$_3$OD) δ (ppm) 7.74-12.93, 20.33, 28.30, 36.12, 39.00, 49.48, 56.62, 60.05, 62.22, 127.03, 130.62, 132.60, 134.63, 155.47, 214.55; HRMS; C$_{18}$H$_{25}$N$_4$O$_4$S$^+$ Calcd: 393.1597, Found: 393.1601 (M+H)$^+$; [α]$_D^{24}$ +52.25 (c 0.86, CH$_3$OH).

3-ol (200 mg, 0.507 mmol) at room temperature, and the mixture was stirred at the same temperature for one hour. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=20:1→10:1) to obtain the title compound (265 mg) as a colorless oil.

400 MHz $^1$H-NMR (CD$_3$OD) δ (ppm) 0.67-0.74 (m, 4H), 0.88 (t, 3H), 0.95 (d, J=6.8 Hz, 3H), 0.90-0.98 (m, 1H), 1.04 (t, J=7.6 Hz, 3H), 1.05 (t, J=7.6 Hz, 3H), 1.06 (d, J=5.6 Hz, 6H), 1.26 (d, J=6.8 Hz, 3H), 1.32-1.43 (m, 1H), 1.52-1.63 (m, 3H), 1.92 (ddd, J=4.4, 6.0, 14.0 Hz, 1H), 2.45-2.56 (m, 1H), 2.71 (dd, J=2.4, 7.6 Hz, 1H), 2.86 (ddd, J=2.4, 4.4, 6.8 Hz, 1H), 3.70 (dd, J=7.6, 14.8 Hz, 1H), 3.80-3.86 (m, 1H), 3.90 (dd, J=5.2, 14.8 Hz, 1H), 7.65-7.75 (m, 5H); 100 MHz $^{13}$C-NMR (CD$_3$OD) δ (ppm) 5.00, 5.17, 7.65, 10.02, 10.11, 14.40, 17.93, 20.31, 28.46, 28.64, 39.40, 40.84, 57.28, 61.58, 62.28, 75.78, 126.99, 130.63, 132.58, 134.71, 155.54; IR (neat) 2961, 2881, 1596, 1498, 1462, 1339, 1153, 1014, 823, 763, 723, 633 cm$^{-1}$; HRMS C$_{25}$H$_{43}$N$_4$O$_4$SSi (M+H$^+$) Calcd: 523.2774, Found: 523.2766; [α]$_D^{23}$ +19.3 (c 1.09, CH$_3$OH)

Step 17

Synthesis of 6,7-O—[(S)-benzylidene]pladienolide A

[Formula 81]

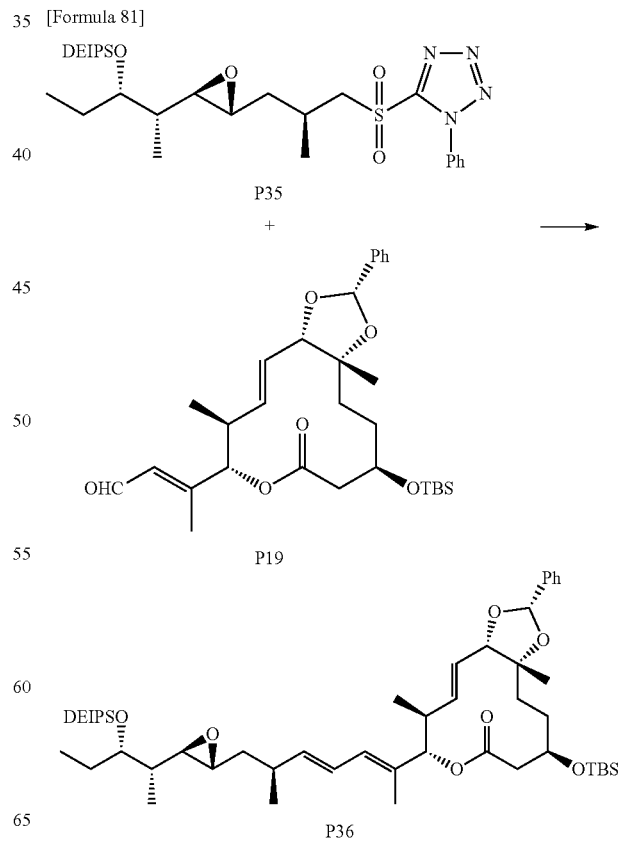

[Formula 80]

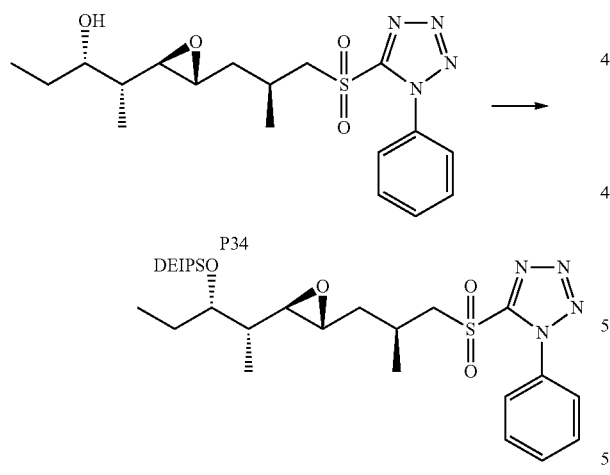

(2) Synthesis of 5-({(2S)-3-[(2R,3R)-3-(1S,2S)-2-{[diethyl(isopropyl)silyl]oxy-1-methylbutyl}oxiran-2-yl}-2-methylpropyl}sulfonyl)-1-phenyl-1H-tetrazole (P35)

Imidazole (345 mg, 5.07 mmol) and diethylisopropylsilyl chloride (418 mg, 2.54 mmol) were added to a DMF (4 ml) solution of (2R,3S)-2-((2R,3R)-3-{(2S)-2-methyl-3-[(1-phenyl-1H-tetrazol-5-yl)sulfonyl]propyl}oxiran-2-yl)pentane-

(1) Synthesis of 6,7-O—[(S)-benzylidene]-3-{[tert-butyl(dimethyl)silyl]oxy}-21-{[diethyl(isopropyl)silyl]oxy}-pladienolide A (36)

This reaction was performed with reference to the literature (Blakemore, P. R.; Cole, W. J.; Kociensky, P. J.; Morley, A., Synlett, 1998, 26-28.).

THF distilled by using lithium aluminum hydride immediately before use was used at this step.

15% toluene solution (0.317 ml) of potassium bis(trimethylsilyl)amide was added dropwise to a THF (1 ml) solution of 5-({(2S)-3-[(2R,3R)-3-(1S,2S)-2-{[diethyl(isopropyl)silyl]oxy-1-methylbutyl)oxiran-2-yl}-2-methylpropyl}sulfonyl)-1-phenyl-1H-tetrazole (62 mg, 0.119 mmol) at −78° C. under stirring and it was stirred at the same temperature for 30 minutes. A THF (1 ml) solution of (2E)-3-((2S,3aS,4E,6S,7S,13aR)-11-{[tert-butyl(dimethyl)silyl]oxy}-6,13a-dimethyl-9-oxo-2-phenyl-6,7,9,10,11,12,13,13a-octahydro-3aH-[1,3]dioxolo[4,5-f]oxacyclododecin-7-yl)but-2-enal (94 mg, 0.179 mmol) was added dropwise to this reaction solution at −78° C. and stirred at the same temperature for one hour. The reaction solution was warmed to room temperature and diluted with ethyl acetate after addition of an appropriate amount of water and washed with brine. After the organic layer was dried over anhydrous sodium sulfate and the drying agent was filtered off, the organic layer was concentrated under reduced pressure. The obtained residue was purified by silica gel column chromatography (Kanto, Silica Gel 60N, 40-100 μm; heptane:ethyl acetate=25:1-15:1) to obtain the title compound (65 mg) as a colorless oil.

400 MHz $^1$H-NMR (CD$_3$OD) δ (ppm) 0.15 (s, 3H), 0.17 (s, 3H), 0.66-0.75 (m, 4H), 0.86 (t, J=7.6 Hz, 3H), 0.90 (d, J=6.8 Hz, 3H), 0.93 (d, J=6.8 Hz, 3H), 0.95 (s, 9H), 0.94-1.03 (m, 1H), 1.05 (t, J=8.4 Hz, 6H), 1.07 (d, J=6.4 Hz, 6H), 1.12 (d, J=6.8 Hz, 3H), 1.24-1.35 (m, 1H), 1.38-1.50 (m, 3H), 1.42 (s, 3H), 1.58 (dq, J=7.6, 14.4 Hz, 2H), 1.69-1.78 (m, 2H), 1.78 (s, 3H), 1.96-2.05 (m, 1H), 2.28 (dd, J=10.2, 14.8 Hz, 1H), 2.44-2.58 (m, 1H), 2.64-2.72 (m, 3H), 2.76 (dt, J=2.4, 6.0 Hz, 1H), 3.80-3.86 (m, 1H), 4.05-4.13 (m, 1H), 4.28 (d, J=9.6 Hz, 1H), 4.96 (d, J=10.8 Hz, 1H), 5.50 (dd, J=9.6, 15.2 Hz, 1H), 5.68 (dd, J=9.6, 14.4 Hz, 1H), 5.70 (dd, J=9.6, 15.2 Hz, 1H), 5.94 (s, 1H), 6.12 (d, 10.8 Hz, 1H), 6.36 (dd, J=10.8, 14.4 Hz, 1H), 7.40-7.44 (m, 3H), 7.52-7.54 (m, 2H); 100 MHz $^{13}$C-NMR (CD$_3$COCD$_3$) δ (ppm) −4.94, −4.85, 4.06, 4.24, 7.02, 7.05, 9.44, 9.76, 11.17, 13.33, 16.70, 17.32, 17.92, 21.07, 22.61, 25.64, 27.74, 31.69, 34.80, 35.51, 40.00, 40.08, 40.19, 44.08, 56.95, 60.92, 71.89, 74.66, 82.34, 83.54, 85.35, 101.21, 124.75, 127.09, 128.24, 129.11, 130.29, 130.76, 131.79, 137.63, 139.00, 141.19, 168.35; IR (neat)=2959, 1732, 1462, 1376, 1276, 1247, 1064, 1008, 971, 881, 836, 775, 760, 722, 564, 536, 463 cm$^{-1}$; HRMS C$_{48}$H$_{80}$NaO$_7$Si$_2$ (M+Na$^+$) Calcd: 847.5340, Found: 847.5323.; [α]$_D^{26}$ +21.3 (c 1.09, CH$_2$Cl$_2$)

[Formula 82]

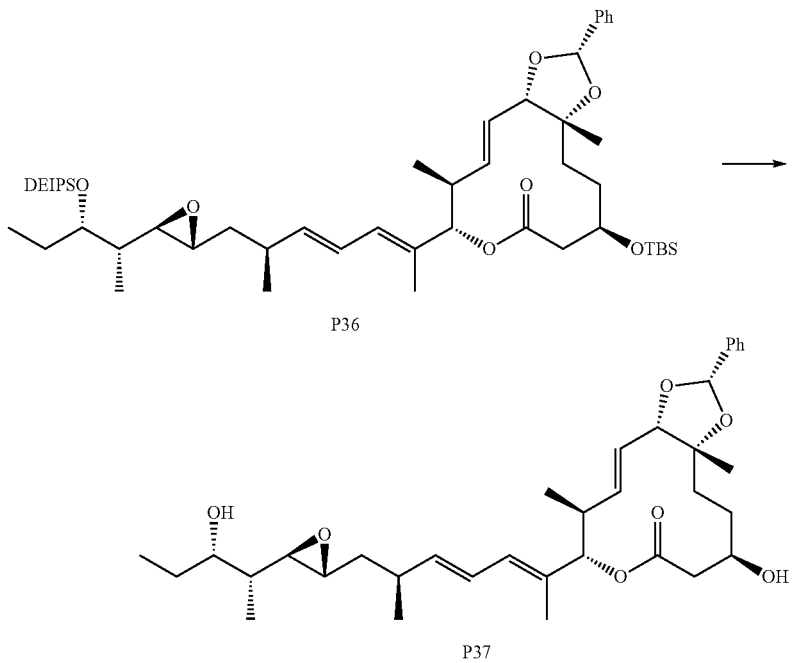

(2) Synthesis of 6,7-O—[(S)-benzylidene]pladienolide A (P37)

1M THF solution (3.80 ml, 696 μmol) of tetra-n-butylammonium fluoride (3.80 ml, 696 μmol) was added to a THF (3.80 ml) solution of 6,7-O—[(S)-benzylidene]-3-{[tert-butyl(dimethyl)silyl]oxy}-21-{[diethyl(isopropyl)silyl]oxy}-pladienolide A (191 mg, 232 μmol) at room temperature. The reaction solution was stirred at room temperature for one and a half hour. The reaction solution was poured into a saturated ammonium chloride aqueous solution, which was then extracted with ethyl acetate. The organic layer was washed with water and brine sequentially and dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:ethyl acetate=2:1→1:1) to obtain the title compound (135 mg) as a colorless oil.

400 MHz $^1$H-NMR (CD$_3$OD) δ (ppm) 0.93 (d, J=7.2 Hz, 3H), 0.94 (d, J=7.2 Hz, 3H), 0.98 (t, J=7.4 Hz, 3H), 1.13 (d, J=6.8 Hz, 3H), 1.18-1.29 (m, 1H), 1.44 (s, 3H), 1.44-1.60 (m, 6H), 1.64-1.72 (m, 1H), 1.79 (d, J=1.2 Hz, 3H), 2.00-2.10 (m, 1H), 2.33 (dd, J=9.8, 14.6 Hz, 1H), 2.46-2.56 (m, 1H), 2.62-2.78 (m, 3H), 3.55 (dt, J=4.8, 8.0 Hz, 1H), 3.93-4.01 (m, 1H), 4.28 (d, J=9.2 Hz, 1H), 4.97 (d, J=10.4 Hz, 1H), 5.49 (dd, J=9.6, 14.8 Hz, 1H), 5.69 (dd, J=9.2, 14.8 Hz, 2H), 5.94 (s, 1H), 6.13 (brd, J=11.0 Hz, 1H), 6.36 (dd, J=11.0, 14.8 Hz, 1H), 7.40-7.43 (m, 3H), 7.51-7.34 (m, 2H); 100 MHz $^{13}$C-NMR (CD$_3$COCD$_3$) δ (ppm) 10.20, 10.30, 11.26, 16.48, 20.87, 22.33, 27.88, 31.04, 34.09, 35.51, 39.80, 40.20, 41.53, 42.71, 56.45, 61.31, 70.01, 73.62, 82.39, 83.66, 85.21, 101.20, 124.65, 127.09, 128.30, 129.14, 130.49, 130.86, 131.74, 137.37, 139.11, 141.32, 169.85; IR (neat) 3502, 2965, 2931, 2874, 1711, 1456, 1377, 1246, 1221, 1178, 1092, 1064, 971, 761 cm$^{-1}$; HRMS C$_{35}$H$_{50}$NaO$_7$ (M+Na$^+$) Calcd: 605.3454, Found: 605.3449; [α]$_D^{24}$ −13.0 (c 1.05, CH$_2$Cl$_2$)

Step 18

Synthesis of Pladienolide A solution was stirred at 0° C. for 40 minutes, 4-dimethylaminopyridine (15 mg, 123 μmol) was added thereto and the mixture was stirred at 0° C. for further one and a half hour. The reaction solution was poured into water, which was then extracted with ethyl acetate. The organic layer was washed with water and brine sequentially and dried over anhydrous magnesium sulfate. After the drying agent was filtered off, the organic layer was concentrated under reduced pressure. The obtained residue was purified by silica gel column chromatography (Merck, commercial name Silica Gel 60, 230-400 mesh; n-heptane:ethyl acetate=8:1→6:1→4:1) to obtain the title compound (198 mg) as a yellow oil.

400 MHz $^1$H-NMR (CDCl$_3$) δ (ppm) 0.88 (d, J=6.8 Hz, 3H), 0.93 (t, J=7.6 Hz, 3H), 0.95 (d, J=6.8 Hz, 3H), 1.07 (d, J=6.8 Hz, 3H), 1.41 (s, 3H), 1.46-1.60 (m, 3H), 1.62-1.68 (m, 1H), 1.68-1.81 (m, 4H), 1.73 (s, 3H), 1.94-2.05 (m, 1H), 2.40-2.56 (m, 3H), 2.56-2.78 (m, 2H), 2.83 (dd, J=4.2, 15.0 Hz, 1H), 4.21 (d, J=9.2 Hz, 1H), 4.92 (d, J=10.4 Hz, 1H), 5.02-5.08 (m, 1H), 5.12-5.22 (m, 1H), 5.42 (dd, J=9.6, 15.2 Hz, 1H), 5.62 (dd, J=8.4, 14.8 Hz, 1H), 5.67 (dd, J=9.6, 15.2 Hz, 1H), 5.92 (s, 1H), 5.93 (s, 1H), 5.96 (s, 1H), 6.09 (d, J=10.8 Hz, 1H), 6.24 (dd, J=10.8, 14.8 Hz, 1H), 7.37-7.42 (m, 3H), 7.49-7.52 (m, 2H); 100 MHz $^{13}$C-NMR (CDCl$_3$) δ (ppm) 9.62, 10.96, 11.73, 16.48, 21.04, 22.62, 24.79, 27.87,

[Formula 83]

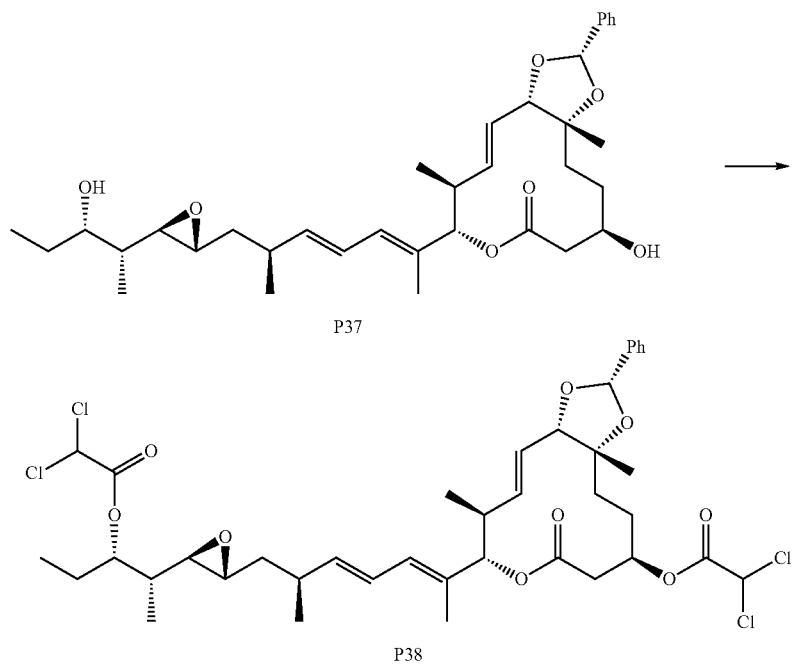

(1) Synthesis of 6,7-O—[(S)-benzylidene]-3,21-bis (dichloroacetyl) pladienolide A (P38)

Triethylamine (686 μl, 4.92 mmol), dichloroacetic anhydride (375 μl, 2.46 mmol) and 4-dimethylaminopyridine (15 mg, 123 μmol) were added to anhydrous dichloromethane (7.20 ml) solution of 6,7-O-[(S)-benzylidene]pladienolide A (144 mg, 2.46 mmol) under stirring at 0° C. After the reaction 32.99, 35.31, 38.87, 39.30, 39.55, 40.13, 56.41, 60.03, 64.14, 64.58, 75.78, 80.54, 83.02, 83.19, 85.06, 101.26, 124.45, 126.61, 128.33, 129.31, 129.64, 130.86, 131.04, 137.44, 137.74, 141.03, 164.06, 167.56; IR (neat) 3015, 2972, 2931, 2877, 1759, 1739, 1576, 1457, 1377, 1281, 1248, 1171, 1092, 1066, 1004, 968, 911, 816, 758, 699 cm$^{-1}$; HRMS C$_{39}$H$_{50}$Cl$_4$O$_9$Na (M+Na$^+$) Calcd: 825.2107, Found: 825.2120; [α]$_D^{23}$+15.0 (c 1.02, CH$_2$Cl$_2$)

[Formula 84]

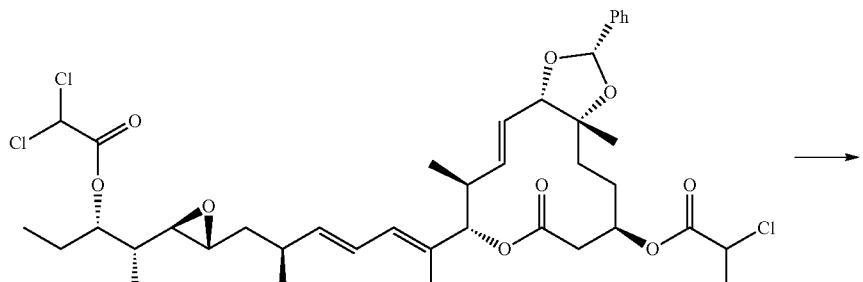

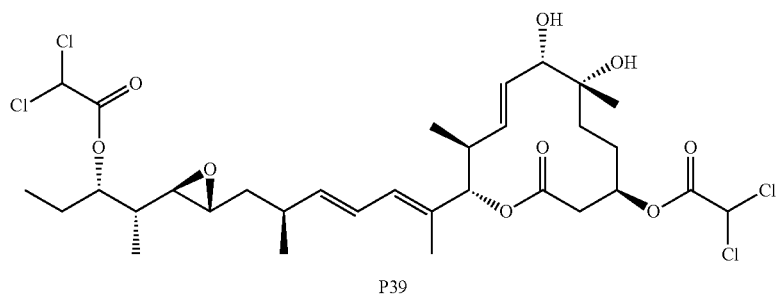

(2) Synthesis of 3,21-bis(dichloroacetyl) pladienolide A (24)

Pyridinium p-toluenesulfonate (70.5 mg, 280 μmol) was added to a methanol (4.48 ml) solution of 6,7-O—[(S)-benzylidene]-3,21-bis(dichloroacetyl pladienolide A (112 mg, 140 μmol) at room temperature. The reaction solution was stirred at room temperature for 46 hours. The reaction solution was poured into brine, which was then extracted with ethyl acetate. The organic layer was washed with water and brine sequentially and dried over anhydrous magnesium sulfate. After the drying agent was filtered off, the organic layer was concentrated under reduced pressure. The obtained residue was purified by silica gel column chromatography (Merck, commercial name Silica Gel 60, 230-400 mesh; n-heptane:ethyl acetate=8:1→6:1→3:1→3:2→1:1) to obtained title compound (32.2 mg) as a colorless oil while 6,7-O—[(S)-benzylidene]-3,21-bis(dichloroacetyl) pladienolide A (55.9 mg) was recovered.

400 MHz $^1$H-NMR (CDCl$_3$) δ (ppm) 0.90 (d, J=7.2 Hz, 3H), 0.93 (t, J=7.2 Hz, 3H), 0.96 (d, J=7.2 Hz, 3H), 1.06 (d, J=6.8 Hz, 3H), 1.32 (s, 3H), 1.43-1.62 (m, 5H), 1.63-1.69 (m, 2H), 1.72 (s, 3H), 1.72-1.79 (m, 2H), 2.00 (brs, 1H), 2.41-2.48 (m, 1H), 2.51-2.58 (m, 3H), 2.61 (dd, J=3.2, 15.2 Hz, 1H), 2.66-2.70 (m, 1H), 2.74 (dd, J=4.0, 15.2 Hz, 1H), 3.80 (dd, J=2.6, 9.8 Hz, 1H), 4.93-4.97 (m, 1H), 5.01-5.05 (m, 1H), 5.05 (d, J=10.4 Hz, 1H), 5.47 (dd, J=9.8, 15.3 Hz, 1H), 5.61 (dd, J=8.0, 15.1 Hz, 1H), 5.74 (dd, J=9.6, 15.3 Hz, 1H), 5.97 (s, 1H), 5.98 (s, 1H), 6.07 (brd, J=10.4 Hz, 1H), 6.24 (dd, J=10.4, 15.1 Hz, 1H); 100 MHz $^{13}$C-NMR (CDCl$_3$) δ (ppm) 9.68, 11.00, 11.77, 16.51, 21.08, 24.60, 24.83, 25.61, 34.76, 35.35, 36.17, 39.34, 39.61, 40.47, 56.48, 60.07, 64.27, 64.61, 73.28, 74.59, 80.60, 83.08, 124.52, 129.71, 130.86, 131.11, 137.79, 141.06, 163.91, 164.17, 168.05; IR (neat) 3526, 2971, 2929, 1759, 1745, 1456, 1377, 1281, 1217, 1171, 1092, 1008, 964, 927, 816, 757 cm$^{-1}$; HRMS C$_{32}$H$_{46}$Cl$_4$NaO$_9$ (M+Na$^+$) Calcd: 737.1794, Found: 737.1778; [α]$_D^{27}$ +22.5 (c 1.52, CHCl$_3$)

[Formula 85]

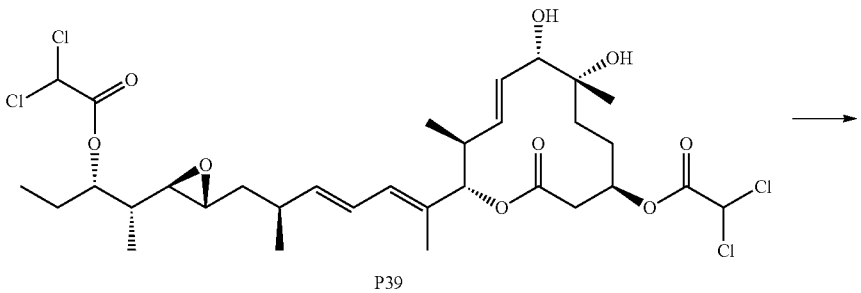

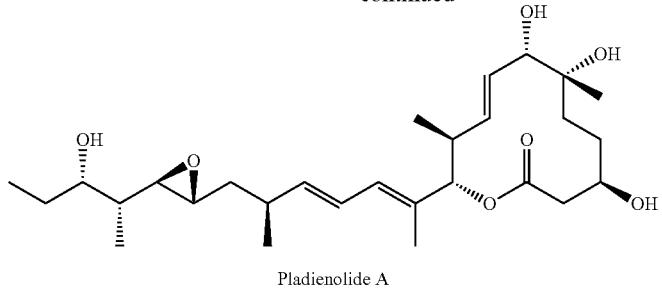

Pladienolide A (3) Synthesis of pladienolide A

Potassium carbonate (13.5 mg, 97.5 μmol) was added to a methanol (2.50 ml) solution of 3,21-bis(dichloroacetyl) pladienolide A (69.9 mg, 97.5 μmol) at room temperature. After the reaction solution was stirred at room temperature for 20 minutes, it was poured into brine, which was then extracted with ethyl acetate. After the organic layer was dried over anhydrous sodium sulfate and the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:acetone=3:2→1:1) to obtain the title compound (46.2 mg) as a colorless oil. This was obtained as a white amorphous by purifying by HPLC (Shiseido, commercial name CAPCELL PAK C18SG120; acetonitrile:water=37:63) followed by performing lyophilization.

600 MHz $^1$H-NMR (CD$_3$OD) δ (ppm) 0.95 (d, J=7.0 Hz, 3H), 0.95 (d, J=6.7 Hz, 3H), 0.98 (t, J=7.4 Hz, 3H), 1.13 (d, J=6.8 Hz, 3H), 1.24 (m, 1H), 1.31 (s, 3H), 1.38 (m, 2H), 1.50 (m, 1H), 1.53 (m, 2H), 1.57 (m, 1H), 1.61 (m, 1H), 1.68 (ddd, J=5.5, 5.9, 14.0 Hz, 1H), 1.79 (brs, 3H), 2.52 (m, 1H), 2.56 (m, 2H), 2.61 (ddq, J=7.0, 9.8, 10.7 Hz, 1H), 2.70 (dd, J=2.2, 8.2 Hz, 1H), 2.77 (ddd, J=2.2, 5.9, 5.9 Hz, 1H), 3.56 (ddd, J=4.5, 4.5, 8.7 Hz, 1H), 3.74 (d, J=9.8 Hz, 1H), 3.81 (m, 1H), 5.07 (d, J=10.7 Hz, 1H), 5.42 (dd, J=9.8, 15.0 Hz, 1H), 5.70 (dd, J=8.4, 15.0 Hz, 1H), 5.76 (dd, J=9.8, 15.0 Hz, 1H), 6.13 (brd, J=10.8 Hz, 1H), 6.37 (dd, J=10.8, 15.0 Hz, 1H); 150 MHz $^{13}$C-NMR (CD$_3$OD) δ (ppm) 10.8, 10.9, 11.9, 17.1, 21.7, 24.4, 28.6, 30.5, 36.7, 37.6, 40.1, 40.7, 1.8, 42.8, 58.5, 63.0, 70.7, 74.7, 75.3, 78.2, 84.4, 125.9, 131.6, 132.1, 132.6, 137.7, 142.3, 171.9; IR (KBr) 3403, 2966, 2935, 2876, 1708, 1458, 1371, 1256, 1177, 1060, 1021, 977, 903, 789 cm$^{-1}$; HRMS C$_{28}$H$_{46}$NaO$_7$ (M+Na$^+$) Calcd: 517.3141, Found: 517.3134; [α]$_D^{27}$ −1.54 (c 1.02, MeOH)

Step 19

Synthesis of Pladienolide B

[Formula 86]

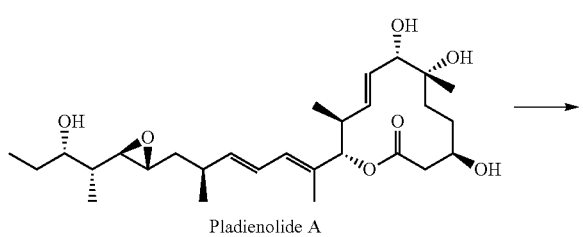

Pladienolide A

→

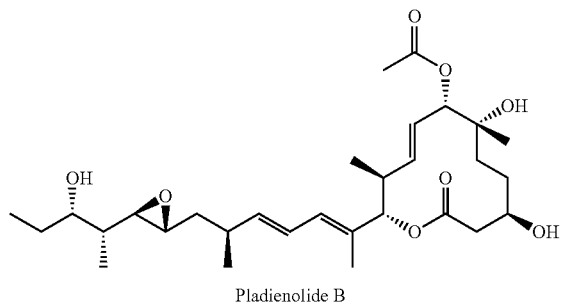

Pladienolide B

Triethylamine (17.2 μl, 123 μmol), acetic anhydride (5.83 μl, 616 μmol) and 4-dimethylaminopyridine (1.50 mg, 12.3 μmol) were added to anhydrous dichloromethane (2.00 ml) solution of pladienolide A (30.5 mg, 61.6 μmol) under stirring at 0° C. After the reaction solution was stirred at 0° C. for one hour, it was poured into a saturated sodium hydrogen carbonate aqueous solution, which was then extracted with ethyl acetate. After the organic layer was washed with brine, it was dried over anhydrous magnesium sulfate. After the drying agent was filtered off, the organic layer was concentrated under reduced pressure. The obtained residue was purified by silica gel column chromatography (Kanto Chemical, commercial name Silica gel 60N, granular, neutral, 0.040 mm-0.100 mm; n-heptane:acetone=3:1→2:1) to obtain the title compound (27.2 mg) as a colorless oil. This was obtained as a white amorphous by purifying by HPLC (Shiseido, commercial name CAPCELL PAK C18SG120; acetonitrile:water=45:55) followed by performing lyophilization.

600 MHz $^1$H-NMR (CD$_3$OD) δ (ppm) 0.93 (d, J=6.8 Hz, 3H), 0.95 (d, J=7.0 Hz, 3H), 0.98 (t, J=7.4 Hz, 3H), 1.13 (d, J=6.8 Hz, 3H), 1.23 (s, 3H), 1.24 (m, 1H), 1.41 (m, 1H), 1.42 (m, 1H), 1.51 (m, 1H), 1.53 (m, 2H), 1.61 (m, 1H), 1.67 (m, 1H), 1.68 (m, 1H), 1.79 (brs, 3H), 2.10 (s, 3H), 2.52 (m, 1H), 2.57 (m, 2H), 2.61 (ddq, J=6.8, 9.9, 10.1 Hz, 1H), 2.70 (dd, J=2.2, 8.2 Hz, 1H), 2.77 (ddd, J=2.2, 5.9, 5.9 Hz, 1H), 3.55 (ddd, J=4.5, 4.5, 8.7 Hz, 1H), 3.82 (m, 1H), 5.09 (d, J=9.8 Hz, 1H), 5.09 (d, J=10.1 Hz, 1H), 5.61 (dd, J=9.9, 15.2 Hz, 1H), 5.70 (dd, J=8.4, 15.0 Hz, 1H), 5.74 (dd, J=9.8, 15.2 Hz, 1H), 6.13 (brd, J=10.8 Hz, 1H), 6.37 (dd, J=10.8, 15.0 Hz, 1H); 150 MHz $^{13}$C-NMR (CD$_3$OD) δ (ppm) 10.8, 10.9, 11.9, 16.9, 21.1, 21.7, 24.2, 28.6, 30.4, 31.1, 36.7, 37.5, 40.1, 40.7, 41.7, 42.8, 58.5, 63.0, 70.4, 74.1, 75.3, 80.3, 84.3, 125.8, 127.0, 132.2, 132.4, 141.6, 142.3, 171.8, 172.2; IR (KBr) 3447, 2966, 2935, 2875, 1735, 1720, 1458, 1372, 1244, 1175, 1022, 978, 910, 551, 478 cm$^{-1}$; HRMS $C_{30}H_{48}NaO_8$ (M+Na$^+$) Calcd: 559.3247, Found: 559.3227; $[\alpha]_D^{27}$ +7.90 (c 1.10, MeOH)

Synthesis of a Compound Analogous to Pladienolide B

[Formula 87]

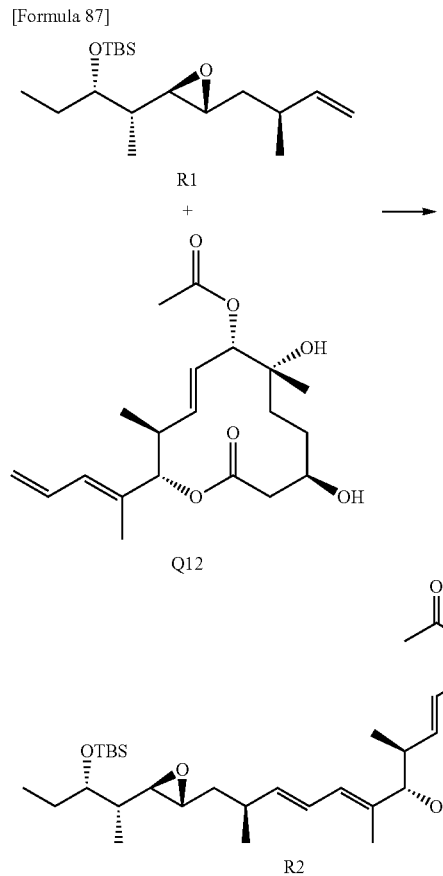

Synthesis of 21-{[tert-butyl(dimethyl)silyl]oxy}pladienolide B (R2)

This reaction is performed with reference to the literature (Grubbs, R. H. "Hand book of Metathesis", Wiley-VCH, 2003, v. 2, p 246-292).

(i) (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate (11.0 mg, 30.0 µmol) and tert-butyl[((1S, 2S)-1-ethyl-2{(2R,3R)-3-[(2S)-2-methylbut-3-en-1-yl]oxiran-2-yl]propyl)oxy}dimethylsilane (24.0 mg 76.8 µmol) were dissolved in anhydrous dichloromethane under argon atmosphere and the second generation Grubbs catalyst; [1,3-bis-(2,4,6-trimethylphenyl)-2-imidazolidinylidene]dichloro(phenylmethylene)-tricyclohexylphosphine)ruthenium was added. The reaction solution was heated to reflux for three hours. After the reaction solution was cooled to room temperature, it was concentrated under reduced pressure. The obtained residue was purified by silica gel column chromatography (Kanto, commercial name Silica Gel 60N, 40-100 µm; heptane:ethyl acetate=1:1) to obtain the title compound (5.1 mg) as a colorless amorphous.

400 MHz $^1$H-NMR (CD$_3$OD) δ (ppm) 0.12 (s, 6H), 0.86 (t J=7.6 Hz, 3H), 0.90 (d, J=7.2 Hz, 3H), 0.92 (d, J=7.6 Hz, 3H), 0.95 (s, 9H), 1.12 (d, J=6.8 Hz, 3H), 1.23 (s, 3H), 1.22-1.78 (m, 9H), 1.78 (s, 3H), 2.10 (s, 3H), 2.46-2.64 (m, 4H), 2.66 (dd, J=2.4, 8.8 Hz, 1H), 2.76 (dt, J=2.4, 6.0 Hz, 1H), 3.78-3.86 (m, 2H), 5.00-5.14 (m, 2H), 5.52-5.80 (m, 3H), 6.12 (brd, J=10.8 Hz, 1H), 6.36 (dd, J=10.8, 15.2 Hz, 1H); LRMS $C_{36}H_{62}NaO_8Si$ (M+Na$^+$) Calcd: 673.41, Found: 673.26.

Total Synthesis of Pladienolide D

Step D1

Methyl-(2E)-3-methyl-5-[(1-phenyl-1-H-tetrazol-5-yl)sulfonyl]pent-2-enoate and ethyl-(2E)-3-methyl-5-[(1-phenyl-1-H-tetrazol-5-yl)thio]pent-2-enoate

[Formula 88]

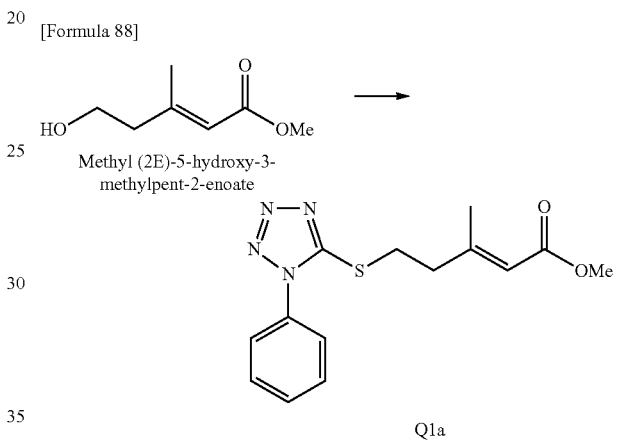

Methyl (2E)-5-hydroxy-3-methylpent-2-enoate

Q1a (1-1) Synthesis of methyl-(2E)-3-methyl-5-[(1-phenyl-1-H-tetrazol-5-yl)thio]pent-2-enoate (Q1a)

5-Mercapto-1-phenyltetrazole (2.62 g, 14.60 mmol), triphenylphosphine (3.83 g, 14.60 mmol) and diisopropyl azodicarboxylate (95%, 2.96 g, 14.60 mmol) were added to a THF (36.8 ml) solution of methyl-(2E)-5-hydroxy-3-methylpent-2-enoate (1.16 g, 7.31 mmol) while ice cooling. The reaction solution was warmed to room temperature and stirred for two hours. After the reaction solution was diluted with ethyl acetate, it was washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=5:1) to obtain the title compound (2.33 g) as a white solid.

400 MHz $^1$H-NMR (CDCl$_3$) δ (ppm) 2.22 (d, J=1.2 Hz, 3H), 2.70 (t, J=7.2 Hz, 2H), 3.54 (t, J=7.2 Hz, 2H), 3.70 (s, 3H), 5.70-5.74 (q, J=1.2 Hz, 1H), 7.52-7.59 (m, 5H); 100 MHz $^{13}$C-NMR (CDCl$_3$) δ (ppm) 18.41, 30.75, 39.68, 50.94, 117.30, 123.73, 129.81, 130.18, 133.46, 153.79, 155.84, 166.49; IR (KBr)=3071, 2991, 2948, 1707, 1648, 1593, 1499, 1437, 1412, 1380, 1226, 1153, 1057, 877, 761, 693, 559, 485, 407 cm$^{-1}$; HRMS $C_{14}H_{16}AgN_4O_2S$ (M+Ag$^+$) Calcd: 411.0045, Found: 411.0073.

[Formula 89]

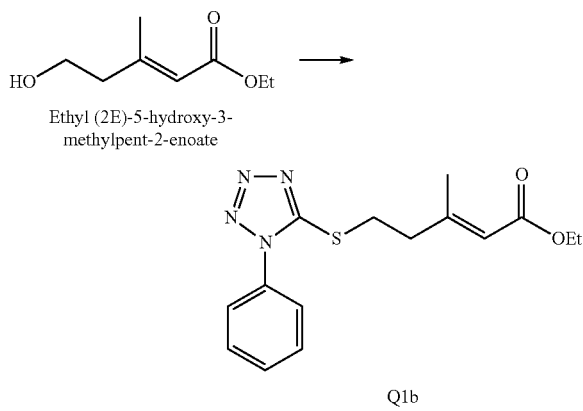

(1-2) Synthesis of ethyl-(2E)-3-methyl-5-[(1-phenyl-1-H-tetrazol-5-yl)thio]pent-2-enoate (Q1b)

This reaction was performed with reference to the literature (Mitsunobu, O., Synthesis, 1981, 1-28.). 5-Mercapto-1-phenyltetrazole (16.30 g, 91.20 mmol), triphenylphosphine (27.30 g, 104 mmol) and diisopropyl azodicarboxylate (95%, 21.10 g, 104 mmol) were added to a THF (410 ml) solution of ethyl-(2E)-5-hydroxy-3-methylpent-2-enoate (13.80 g, 86.90 mmol) while ice cooling. The reaction solution was warmed to room temperature and stirred for four hours. After the reaction solution was diluted with ethyl acetate, it was washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=5:1) to obtain the title compound (27.16 g) as a white solid.

400 MHz $^1$H-NMR (CDCl$_3$) δ (ppm) 1.26 (t, J=7.2 Hz, 3H), 2.22 (s, 3H), 2.70 (t, J=7.2 Hz, 2H), 3.54 (t, J=7.2 Hz, 2H), 4.15 (q, J=7.2 Hz, 2H), 5.72 (brs, 1H), 7.54-7.59 (m, 5H); 100 MHz $^{13}$C-NMR (CDCl$_3$) δ (ppm) 14.05, 18.22, 30.59, 39.53, 59.48, 117.58, 123.57, 129.61, 129.98, 133.33, 153.61, 155.24, 165.96; IR (KBr)=3064, 2981, 2939, 2903, 2358, 2341, 1713, 1650, 1597, 1500, 1386, 1278, 1222, 1145, 1054, 763, 694 cm$^{-1}$; HRMS C$_{15}$H$_{18}$AgN$_4$O$_2$S (M+Ag$^+$) Calcd: 425.0201, Found: 425.0170.

[Formula 90]

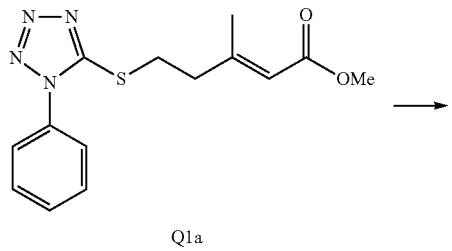

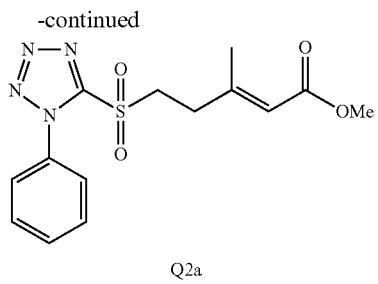

(2-1) Synthesis of methyl-(2E)-3-methyl-5-[(1-phenyl-1-H-tetrazol-5-yl)sulfonyl]pent-2-enoate (Q2a)

This reaction was performed with reference to the literature (Shultz, H. S.; Freyermuth, H. B.; Buc, S. R., J. Org. Chem., 1963, 28(4), 1140-1140.).

About 30% hydrogen peroxide solution (26.7 ml, 235 mmol) solution of hexaammonium heptamolybdate tetrahydrate (2.91 mg, 2.35 mmol) was added to an ethanol (150 ml) solution of methyl-(2E)-3-methyl-5-[(1-phenyl-1-H-tetrazol-5-yl)thio]pent-2-enoate (7.53 g, 24.70 mmol) at room temperature. After stirred for at the same temperature for 12 hours, the reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=4:1) to obtain the title compound (8.24 g) as a white solid.

400 MHz $^1$H-NMR (CDCl$_3$) δ (ppm) 2.24 (d, J=1.2 Hz, 3H), 2.79-2.83 (m, 2H), 3.71 (s, 3H), 3.88-3.92 (m, 2H), 5.77-5.78 (q, J=1.2 Hz, 1H), 7.60-7.71 (m, 5H); 100 MHz $^{13}$C-NMR (CDCl$_3$) δ (ppm) 18.25, 32.44, 50.90, 53.59, 117.67, 124.83, 129.51, 131.30, 132.66, 152.97, 165.99; IR (KBr)=3102, 3075, 2952, 2913, 1703, 1651, 1495, 1439, 1346, 1238, 1160, 1047, 998, 923, 882, 764, 689, 593, 550, 507, 456, 420 cm$^{-1}$; HRMS C$_{14}$H$_{16}$AgN$_4$O$_4$S (M+Ag$^+$) Calcd: 442.9943, Found: 442.9929.

[Formula 91]

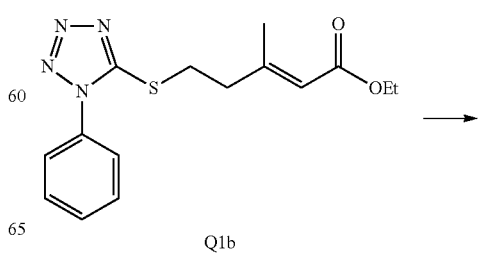

-continued

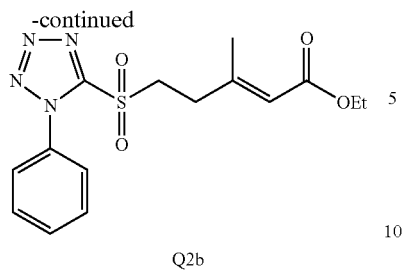

Q2b

(2-2) Synthesis of ethyl-(2E)-3-methyl-5-[(1-phenyl-1-H-tetrazol-5-yl)sulfonyl]pent-2-enoate (Q2b)

This reaction was performed with reference to the literature (Shultz, H. S.; Freyermuth, H. B.; Buc, S. R., J. Org. Chem., 1963, 28(4), 1140-1140.).

About 30% hydrogen peroxide solution (47.4 ml, 418.0 mmol) solution of hexaammonium heptamolybdate tetrahydrate (542 mg, 0.44 mmol) was added to an ethanol (200 ml) solution of ethyl-(2E)-3-methyl-5-[(1-phenyl-1-H-tetrazol-5-yl)thio]pent-2-enoate (13.31 g, 41.80 mmol) at room temperature. After stirred for at the same temperature for 12 hours, the reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:ethyl acetate=4:1) to obtain the title compound (12.65 g) as a white solid.

400 MHz $^1$H-NMR (CDCl$_3$) δ (ppm) 1.29 (t, J=7.2 Hz, 3H), 2.24 (d, J=1.2 Hz, 3H), 2.78-2.82 (m, 2H), 3.88-3.92 (m, 2H), 4.17 (q, J=7.2 Hz, 2H), 5.77 (brs, 1H), 7.59-7.71 (m, 5H); 100 MHz $^{13}$C-NMR (CDCl$_3$) δ (ppm) 14.22, 18.51, 32.72, 53.93, 59.97, 118.44, 124.95, 129.77, 131.55, 132.88, 152.56, 153.19, 165.81; IR (KBr)=3077, 3008, 2991, 2906, 1698, 1660, 1495, 1342, 1235, 1158, 1045, 877, 764, 689, 589, 550, 508, 454 cm$^{-1}$; HRMS C$_{15}$H$_{18}$AgN$_4$O$_4$S (M+Ag$^+$) Calcd: 457.0100, Found: 457.0133.

Step D2

Synthesis of (2E,5E,7S,8S)-3,7-dimethyl-8-[(triethylsilyl)oxy]deca-2,5-dien-1-ol

[Formula 92]

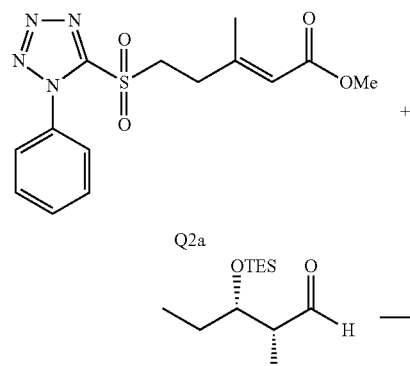

-continued

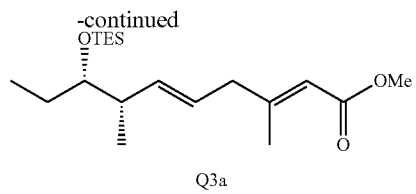

Q3a

(1-1) Synthesis of methyl-(2E,5E,7S,8S)-3,7-dimethyl-8-[(triethylsilyl)oxy]deca-2,5-dienoate (Q3a)

This reaction was performed with reference to the literature (Blakemore, P. R.; Cole, W. J.; Kociensky, P. J.; Morley, A., Synlett, 1998, 26-28.).

THF used at this step was distilled by using lithium aluminum hydride. In addition, DME was distilled by using calcium hydride.

0.5M Potassium bis(trimethylsilyl)amide toluene solution (8.48 ml, 4.24 mmol) was added dropwise to a DME (40 ml) solution of methyl-(2E)-3-methyl-5-[(1-phenyl-1-H-tetrazol-5-yl)sulfonyl]pent-2-enoate (1.19 g, 3.53 mmol) at −60° C. and the reaction solution was stirred at the same temperature for 30 minutes. Subsequently a THF (5 ml) solution of (2R,3S)-2-methyl-3-[(triethylsilyl)oxy]pentanal (1.63 g, 7.06 mmol) was added dropwise at −78° C. and the reaction solution was stirred for two hours. After the reaction solution was warmed to room temperature, distilled water was added. The reaction solution was diluted with ethyl acetate and washed with brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:diethyl ether=50:1) to obtain the title compound (1.17 g) as a colorless oil. The title compound was determined to be a mixture of E:Z=17:1 by $^1$H-NMR.

400 MHz $^1$H-NMR (CDCl$_3$) δ (ppm) 0.60 (q, J=8.0 Hz, 6H), 0.87 (t, J=7.2 Hz, 3H), 0.95 (t, J=8.0 Hz, 9H), 0.96 (d, J=6.8 Hz, 3H), 1.35-1.50 (m, 2H), 2.14 (d, J=1.2 Hz, 3H), 2.25-2.31 (m, 1H), 2.82 (d, J=6.4 Hz, 2H), 3.44-3.48 (m, 1H), 3.69 (s, 3H), 5.36 (ddd, J=6.8, 13.6, 15.6 Hz, 1H), 5.51 (dd, J=7.6, 15.2 Hz, 1H), 5.68 (q, J=1.2 Hz, 1H); 100 MHz $^{13}$C-NMR (CDCl$_3$) δ (ppm) 5.04, 6.78, 9.35, 15.41, 18.57, 26.65, 41.50, 43.86, 50.48, 77.18, 115.38, 124.80, 136.84, 158.86, 166.97; IR (neat)=2958, 2879, 2352, 2330, 1723, 1651, 1435, 1219, 1147, 1013, 740 cm$^{-1}$; HRMS C$_{19}$H$_{36}$AgO$_3$Si (M+Ag$^+$) Calcd: 447.1485, Found: 447.1461; [α]$_D^{21}$ −22.1 (c 1.10, CHCl$_3$).

[Formula 93]

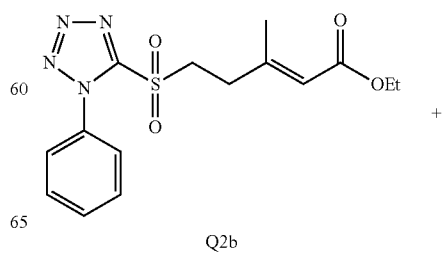

Q2b

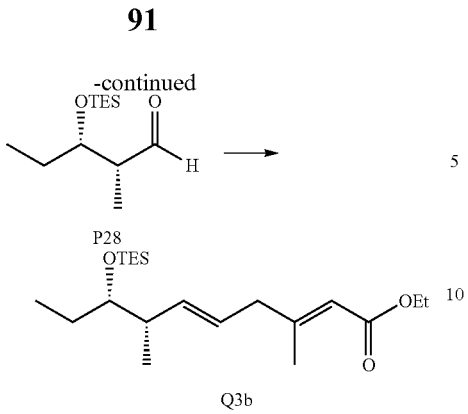

(1-2) Synthesis of ethyl-(2E,5E,7S,8S)-3,7-dimethyl-8-[(triethylsilyl)oxy]deca-2,5-dienoate (Q3b)

This reaction was performed with reference to a document (Blakemore, P. R.; Cole, W. J.; Kociensky, P. J.; Morley, A., Synlett, 1998, 26-28.).

THF used at this step was distilled from lithium hydride aluminum. In addition, DME was distilled from calcium hydride.

0.5M Toluene solution (64.2 ml) of potassium bis(trimethylsilyl)amide was added dropwise to a DME (280 ml) solution of ethyl-(2E)-3-methyl-5-[(1-phenyl-1-H-tetrazol-5-yl)sulfonyl]pent-2-enoate (9.0 g, 25.7 mmol) at −60° C. and the reaction solution was stirred at the same temperature for 30 minutes. Subsequently a THF (50 ml) solution of (2R,3S)-2-methyl-3-[(triethylsilyl)oxy]pentanal (12.0 g, 52.1 mmol) was added dropwise at −78° C. and the reaction solution was stirred for one hour. After the reaction solution was warmed to room temperature, distilled water was added. The reaction solution was diluted with ethyl acetate and washed with brine. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane: diethyl ether=100:1) to obtain the title compound (8.92 g) as a colorless oil. The title compound was determined to be a mixture of E:Z=18:1 by $^1$H-NMR.

400 MHz $^1$H-NMR (CDCl$_3$) δ (ppm) 0.60 (q, J=8.0 Hz, 6H), 0.87 (t, J=7.2 Hz, 3H), 0.95 (d, J=7.6 Hz, 3H), 0.96 (t, J=8.0 Hz, 9H), 1.27 (t, J=7.2 Hz, 3H), 1.36-1.53 (m, 2H), 2.13 (d, J=1.2 Hz, 3H), 2.26-2.32 (m, 1H), 2.81 (d, J=6.8 Hz, 2H), 3.44-3.48 (m, 1H), 4.14 (q, J=7.2 Hz, 2H), 5.36 (ddd, J=6.8, 13.6, 15.2 Hz, 1H), 5.51 (dd, J=7.6, 15.2 Hz, 1H), 5.67-5.68 (m, 1H); 100 MHz $^{13}$C-NMR (CDCl$_3$) δ (ppm) 5.05, 6.77, 9.35, 14.11, 15.37, 18.51, 26.67, 41.50, 43.89, 59.18, 77.20, 115.85, 124.88, 136.78, 158.38, 166.52; IR (neat)=2958, 2879, 2362, 2345, 1719, 1650, 1460, 1218, 1144, 1050, 1013, 740 cm$^{-1}$; HRMS C$_{20}$H$_{38}$AgO$_3$Si (M+Ag$^+$) Calcd: 461.1641, Found: 461.1640; [α]$_D^{22}$ −19.0 (c 2.06, CHCl$_3$).

[Formula 94]

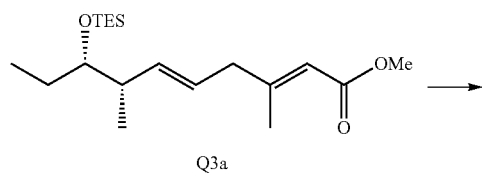

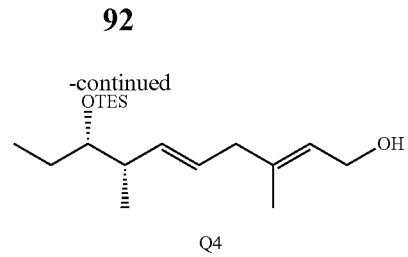

(2-1) Synthesis of (2E,5E,7S,8S)-3,7-dimethyl-8-[(triethylsilyl)oxy]deca-2,5-dien-1-ol (Q4)

1M toluene solution (1.76 ml, 1.76 mmol) of diisobutylaluminum hydride was added dropwise to an toluene (6 ml) solution of methyl-(2E,5E,7S,8S)-3,7-dimethyl-8-[(triethylsilyl)oxy]deca-2,5-dienoate (0.22 g, 0.64 mmol) at −78° C. and the reaction solution was stirred at the same temperature for 30 minutes. The reaction solution was diluted with diethyl ether, followed by addition of a saturated potassium sodium tartrate tetrahydrate aqueous solution (1.0 ml) and was warmed to room temperature and stirred for two hours. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:diethyl ether=8:1) to obtain the title compound (150 mg) as a colorless oil.

400 MHz $^1$H-NMR (CDCl$_3$) δ (ppm) 0.60 (q, J=7.6 Hz, 6H), 0.87 (t, J=7.6 Hz, 3H), 0.95 (d, J=14.0 Hz, 3H), 0.96 (t, J=7.6 Hz, 9H), 1.35-1.50 (m, 2H), 1.65 (brs, 3H), 2.24-2.29 (m, 1H), 2.70 (d, J=6.4 Hz, 2H), 3.45 (dd, J=5.6 Hz, 1H), 4.16 (d, J=7.2 Hz, 2H), 5.32-5.48 (m, 3H); 100 MHz $^{13}$C-NMR (CDCl$_3$) δ (ppm) 5.08, 6.85, 9.37, 15.73, 16.08, 26.72, 41.50, 42.82, 59.10 77.39, 123.82, 126.73, 135.25, 138.53; IR (neat)=3330, 2959, 2875, 1671, 1459, 1419, 1009, 740 cm$^{-1}$; HRMS C$_{18}$H$_{36}$AgO$_2$Si (M+Ag$^+$) Calcd: 419.1536, Found: 419.1572; [α]$_D^{21}$ −23.4 (c 1.45, CHCl$_3$).

[Formula 95]

(2-2) Synthesis of (2E,5E,7S,8S)-3,7-dimethyl-8-[(triethylsilyl)oxy]deca-2,5-dien-1-ol (Q4)

1M toluene solution of diisobutylaluminum hydride (52.2 ml, 52.2 mmol) was added dropwise to an anhydrous diethyl ether (37.5 ml) solution of ethyl-(2E,5E,7S,8S)-3,7-dimethyl-8-[(triethylsilyl)oxy]deca-2,5-dienoate (8.92 g, 25.20 mmol) at −78° C. and the reaction solution was stirred at the same temperature for one hour. Methanol (1 ml) and a saturated potassium sodium tartrate tetrahydrate aqueous solution (9.3 ml) were added to the reaction solution, and the mixture was warmed to room temperature and stirred for two hours. After the organic layer was dried over anhydrous sodium sulfate and the drying agent was filtered off, the organic layer was concentrated under reduced pressure. The obtained residue was purified by silica gel column chromatography (Merck, commercial name Silica Gel 60, 230-400 mesh; hexane:diethyl ether=8:1) to obtain the title compound (3.84 g) as a colorless oil. $^1$H-NMR data of the title compound obtained by (2-2) is completely identical to those of the title compound obtained by (2-1).

Step D3

Synthesis of {(2R,3R)-3-[(2E,4S,5S)-5-hydroxy-4-methylhept-2-en-1-yl]-3-methyloxiran-2-yl}methyl 4-methylbenzenesulfonate

[Formula 96]

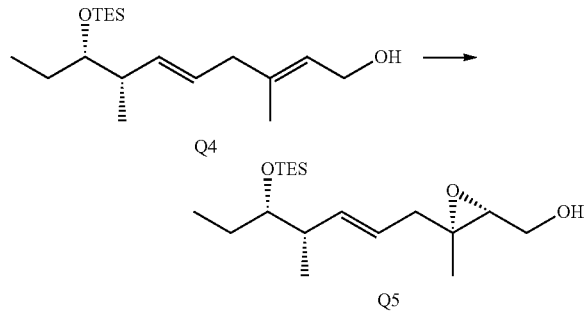

(1) Synthesis of (2R,3R)-3-methyl-3-{(2E,4S,5S)-4-methyl-5-[(triethylsilyl)oxy]hept-2-en-1-yl}oxiran-2-yl)methanol (Q5)

This reaction was performed with reference to the literature (Katsuki, T.; Sharpless, K. B., J. Am. Chem. Soc., 1980, 102, 5976-5978. Gao, Y.; Hanson, R. M. H.; Klunder, J. M.; Ko, S. Y.; Masamune, H.; Sharpless, K. B., ibid., 1987, 109, 5765-5780.).

(i) Distilled anhydrous dichloromethane (22 ml) was added to activated molecular sieves 4A powder (880 mg) under Ar atmosphere and the solution was cooled to −30° C. Subsequently, after diethyl (−)-tartrate (2.01 ml, 11.7 mmol) and titanium tetraisopropoxide (2.32 ml, 7.89 mmol) were added to the reaction solution under stirring and the mixture was stirred for five minutes, a dichloromethane (4 ml) solution of (2E,5E,7S,8S)-3,7-dimethyl-8-[(triethylsilyl)oxy]deca-2,5-dien-1-ol (1.76 g, 5.63 mmol) was added dropwise. After stirred for 30 minutes, 5M tert-butyl hydroperoxide decane solution (2.26 ml, 11.20 mmol) was added dropwise to the reaction solution over 15 minutes. Then the reaction solution was stirred at the same temperature for further 1.5 hours. Distilled water (5 ml) was added to the reaction solution and it was filtered through celite. The filtrate was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=5:1) to obtain the title compound (1.69 g, 90% de) as a colorless oil. The measurement of optical purity of the title compound was performed by converting the title compound to {(2R,3R)-3-[(2E,4S,5S)-5-hydroxy-4-methylhepta-2en-1-yl]-3-methyloxiran-2-yl}methyl 4-methylbenzenesulfonate (Q7) and determining by HPLC using a chiral column (DAICEL, commercial name CHIRALPAK AD-H, hexane:isopropylalcohol=90:10).

(ii) Distilled anhydrous dichloromethane (12 ml) was added to activated molecular sieves 4A powder (500 mg) under Ar atmosphere and the solution was cooled to −30° C. Subsequently, after isopropyl (−)-tartrate (0.202 ml, 0.96 mmol) and titanium tetraisopropoxide (0.189 ml, 0.640 mmol) were added to the reaction solution under stirring and the mixture was stirred for five minutes, a dichloromethane (3 ml) solution of (2S,5E,7S,8S)-3,7-dimethyl-8-[(triethylsilyl)oxy]deca-2,5-dien-1-ol (1.0 g, 3.20 mmol) was added dropwise. After stirred for 30 minutes, 5M tert-butyl hydroperoxide decane solution (1.28 ml, 6.36 mmol) was added dropwise to the reaction solution over 15 minutes. Then the reaction solution was stirred at the same temperature for further 2 hours. Distilled water (5 ml) was added to the reaction solution and it was filtered through celite. The filtrate was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=5:1) to obtain the title compound (925 mg, 82% de) as a colorless oil. The measurement of optical purity of the title compound was performed by converting the title compound to {(2R,3R)-3-[(2E,4S,5S)-5-hydroxy-4-methylhepta-2en-1-yl]-3-methyloxiran-2-yl}methyl 4-methylbenzenesulfonate (Q7) and determining by HPLC using a chiral column (DAICEL, commercial name CHIRALPAK AD-H, hexane:isopropylalcohol=90:10).

400 MHz $^1$H-NMR (CD$_3$OD) δ (ppm) 0.67 (q, J=8.0 Hz, 6H), 0.93 (t, J=7.6 Hz, 3H), 1.02 (d, J=6.8 Hz, 3H), 1.03 (t, J=8.0 Hz, 9H), 1.29 (s, 3H), 1.45-1.58 (m, 2H), 2.23-2.35 (m, 3H), 2.97 (dd, J=4.8, 6.4 Hz, 1H), 3.56 (dt, J=5.6, 6.0 Hz, 1H), 3.63 (dd, J=6.0, 12.0 Hz, 1H), 3.75 (dd, J=4.8, 12.0 Hz, 1H), 5.13 (dt, J=7.2, 15.6 Hz, 1H), 5.57 (dd, J=7.6, 15.6 Hz, 1H); 100 MHz $^{13}$C-NMR (CD$_3$OD) δ (ppm) 6.14, 7.43, 9.85, 16.39, 17.05, 27.91, 42.79, 42.99, 61.68, 61.72, 63.68, 78.70, 125.23, 138.18; IR (neat)=3422, 2959, 2877, 1459, 1239, 1103, 1016, 740 cm$^{-1}$; HRMS C$_{18}$H$_{36}$AgO$_3$Si (M+Ag$^+$) Calcd: 435.1485, Found: 435.1492; [α]$_D^{21}$ −15.1 (c 2.14, MeOH) (90% de).

[Formula 97]

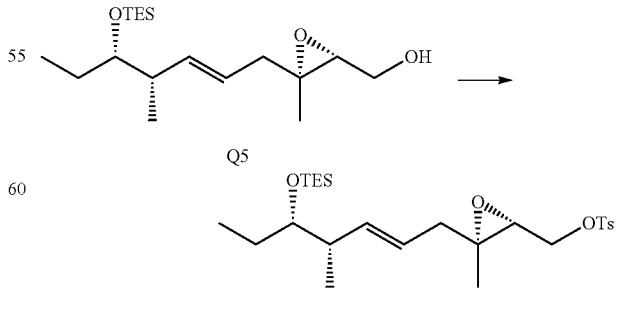

(2) Synthesis of (2R,3R)-3-methyl-3-{(2E,4S,5S)-4-methyl-5-[(triethylsilyl)oxy]hept-2-en-1-yl}oxiran-2-yl)methyl 4-methylbenzenesulfonate (Q6)

Triethylamine (1.86 ml, 12.90 mmol), 4-dimethylaminopyridine (23.7 mg, 0.19 mmol) and p-toluenesulphonyl chloride (493 mg, 2.59 mmol) were added to a dichloromethane (9 ml) solution of (2R,3R)-3-methyl-3-{(2E,4S,5S)-4-methyl-5-[(triethylsilyl)oxy]hept-2-en-1-yl}oxiran-2-yl)methanol (425 mg, 1.29 mmol, 90% de) at room temperature. The reaction solution was stirred at the same temperature for two hours. After the reaction solution was diluted with ethyl acetate, it was washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 µm; heptane:ethyl acetate=15:1) to obtain the title compound (641 mg, 90% de) as a colorless oil. The measurement of optical purity of the title compound was performed by converting the title compound to {(2R,3R)-3-[(2E,4S,5S)-5-hydroxy-4-methylhept-2-en-1-yl]-3-methyloxiran-2-yl}methyl 4-methylbenzenesulfonate (Q7) and determining by HPLC using a chiral column (DAICEL, commercial name CHIRALPAK AD-H, hexane:isopropylalcohol=90:10).

400 MHz $^1$H-NMR (CD$_3$OD), δ (ppm) 0.66 (q, j=8.0 Hz, 6H), 0.91 (t, j=7.6 Hz, 3H), 0.99 (d, j=7.2 Hz, 3H), 1.02 (t, J=8.0 Hz, 9H), 1.21 (s, 3H), 1.40-1.56 (m, 2H), 2.15-2.35 (m, 3H), 2.50 (s, 3H), 3.02 (dd, J=4.8, 6.8 Hz, 1H), 3.54 (dt, J=5.2, 6.0 Hz, 1H), 4.10 (dd, J=6.8, 11.2 Hz, 1H), 4.27 (dd, J=4.8, 11.2 Hz, 1H), 5.37 (dt, J=8.0, 15.6 Hz, 1H), 5.53 (dd, J=8.0, 15.6 Hz, 1H), 7.50 (ddd, J=1.0, 2.0, 6.8 Hz, 2H), 7.85 (dd, J=1.6, 6.8 Hz, 2H); 100 MHz $^{13}$C-NMR (CD$_3$OD) δ (ppm) 6.11, 7.51, 9.90, 16.44, 17.20, 21.73, 27.87, 42.11, 42.92, 59.45, 61.85, 70.33, 78.54, 124.60, 128.97, 131.07, 134.19, 138.53, 146.44; [α]$_D^{21}$ +2.70 (c 2.10, MeOH).

[Formula 98]

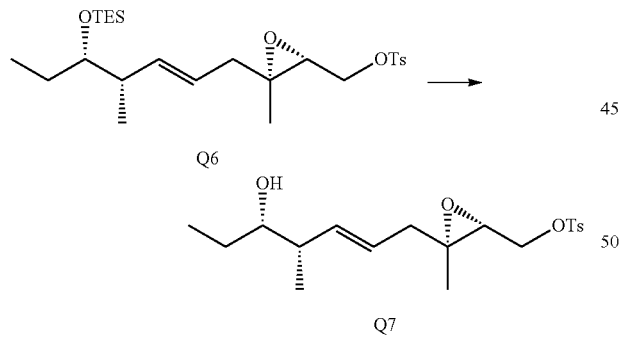

(3) Synthesis of {(2R,3R)-3-[(2E,4S,5S)-5-hydroxy-4-methylhept-2-en-1-yl]-3-methyloxiran-2-yl}methyl 4-methylbenzenesulfonate (Q7)

(i) To a THF (2 ml) solution of (2R,3R)-3-methyl-3-{(2E,4S,5S)-4-methyl-5-[(triethylsilyl)oxy]hept-2-en-1-yl}oxiran-2-yl)methyl 4-methylbenzenesulfonate (440 mg, 0.91 mmol, 90% de), 1M hydrochloric acid aqueous solution (0.1 ml) was added at room temperature and the reaction was stirred at the same temperature for one hour. After the reaction solution was diluted with ethyl acetate, it was washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 µm; heptane:ethyl acetate=2:1) to obtain the title compound (334 mg, 90% de) as a colorless oil. The optical purity was determined by HPLC using a chiral column (DAICEL, commercial name CHIRALPAK AD-H, hexane:isopropylalcohol=90:10).

(ii) The title compound ({(2R,3R)-3-[(2E,4S,5S)-5-hydroxy-4-methylhept-2-en-1-yl]-3-methyloxiran-2-yl}methyl 4-methylbenzenesulfonate) (850 mg, 82% de) was purified by HPLC using a preparative chiral column (DAICEL for fractionation, commercial name CHIRALPAK AD, 20×250 mm, hexane:isopropylalcohol=90:10, flow rate 10 mL/min) and the title compound (634 mg, >99% de) was obtained as a colorless oil. In addition, 13-epoxy isomer thereof (38 mg, >99% de) was obtained as a colorless oil.

Q7: 400 MHz $^1$H-NMR (CD$_3$OD) δ (ppm) 0.97 (t, J=7.6 Hz, 3H), 1.04 (d, J=6.8 Hz, 3H), 1.21 (s, 3H), 1.29-1.38 (m, 1H), 1.53-1.63 (m, 1H), 2.14-2.30 (m, 3H), 2.50 (s, 3H), 3.03 (dd, J=4.4, 6.8 Hz, 1H), 3.25-3.29 (m, 1H), 4.10 (dd, J=6.8, 11.2 Hz, 1H), 4.28 (dd, J=4.4, 11.2 Hz, 1H), 5.38 (dt, J=6.8, 15.6 Hz, 1H), 5.49 (dd, J=8.0, 15.6 Hz, 1H), 7.50 (dd, J=1.0, 8.4 Hz, 2H), 7.85 (ddd, J=2.0, 2.0, 8.4 Hz, 2H); 100 MHz $^{13}$C-NMR (CD$_3$OD) δ (ppm) 10.64, 16.58, 17.10, 21.62, 28.31, 41.96, 44.21, 59.51, 62.01, 70.43, 77.63, 124.85, 129.00, 131.13, 134.15, 138.80, 146.65; IR (neat)=3386, 2976, 2958, 2924, 2502, 1933, 1599, 1454, 1359, 1173, 1095, 967, 866, 782, 667, 554 cm$^{-1}$; HRMS C$_{19}$H$_{28}$NaO$_5$S (M+Na$^+$) Calcd: 391.1555, Found: 391.1550; [α]$_D^2$ +2.82 (c 1.04, MeOH). β-epoxy isomer (isomer of Q7): 400 MHz $^1$H-NMR (CD$_3$OD) δ (ppm) 0.98 (t, J=7.6 Hz, 3H), 1.04 (d, J=6.8 Hz, 3H), 1.21 (s, 3H), 1.27-1.42 (m, 1H), 1.53-1.65 (m, 1H), 2.13-2.31 (m, 3H), 2.50 (s, 3H), 3.03 (dd, J=4.8, 6.8 Hz, 1H), 3.23-3.31 (m, 1H), 4.10 (dd, J=6.8, 11.6 Hz, 1H), 4.28 (dd, J=4.8, 11.6 Hz, 1H), 5.38 (dt, J=7.2, 15.6 Hz, 1H), 5.49 (dd, J=8.0, 15.6 Hz, 1H), 7.50 (dd, J=0.8, 8.0 Hz, 2H), 7.85 (m, 2H).

Step D4

Synthesis of (1R)-1,2-anhydro-3,5-dideoxy-1-[(1R,2S)-2-hydroxy-1-methylbutyl]-4-C-vinyl-D-erythro-pentitol

[Formula 99]

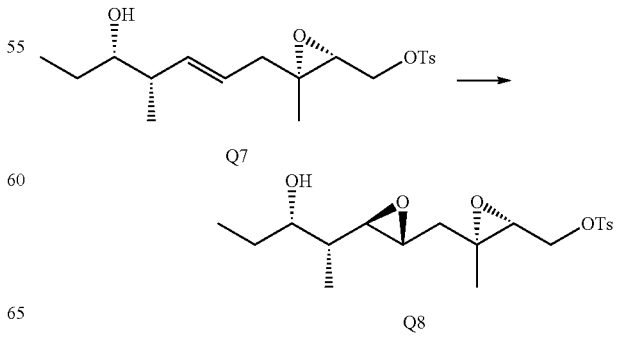

(1) Synthesis of 5,6:8,9-dianhydro-1,2,4,7-tetradeoxy-4,8-dimethyl-10-O-[(4-methylphenyl)sulfonyl]-D-threo-D-galacto-decitol (Q8)

This reaction was performed with reference to the literature (Wang, Z., -X.; Tu, Y.; Frohn, M.; Zhang, J.-R.; Shi, Y., J. Am. Chem. Soc., 1997, 119, 11224-11235. Wang, Z., -X.; Tu, Y.; Frohn, M.; Zhang, J.-R.; Shi, Y., J. Org. Chem., 1997, 62, 2328-2329.).

(i) {(2R,3R)-3-[(2E,4S,5S)-5-hydroxy-4-methylhept-2-en-1-yl]-3-methyloxiran-2-yl}methyl 4-methylbenzenesulfonate (2.82 g, 7.64 mmol, 89% de) was dissolved in acetonitrile (80.8 ml) and 0.4 mM ethylenediaminetetraacetic acid disodium salt solution (53.4 ml) of 0.05M sodium tetraborate decahydrate. 1,2:4,5-di-O-isopropylidene-D-erythro-2,3-hexodiuro-2,6-pyranose (1.97 g, 7.64 mmol) was added while ice cooling. Subsequently, a mixed powder of potassium carbonate (12.70 g, 91.80 mmol) and oxone (14.10 g, 22.93 mmol) were added at the same temperature over four hours. The reaction solution was stirred at the same temperature for another hour. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=3:1→2:1) to obtain the title compound (2.57 g, 81% de) as a colorless oil. The optical purity was determined by HPLC using a chiral column (DAICEL, commercial name CHIRALPAK AD-H, hexane:isopropylalcohol=80:20). Subsequently, it was recrystallized with a mixed solvent of hexane-diethyl ether and the title compound (1.52 g) was obtained as a colorless prism crystal of a single diastereomer (>99% de).

(ii) {(2R,3R)-3-[(2E,4S,5S)-5-hydroxy-4-methylhept-2-en-1-yl]-3-methyloxiran-2-yl}methyl 4-methylbenzenesulfonate (700 mg, 1.90 mmol, >99% de) was dissolved in acetonitrile (20.1 ml) and 0.4 mM ethylenediaminetetraacetic acid disodium salt solution (13.3 ml) of 0.05M sodium tetraborate decahydrate. 1,2:4,5-di-O-isopropylidene-D-erythro-2,3-hexodiuro-2,6-pyranose (489 mg, 1.90 mmol) was added while ice cooling. Subsequently, a mixed powder of potassium carbonate (3.15 g, 22.8 mmol) and oxone (3.50 g, 5.71 mmol) were added at the same temperature over four hours. The reaction solution was further stirred at the same temperature for one hour. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=3:1→2:1) to obtain the title compound (331 mg, 88% de) as a colorless oil. The optical purity was determined by HPLC using a chiral column (DAICEL, commercial name CHIRALPAK AD-H, hexane:isopropylalcohol=80:20).

400 MHz $^1$H-NMR (CD$_3$OD) δ(ppm) 0.98 (d, j=7.2 Hz, 3H), 0.99 (t, J=7.6 Hz, 3H), 1.27-1.36 (m, 1H), 1.32 (s, 3H), 1.48-1.61 (m, 2H), 1.67 (dd, J=6.8, 14.4 Hz, 1H), 1.80 (dd, J=4.8, 14.4 Hz, 1H), 2.50 (s, 3H), 2.71 (dd, J=6.4, 8.0 Hz, 1H), 2.85-2.89 (m, 1H), 3.10 (dd, J=4.4, 6.4 Hz, 1H), 3.57 (dt, J=4.8, 8.0 Hz, 1H), 4.12 (dd, J=6.4, 11.2 Hz, 1H), 4.31 (dd, J=4.4, 11.6 Hz, 1H), 7.44 (dd, J=1.0, 8.0 Hz, 2H), 7.86 (dd, J=2.0, 8.4 Hz, 1H), 7.87 (dd, J=2.0, 8.4 Hz, 1H); 100 MHz $^{13}$C-NMR (CD$_3$OD) δ (ppm) 10.55, 10.85, 17.41, 21.62, 28.55, 41.82, 42.36, 55.43, 60.18, 60.63, 61.63, 70.17, 75.15, 129.00, 131.13, 134.04, 146.66; IR (KBr)=3389, 2976, 2957, 2873, 1923, 1598, 1454, 1359, 1188, 1173, 1099, 969, 866, 815, 669, 557, 507 cm$^{-1}$; HRMS C$_{19}$H$_{28}$AgO$_6$S (M+Ag$^+$) Calcd: 491.0658, Found: 491.0638; [α]$_D^{23}$ +42.7 (c 1.00, MeOH) (>99% de).

[Formula 100]

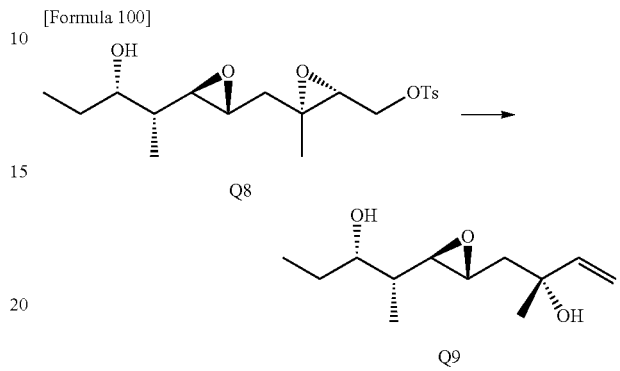

(2) Synthesis of (1R)-1,2-anhydro-3,5-dideoxy-1-[(1R,2S)-2-hydroxy-1-methylbutyl]-4-C-vinyl-D-erythro-pentitol (Q9)

This reaction was performed with reference to the literature (Fujii, N.; Habashita, H.; Akaji, M.; Nakai, K.; Ibuka, T.; Fujiwara, M.; Tamamura, H.; Yamamoto, Y., J. Chem. Soc., Perkin Trans. 1, 1996, 865-866.).

5,6:8,9-dianhydro-1,2,4,7-tetradeoxy-4,8-dimethyl-10-O-[(4-methylphenyl)sulfonyl]-D-threo-D-galacto-decitol (350 mg, 0.91 mmol) was dissolved in a mixture of acetone (17.5 ml) and DMF (3.5 ml), followed by addition of potassium iodide (528 mg, 3.18 mmol), and the mixture was heated to reflux for two hours. The reaction solution was cooled to 0° C., followed by addition of 4-(dimethylamino)phenyldiphenylphosphine (420 mg, 1.37 mmol) and iodine (100 mg, 0.45 mmol), and the mixture was stirred at the same temperature for 15 minutes. 5% Sodium hydrogen carbonate aqueous solution (3 ml) and 5% carbonic acid sodium thiosulfate aqueous solution (2 ml) were added to the reaction solution and it was stirred at the same temperature for further 10 minutes. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=2.5:1) to obtain the title compound (186 mg) as a colorless oil.

400 MHz $^1$H-NMR (CD$_3$OD) δ (ppm) 0.98 (d, J=7.2 Hz, 3H), 0.99 (t, J=7.6 Hz, 3H), 1.29-1.37 (m, 1H), 1.36 (s, 3H), 1.48-1.61 (m, 2H), 1.73 (dd, J=6.0, 14.0 Hz, 1H), 1.80 (dd, J=6.0, 14.0 Hz, 1H), 2.72 (dd, J=2.4, 7.6 Hz, 1H), 2.95 (dt, J=2.4, 6.0 Hz, 1H), 3.38 (s, 1H), 3.58 (dt, J=4.8, 8.0 Hz, 1H), 5.08 (dd, J=1.6, 10.8 Hz, 1H), 5.29 (dd, J=1.6, 17.6 Hz, 1H), 6.02 (dd, J=10.8, 17.6 Hz, 1H); 100 MHz $^{13}$C-NMR (CD$_3$OD) δ (ppm) 10.28, 10.92, 27.88, 28.54, 42.39, 45.54, 55.74, 62.10, 73.17, 75.18, 112.21, 146.27; IR (neat)=3418, 3088, 2970, 2935, 2879, 1647, 1455, 1416, 925 cm$^{-1}$; HRMS C$_{12}$H$_{22}$O$_3$Ag (M+Ag$^+$) Calcd: 321.0620, Found: 321.0667; [α]$_D^{24}$ +13.5 (c 1.67, MeOH) (>99% de).

(2-1) Alternative synthesis of (1R)-1,2-anhydro-3,5-dideoxy-1-[(1R,2S)-2-hydroxy-1-methylbutyl]-4-C-vinyl-D-erythro-pentitol (Q9)

This reaction was performed with reference to the literature (Sarandeses, L. A.; Mourino, A.; Luche, J-L., J. Chem. Soc., Chem. Commun., 1991, 818-820.).

5,6:8,9-dianhydro-1,2,4,7-tetradeoxy-4,8-dimethyl-10-O-[(4-methylphenyl)sulfonyl]-D-threo-D-galacto-decitol (200 mg, 0.53 mmol) was dissolved in a mixed solvent of acetone (5 ml) and DMF (1 ml), followed by addition of potassium iodide (303 mg, 1.83 mmol). The mixture was heated to reflux for two hours. The reaction solution was cooled to room temperature. 5% sodium hydrogen carbonate aqueous solution (3 ml) and 5% carbonic acid sodium thiosulfate aqueous solution (2 ml) were added to the reaction solution and it was stirred at the same temperature for further 10 minutes. The reaction solution was diluted with ethyl acetate and washed with distilled water and brine. After the organic layer was dried over anhydrous sodium sulfate, the drying agent was filtered off and the organic layer was concentrated under reduced pressure. The obtained crude product was used in the next step.

Zinc powder (102, 1.56 mmol) was dissolved in a mixted solution of ethanol (0.5 ml) and water (0.75 ml), followed by addition of copper iodide (99 mg, 0.52 mmol) and the mixed solution was treated with sonication for 5 minutes. An ethanolic solution of the above-obtained crude product (0.5 ml) was added to the reaction solution and it was treated with sonication at same temperature for 1.5 hours. The reaction solution was diluted with ethyl acetate and filtered through celite and washed with distilled water and brine. The organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 µm; heptane:ethylacetate=2.5:1) to obtain the title compound (110 mg) as a colorless oil. ¹H-NMR data of title compound by this alternative method are completely identical to those of the title compound obtained by the above (2).

Step D5

Synthesis of (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate and (2S,3S,4E,6S,7R,10R)-7-hydroxy-3,7-dimethyl-2-[(1E)-1-methylbuta-1,3-dien-1-yl]-12-oxo-10-[(triethylsilyl)oxy]oxacyclododec-4-en-6-yl acetate

[Formula 101]

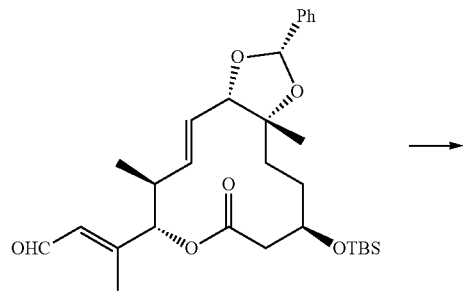

P18

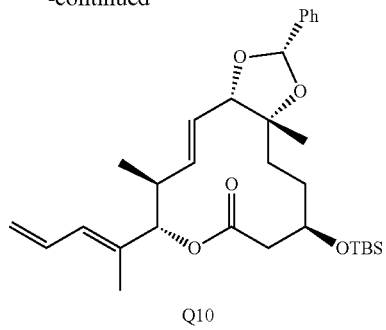

Q10

(1) Synthesis of (2S,3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (Q10)

This reaction was performed with reference to the literature (Pine, S. H.; Zahler, R.; Evans, D. A.; Grubbs, R. H., J. Am. Chem. Soc., 1980, 3270-3272.).

(2S,3aS,4E,6S,7S,13aR)-11-{[tert-butyl(dimethyl)silyl]oxy}-7-[(E)-2-formyl-1-methyleth-1-en-1-yl]-6,13a-dimethyl-2-phenyl-3a,6,7,10,11,12,13,13a-octahydro-9H-[1,3]dioxolo[4,5-f]oxacyclododecin-9-one (50 mg, 0.09 mmol) was dissolved in a mixed solvent of THF (0.4 ml) and toluene (2.8 ml), and the solution was cooled to –40° C. After addition of pyridine (0.38 ml, 4.73 mmol) and 0.5M toluene solution (1.14 ml, 0.57 mmol) of Tebbe reagent (chlorobis(cyclopentadienyl)-(dimethylaluminum)-methylene titanium), the mixture was stirred at the same temperature for 30 minutes. It was warmed to room temperature and further stirred for one hour. Distilled water (1 ml) was added to the reaction solution, and the reaction solution was diluted with ethyl acetate and washed with distilled water and brine sequentially, and after dried over anhydrous sodium sulfate, the drying agent was filtered off and the organic layer was concentrated under reduced pressure. The obtained residue was purified by silica gel column chromatography (Merck, commercial name Silica Gel 60, 230-400 mesh; hexane:diethyl ether=4:1) to obtain the title compound (36.3 mg) as a colorless amorphous substance.

400 MHz ¹H-NMR (CDCl$_3$) δ (ppm) 0.07 (s, 3H), 0.09 (s, 3H), 0.88 (s, 9H), 0.89 (d, J=6.0 Hz, 3H), 1.35-1.47 (m, 2H), 1.38 (s, 3H), 1.59-1.67 (m, 1H), 1.74 (d, J=0.8 Hz, 3H), 2.01-2.09 (m, 1H), 2.31 (dd, J=10.4, 14.4 Hz, 1H), 2.58 (dd, J=4.4, 14.4 Hz, 1H), 2.54-2.63 (m, 1H), 3.94-4.02 (m, 1H), 4.19 (d, J=9.2 Hz, 1H), 4.97 (d, J=10.4 Hz, 1H), 5.18 (dd, J=1.6, 17.6 Hz, 1H), 5.27 (dd, J=1.6, 17.2 Hz, 1H), 5.40 (dd, J=9.6, 15.2 Hz, 1H), 5.64 (dd, J=9.6, 15.2 Hz, 1H), 5.91 (s, 1H), 6.13 (d, J=10.8 Hz, 1H), 6.54 (dt, J=10.4, 17.2 Hz, 1H), 7.34-7.41 (m, 3H), 7.48-7.52 (m, 2H); 100 MHz ¹³C-NMR (CDCl$_3$) δ (ppm) –4.63,–4.51, 11.63, 16.72, 17.93, 22.82, 25.72, 31.59, 34.42, 40.24, 44.11, 71.62, 82.07, 83.61, 85.32, 101.21, 118.83, 126.75, 128.32, 129.28, 129.57, 131.26, 131.87, 133.41, 137.69, 137.76, 169.18; IR (KBr)=2957, 2931, 2857, 1735, 1459, 1375, 1275, 1244, 1174, 1078, 1005, 975, 908, 877, 835, 775, 759, 698 cm$^{-1}$; HRMS $C_{31}H_{46}AgO_5Si$ (M+Ag$^+$) Calcd: 633.2165, Found: 633.2189; $[\alpha]_D^{23}$ +19.5 (c 0.90, CHCl$_3$).

[Formula 102]

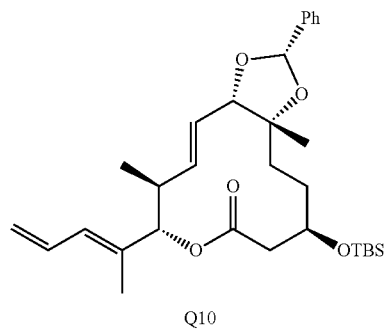

Q10

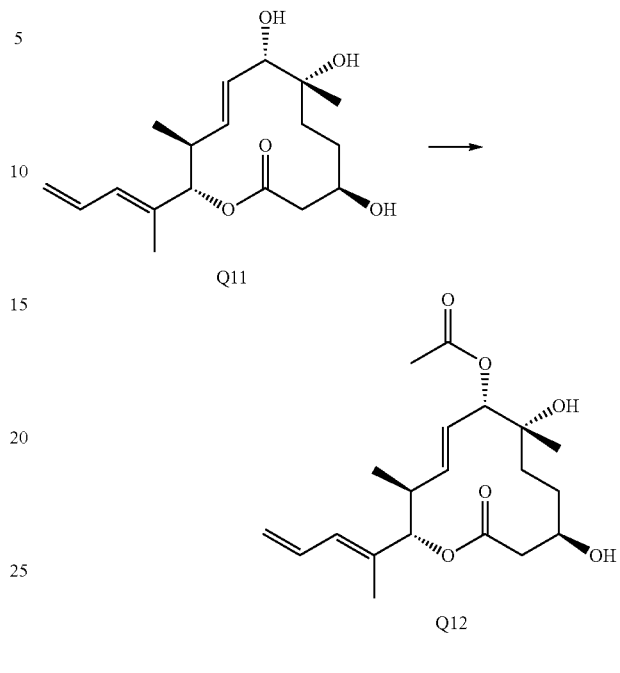

(2) Synthesis of (4R,7R,8S,9E,11S,12S)-4,7,8-trihydroxy-7,11-dimethyl-12-[(1E)-1-methylbuta-1,3-dien-1-yl]-oxacyclododec-9-en-2-one (Q11)

Pyridinium p-toluene sulfonate (68.2 mg, 271 μmol) was added to a methanol (1.22 ml) solution of (2S,3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (36.0 mg, 0.07 mmol) and the reaction solution was stirred at room temperature for four days. Distilled water (1 ml) was added to the reaction solution, and the reaction solution was diluted with ethyl acetate and washed with distilled water and brine sequentially, and after dried over anhydrous sodium sulfate, the drying agent was filtered off and the organic layer was concentrated under reduced pressure. The obtained residue was purified by silica gel column chromatography (Merck, commercial name Silica Gel 60, 230-400 mesh; hexane:diethyl ether=1:3) to obtain the title compound (18.3 mg) as a white solid.

400 MHz $^1$H-NMR (CDCl$_3$) δ (ppm) 0.92 (d, J=6.9 Hz, 3H), 1.24-1.32 (m, 1H), 1.31 (s, 3H), 1.36-1.72 (m, 3H), 1.76 (d, J=1.0 Hz, 3H), 2.51-2.65 (m, 3H), 3.72-3.77 (m, 1H), 3.82 (d, J=9.6 Hz, 1H), 5.17 (d, J=10.8 Hz, 1H), 5.20 (d, J=11.2 Hz, 1H), 5.28 (dd, J=1.6, 16.8 Hz, 1H), 5.43 (dd, J=10.0, 15.2 Hz, 1H), 5.73 (dd, J=10.0, 15.2 Hz, 1H), 6.12 (d, J=11.6 Hz, 1H), 6.55 (dt, J=10.4, 16.8 Hz, 1H); 100 MHz $^{13}$C-NMR (CDCl$_3$) δ (ppm) 11.75, 16.52, 24.45, 29.72, 35.57, 38.23, 40.66, 69.23, 73.39, 77.12, 82.45, 119.17, 130.19, 131.61, 131.81, 132.94, 137.18, 172.16; IR (KBr)=3473, 3336, 2960, 2928, 2872, 1729, 1604, 1580, 1460, 1274, 1122, 1028, 959, 743, 420 cm$^{-1}$; HRMS $C_{18}H_{28}AgO_5$ (M+Ag$^+$) Calcd: 431.0988, Found: 431.0960; $[\alpha]_D^{22}$ +7.01 (c 1.09, CHCl$_3$).

(3) Synthesis of (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate (Q12)

Triethylamine (35.6 μl, 246 μmol), acetic anhydride (11.6 μl, 123 μmol) and 4-dimethylaminopyridine (3.0 mg, 24.6 μmol) were added to an anhydrous dichloromethane (2 ml) solution of (4R,7R,8S,9E,11S,12S)-4,7,8-trihydroxy-7,11-dimethyl-12-[(1E)-1-methylbuta-1,3-dien-1-yl]-oxacyclododec-9-en-2-one (40.0 mg, 123 μmol) at 0° C. and the reaction solution was stirred at the same temperature for one hour. The reaction solution was poured into a saturated sodium hydrogen carbonate aqueous solution, and the reaction solution was diluted with ethyl acetate and washed with distilled water and brine sequentially, and after dried over anhydrous sodium sulfate, the drying agent was filtered off and the organic layer was concentrated under reduced pressure. The obtained residue was purified by silica gel column chromatography (Merck, commercial name Silica Gel 60, 230-400 mesh; hexane:diethyl ether=1:2) to obtain the title compound (42 mg) as a white solid.

400 MHz $^1$H-NMR (CDCl$_3$) δ (ppm) 0.90 (d, J=6.8 Hz, 3H), 1.21 (s, 3H), 1.25-1.42 (m, 2H), 1.51-1.74 (m, 2H), 1.75 (s, 3H), 2.09 (s, 3H), 2.16 (s, 1H), 2.46-2.67 (m, 3H), 3.54 (d, J=11.2 Hz, 1H), 3.70-3.80 (m, 1H), 5.09 (d, J=8.8 Hz, 1H), 5.17 (d, J=10.8 Hz, 1H), 5.18 (d, J=10.0 Hz, 1H), 5.28 (d, J=16.8 Hz, 1H), 5.61 (dd, J=9.6, 15.2 Hz, 1H), 5.68 (dd, J=9.6, 15.2 Hz, 1H), 6.12 (d, J=10.8 Hz, 1H), 6.55 (dt, J=10.4, 16.8 Hz, 1H); 100 MHz $^{13}$C-NMR (CDCl$_3$) δ (ppm) 11.75, 16.40, 21.24, 24.57, 29.75, 35.15, 38.26, 40.71, 69.11, 73.35, 78.85, 82.39, 119.19, 125.57, 131.65, 131.79, 132.88, 140.39, 169.61, 172.00; IR (KBr)=3513, 3404, 2970, 2948, 2876, 1734, 1705, 1454, 1429, 1405, 1361, 1248, 1175, 1051, 1023, 968, 921, 652, 550, 508 cm$^{-1}$; HRMS $C_{20}H_{30}O_6Na$ (M+Na$^+$) Calcd: 389.1940, Found: 389.1927; $[\alpha]_D^{22}$ +22.2 (c 1.21, CHCl$_3$).

[Formula 104]

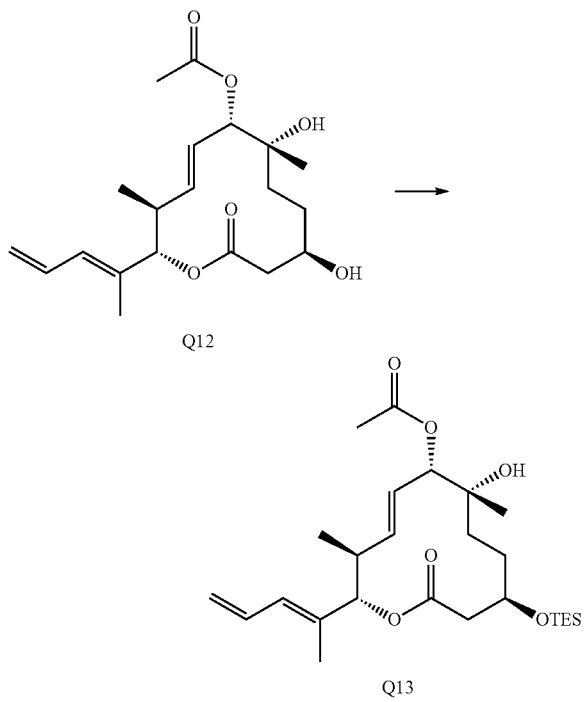

Q12

Q13

(4) Synthesis of (2S,3S,4E,6S,7R,10R)-7-hydroxy-3,7-dimethyl-2-[(1E)-1-methylbuta-1,3-dien-1-yl]-12-oxo-10-[(triethylsilyl)oxy]oxacyclododec-4-en-6-yl acetate (Q13)

Triethylamine (260 μl, 1.80 mmol), 4-dimethylaminopyridine (4.26 mg, 0.349 mmol) and chlorotriethylsilane (48 μl, 0.286 mmol) were added to an anhydrous dichloromethane (1.5 ml) solution of (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate (30.0 mg, 0.082 mmol) at room temperature and the reaction solution was stirred at the same temperature for five hours. The reaction solution was diluted with ethyl acetate and washed with a saturated sodium hydrogen carbonate aqueous solution, distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=1:2) to obtain the title compound (33 mg) as a white solid.

400 MHz $^1$H-NMR (CDCl$_3$) δ (ppm) 0.61 (q, J=8.0 Hz, 6H), 0.89 (d, J=6.8 Hz, 3H), 0.97 (t, J=8.0 Hz, 9H), 1.20 (s, 3H), 1.34-1.50 (m, 3H), 1.65-1.70 (m, 1H), 1.72 (d, J=1.2 Hz, 3H), 2.09 (s, 3H), 2.41 (dd, J=1.2, 14.0 Hz, 1H), 2.48 (dd, J=3.6, 14.0 Hz, 1H), 2.49-2.53 (m, 1H), 3.80-3.90 (m, 1H), 4.98 (d, J=10.4 Hz, 1H), 5.07-5.09 (m, 1H), 5.15 (d, J=10.0 Hz, 1H), 5.24 (dd, J=1.6, 16.8 Hz, 1H), 5.58-5.70 (m, 2H), 6.14 (d, J=10.8 Hz, 1H), 6.53 (dt, J=10.4, 16.8 Hz, 1H); 100 MHz $^{13}$C-NMR (CDCl$_3$) δ (ppm) 4.70, 6.80, 11.85, 16.47, 21.25, 24.80, 30.30, 35.57, 40.48, 40.70, 70.16, 73.58 78.99, 82.23, 118.57, 125.09, 131.16, 131.99, 133.58, 140.73, 168.67, 169.59; IR (neat)=3316, 2956, 2911, 2875, 1739, 1459, 1370, 1240, 1170, 1089, 1020, 979, 908, 744 cm$^{-1}$; HRMS C$_{26}$H$_{44}$AgO$_6$Si (M+Ag$^+$) Calcd: 587.1958, Found: 587.1915; [α]$_D^{26}$ +34.8 (c 1.50, CHCl$_3$).

Step D6

Synthesis of Pladienolide D and its Analogues

[Formula 105]

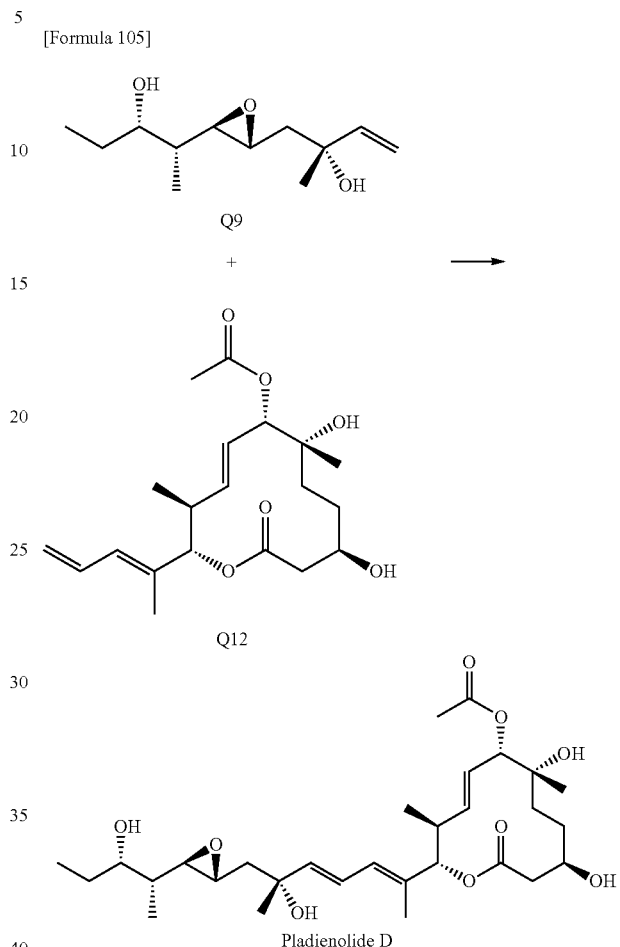

Q9

+

Q12

Pladienolide D (1) Synthesis of Pladienolide D

This reaction was performed with reference to the literature (Grubbs, R. H. "Handbook of Metathesis", Wiley-VCH, 2003, v. 2, p 246-292).

(i) (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate (10.0 mg, 27.3 μmol) and (1R)-1,2-anhydro-3,5-dideoxy-1-[(1R,2S)-2-hydroxy-1-methylbutyl]-4-C-vinyl-D-erythro-pentitol (17.6 mg, 81.9 μmol) were dissolved in anhydrous dichloromethane (1 ml) under Ar atmosphere, followed by addition of the second generation Hoveyda-Grubbs catalyst; [1,3-bis-(2,4,6-trimethylphenyl)-2-imidazolidinylidene]dichloro(O-isopropoxyphenylmethylene)ruthenium (0.85 mg, 1.4 μmol). After the reaction solution was warmed to reflux for one hour, it was cooled to room temperature and concentrated under reduced pressure. The obtained residue was purified by silica gel column chromatography (Kanto, commercial name Silica Gel 60N, 40-100 μm; heptane:ethyl acetate=2.5:1→1:2→0:1) to obtain the title compound (9.5 mg) as a white amorphous.

(ii) (2S,3S,4E,6S,7R,10R)-7,10-dihydroxy-3,7-dimethyl-2-[(1E)-1-methylbuta-1,3-dien-1-yl]-12-oxooxacyclododec-4-en-6-yl acetate (10.0 mg, 27.3 μmol) and (1R)-1,2-anhydro-3,5-dideoxy-1-[(1R,2S)-2-hydroxy-1-methylbutyl]-4-C-vinyl-D-erythro-pentitol (11.7 mg, 54.6 μmol) were dissolved in anhydrous dichloromethane (2.5 ml) under Ar atmosphere, followed by addition of the second generation Grubbs catalyst; [1,3-bis-(2,4,6-trimethylphenyl)-2-imidazolidinylidene]dichloro(phenylmethylene)-tricyclohexylphospine)ruthenium (1.16 mg, 1.4 μmol). After the reaction solution was heated to reflux for one hour, it was cooled to room temperature and concentrated under reduced pressure. The obtained residue was purified by silica gel column chromatography (Kanto, commercial name Silica Gel 60N, 40-100 μm; heptane:ethyl acetate=2.5:1→1:2→0:1) to obtain the title compound (9.5 mg) as a white amorphous.

600 MHz $^1$H-NMR (CD$_3$OD) δ (ppm) 0.93 (d, J=6.8 Hz, 3H), 0.94 (d, J=7.0 Hz, 3H), 0.98 (t, J=7.4 Hz, 3H), 1.23 (s, 3H), 1.30 (m, 1H), 1.38 (s, 3H), 1.40 (m, 1H), 1.42 (m, 1H), 1.54 (m, 2H), 1.62 (m, 1H), 1.66 (m, 1H), 1.70 (dd, J=6.3, 14.1 Hz, 1H), 1.82 (d, J=0.9 Hz, 3H), 1.91 (dd, J=5.5, 14.0 Hz, 1H), 2.10 (s, 3H), 2.57 (m, 2H), 2.62 (ddq, J=6.8, 9.8, 10.6 Hz, 1H), 2.71 (dd, J=2.2, 7.9 Hz, 1H), 2.93 (ddd, J=2.2, 6.3, 6.3 Hz, 1H), 3.57 (ddd, J=4.5, 4.5, 8.3 Hz, 1H), 3.83 (m, 1H), 5.09 (d, J=9.8 Hz, 1H), 5.11 (d, J=10.6 Hz, 1H), 5.61 (dd, J=9.9, 15.2 Hz, 1H), 5.75 (dd, J=9.8, 15.2 Hz, 1H), 5.92 (d, J=15.3 Hz, 1H), 6.18 (d, J=11.0 Hz, 1H), 6.57 (dd, J=11.0, 15.3 Hz, 1H); 150 MHz $^{13}$C-NMR (CD$_3$OD) δ (ppm) 10.5, 10.8, 12.0, 16.9, 21.1, 24.2, 28.6, 28.8, 30.5, 37.5, 40.1, 41.8, 42.6, 46.0, 56.0, 62.5, 70.4, 73.1, 74.1, 75.3, 80.3, 84.2, 123.7, 127.1, 131.8, 133.8, 141.6, 143.2, 171.7, 172.2; IR (KBr)=3438, 2968, 2939, 2879, 1733, 1720, 1458, 1371, 1244, 1176, 1021, 977, 832, 789, 747, 612, 551, 474, 433, 420, 409 cm$^{-1}$; HRMS: C$_{30}$H$_{48}$NaO$_9$ (M+Na$^+$), Calcd: 575.3196, Found: 575.3168; [α]$_D^{25}$ −14.7 (c 1.10, MeOH).

[Formula 106]

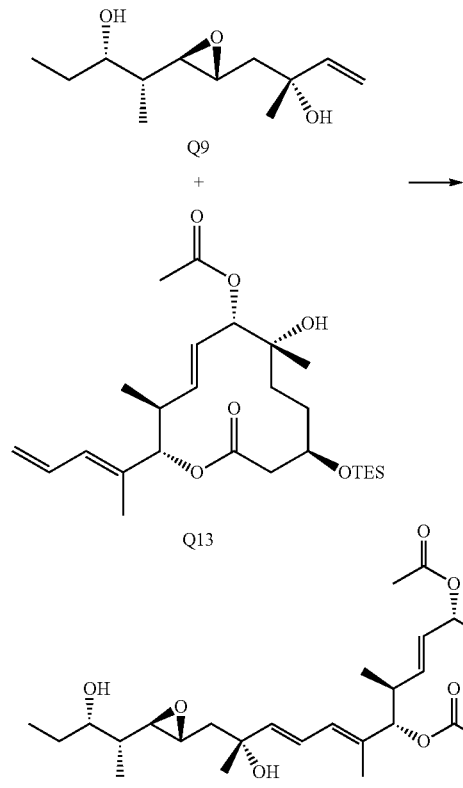

(2) Synthesis of 3-[(triethylsilyl)oxy]-pladienolide D

This reaction was performed with reference to the literature (Grubbs, R. H. "Handbook of Metathesis", Wiley-VCH, 2003, v. 2, p 246-292).

(2S,3S,4E,6S,7R,10R)-7-hydroxy-3,7-dimethyl-2-[(1E)-1-methylbuta-1,3-dien-1-yl]-12-oxo-10-[(triethylsilyl)oxy]oxacyclododec-4-en-6-yl acetate (8.60 mg, 17.9 μmol) and (1R)-1,2-anhydro-3,5-dideoxy-1-[(1R,2S)-2-hydroxy-1-methylbutyl]-4-C-vinyl-D-erythro-pentitol (8.67 mg, 40.5 μmol) were dissolved in anhydrous dichloromethane (1.8 ml) under Ar atmosphere, followed by addition of the second generation Grubbs catalyst; [1,3-bis-(2,4,6-trimethylphenyl)-2-imidazolidinylidene]dichloro(phenylmethylene)-tricyclohexylphospine)ruthenium (0.76 mg, 0.9 μmol). After the reaction solution was heated to reflux for 1.5 hours, it was cooled to room temperature and concentrated under reduced pressure. The obtained residue was purified by silica gel column chromatography (Kanto, commercial name Silica Gel 60N, 40-100 μm; heptane:ethyl acetate=3:1→2:1→1:1→0:1) to obtain the title compound (11.9 mg) as a colorless oil.

400 MHz $^1$H-NMR (CD$_3$OD) δ (ppm) 0.68 (q, J=7.6 Hz, 6H), 0.93 (d, J=6.8 Hz, 3H), 0.94 (d, J=7.2 Hz, 3H), 0.98 (t, J=7.2 Hz, 3H), 1.03 (t, J=7.6 Hz, 9H), 1.21 (s, 3H), 1.26-1.31 (m, 1H), 1.32-1.36 (m, 2H), 1.38 (s, 3H), 1.38-1.42 (m, 1H), 1.46-1.60 (m, 3H), 1.70 (dd, J=6.4, 14.0 Hz, 1H), 1.80 (d, J=1.2 Hz, 3H), 1.91 (dd, J=5.6, 14.4 Hz, 1H), 2.10 (s, 3H), 2.43 (dd, J=4.8, 14.0 Hz, 1H), 2.56 (dd, J=3.2, 14.0 Hz, 1H), 2.58-2.66 (m, 1H), 2.71 (dd, J=2.4, 8.0 Hz, 1H), 2.94 (dt, J=2.4, 6.4 Hz, 1H), 3.57 (dt, J=4.4, 8.0 Hz, 1H), 3.90-4.01 (m, 1H), 4.97 (d, J=10.8 Hz, 1H), 5.06 (d, J=9.6 Hz, 1H), 5.61 (dd, J=10.0, 15.2 Hz, 1H), 5.75 (dd, J=9.6, 15.2 Hz, 1H), 5.91 (d, J=15.2 Hz, 1H), 6.18 (dd, J=1.2, 11.2 Hz, 1H), 6.57 (dd, J=11.2, 15.2 Hz, 1H); HRMS: C$_{36}$H$_{62}$O$_9$NaSi (M+Na$^+$), Calcd: 689.4061, Found: 689.4044.

[Formula 107]

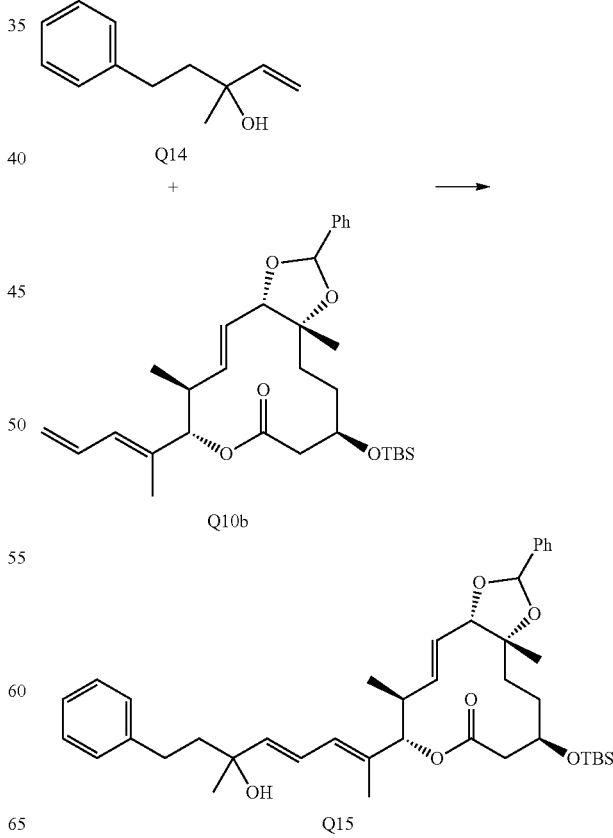

(3) Synthesis of (3aS,4E,6S,7S,11R,13aR)-11-{[tert-butyl(dimethyl)silyl]oxy}-7-[(1E,3E)-5-hydroxy-1,5-dimethyl-7-phenylhepta-1,3-dien-1-yl]-6,13a-dimethyl-2-phenyl-3a,6,7,10,11,12,13,13a-octahydro-9H-[1,3]dioxolo[4,5-f]oxacyclododecin-9-one (Q15)

This reaction was performed with reference to the literature (Grubbs, R. H. "Handbook of Metathesis", Wiley-VCH, 2003, v. 2, p 246-292).

(3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (15.0 mg, 28.5 μmol) and 3-methyl-5-phenylpent-1-en-3-ol (15.1 mg, 85.5 μmol) were dissolved in anhydrous dichloromethane (1.0 ml) under Ar atmosphere, followed by addition of the second generation Grubbs catalyst; [1,3-bis-(2,4,6-trimethylphenyl)-2-imidazolidinylidene]dichloro(phenylmethylene)-tricyclohexylphospine)ruthenium (2.0 mg, 2.4 μmol). The reaction solution was stirred at room temperature for 12 hours. Furthermore, the reaction solution was heated to reflux for five hours. The reaction solution was cooled to room temperature and concentrated under reduced pressure. The obtained residue was purified by silica gel column chromatography (Merck, commercial name Silica Gel 60, 230-400 mesh; heptane:ethyl acetate=6:1→3:1) to obtain the title compound (14.1 mg) as a colorless oil. The title compound was determined to be a mixture of α benzylidene acetal and β benzylidene acetal in a ratio of 1:3 by $^1$H-NMR.

Q15β: 400 MHz $^1$H-NMR (CDCl$_3$) δ (ppm) 0.08 (s, 3H), 0.10 (s, 3H), 0.89 (s, 9H), 0.93 (d, J=6.8 Hz, 3H), 1.24-1.28 (m, 1H), 1.35 (s, 3H), 1.37 (s, 3H), 1.39-1.47 (m, 1H), 1.69 (t, J=11.6 Hz, 1H), 1.78 (s, 3H), 1.80-1.94 (m, 2H), 1.99-2.04 (m, 1H), 2.32 (dd, J=6.0, 14.4 Hz, 1H), 2.56-2.69 (m, 4H), 3.94-4.05 (m, 1H), 4.32 (d, J=10.0 Hz, 1H), 5.01 (d, J=10.8 Hz, 0.6H), 5.02 (d, J=10.8 Hz, 0.4H), 5.46 (dd, J=9.6, 15.2 Hz, 1H), 5.86 (dd, J=15.2 Hz, 1H), 5.84-5.92 (m, 1H), 6.10 (s, 1H), 6.15 (d, J=10.8 Hz, 1H), 6.44-6.52 (m, 1H), 7.14-7.20 (m, 3H), 7.20-7.27 (m, 3H), 7.30-7.39 (m, 2H), 7.47-7.52 (m, 2H); LRMS C$_{41}$H$_{58}$NaO$_6$Si (M+Na$^+$) Calcd: 697.39, Found: 697.44.

REFERENCE EXAMPLES

Synthesis of (3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (Q10b)

[Formula 108]

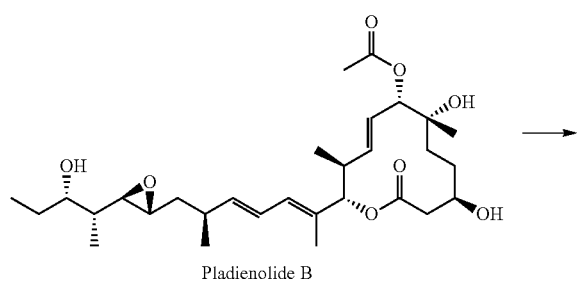

Pladienolide B

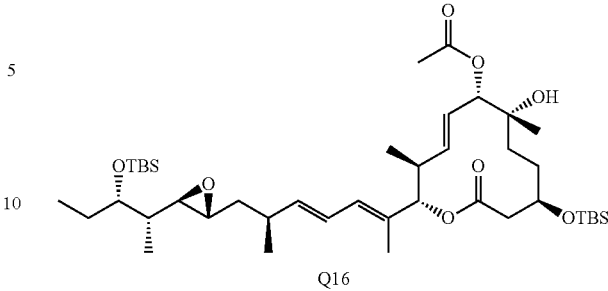

Q16

(1) Synthesis of 3,21-bis{[tert-butyl(dimethyl)silyl]oxy}-pladienolide B (Q16)

Imidazole (1.66 g, 24.4 mmol) and tert-butyldimethylsilyl chloride (3.68 g, 24.4 mmol) were added to a DMF (21.8 ml) solution of pladienolide B (2.18 g, 2.44 mmol, 60% purity) at room temperature and it was stirred at the same temperature for two hours. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=4:1) to obtain the title compound (1.68 g) as a white amorphous. LRMS C$_{42}$H$_{76}$NaO$_8$Si$_2$ (M+Na$^+$) Calcd: 787.50, Found: 787.62.

[Formula 109]

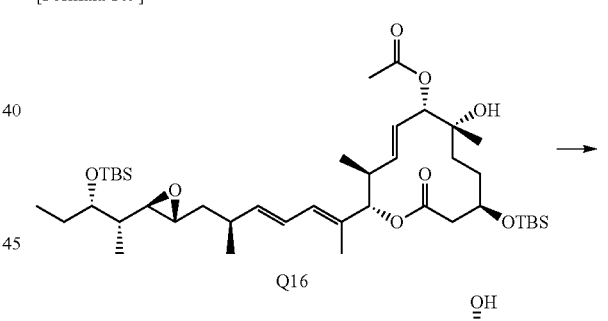

Q16

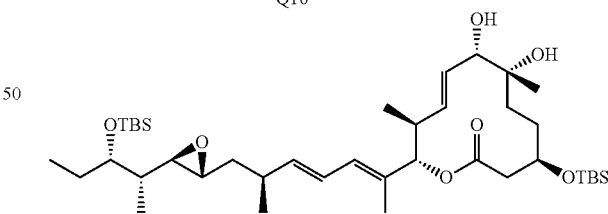

Q17

(2) Synthesis of 3,21-bis{[tert-butyl(dimethyl)silyl]oxy}-pladienolide A (Q17)

Potassium carbonate (304 mg, 2.20 mmol) was added to a methanol (25.0 ml) solution of 3,21-bis{[tert-butyl(dimethyl)silyl]oxy}-pladienolide B (1.68 g, 2.20 mmol) at room temperature. After the reaction solution was stirred at room temperature for 1.5 hours, it was poured into brine, which was then extracted with ethyl acetate. After the organic layer was dried over anhydrous sodium sulfate and the drying agent was filtered off, the organic layer was concentrated under reduced pressure. The obtained residue was purified by silica gel column chromatography (Kanto, commercial name Silica gel 60N, granular, neutral, 0.040 mm-0.100 mm; heptane:ethyl acetate=3:1) to obtain the title compound (1.55 g) as a colorless oil.

400 MHz $^1$H-NMR (CD$_3$OD) δ (ppm) 0.07 (s, 12H), 0.81 (t, J=7.6 Hz, 3H), 0.85 (d, J=7.2 Hz, 6H), 0.91 (s, 18H), 1.08 (d, J=6.4 Hz, 3H), 1.25 (s, 3H), 1.22-1.72 (m, 9H), 1.73 (s, 3H), 2.36 (dd, J=4.8, 13.6 Hz, 1H), 2.40-2.50 (m, 1H), 2.50 (dd, J=3.2, 13.6 Hz, 1H), 2.50-2.60 (m, 1H), 2.61 (dd, J=2.5, 8.4 Hz, 1H), 2.72 (dt, J=2.2, 6.0 Hz, 1H), 3.68 (d, J=9.6 Hz, 1H), 3.68-3.76 (m, 1H), 3.85-3.95 (m, 1H), 4.88 (d, J=12.4 Hz, 1H), 5.38 (dd, J=10.0, 15.2 Hz, 1H), 5.62 (dd, J=8.4, 15.2 Hz, 1H) 5.71 (dd, J=10.0, 15.2 Hz, 1H), 6.08 (brd, J=10.8 Hz, 1H), 6.32 (dd, J=10.8, 15.2 Hz, 1H); LRMS C$_{40}$H$_{74}$NaO$_7$Si$_2$ (M+Na$^+$) Calcd: 745.49, Found: 745.53.

[Formula 110]

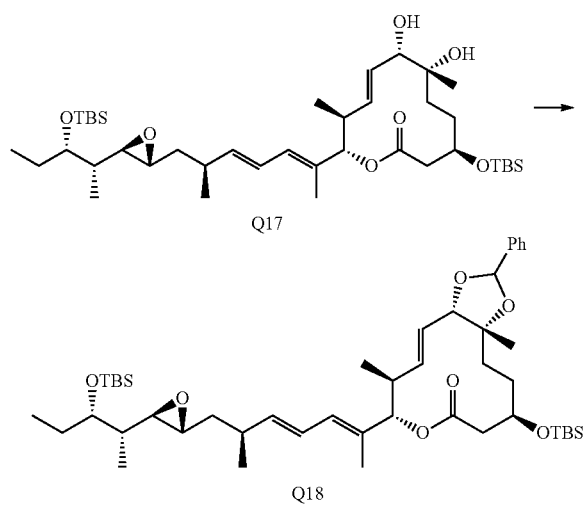

Q17

Q18

(3) Synthesis of 6,7-O-benzylidene-3,21-bis{[tert-butyl(dimethyl)silyl]oxy}-pladienolide A (Q18)

Benzaldehyde dimethylacetal (3.21 ml, 21.4 mmol) and pyridinium p-toluene sulfonate (53.8 mg, 0.214 mmol) were added to an anhydrous dichloromethane (16 ml) solution of 3,21-bis{[tert-butyl(dimethyl)silyl]oxy}-pladienolide A (1.55 g, 2.14 mmol). The reaction solution was stirred at room temperature for 28 hours. The reaction solution was poured into a saturated sodium hydrogen carbonate aqueous solution, which was then extracted with dichloromethane. After the organic layer was washed with water and brine sequentially, it was dried over anhydrous magnesium sulfate. After the drying agent was filtered off, the organic layer was concentrated under reduced pressure. The obtained residue was purified by silica gel column chromatography (Kanto, commercial name Silica gel 60N, granular, neutral, 0.040 mm-0.100 mm; heptane:ethyl acetate=20:1→10:1) to obtain the title compound (1.60 g) as a white amorphous. The title compound was determined to be a mixture of α benzylidene acetal and β benzylidene acetal in a ratio of 1:3.2 by $^1$H-NMR.

Compound Q18β: 400 MHz $^1$H-NMR (CD$_3$OD) δ (ppm) 0.08 (s, 6H), 0.11 (s, 3H), 0.13 (s, 3H), 0.82 (t, J=7.6 Hz, 3H), 0.86 (t, 3H), 0.91 (s, 18H), 0.92 (d, J=6.0 Hz, 3H), 1.08 (d, J=6.8 Hz, 3H), 1.21-1.31 (m, 1H), 1.34 (s, 3H), 1.35-1.60 (m, 5H), 1.64-1.72 (m, 1H), 1.72-1.82 (m, 1H), 1.76 (s, 3H), 1.90-2.00 (m, 1H), 2.25 (dd, J=10.0, 14.8 Hz, 1H), 2.42-2.54 (m, 1H), 2.58-2.65 (m, 2H), 2.66-2.75 (m, 2H), 3.70-3.76 (m, 1H), 4.00-4.10 (m, 1H), 4.37 (d, J=9.6 Hz, 1H), 4.96 (d, J=10.4 Hz, 1H), 5.50 (dd, J=9.6, 15.2 Hz, 1H), 5.64 (dd, J=9.6, 15.2 Hz, 1H), 6.00 (dd, J=10.0, 14.8 Hz, 1H), 6.08 (s, 1H,), 6.09 (d, 9.6 Hz, 1H), 6.33 (dd, J=10.4, 14.8 Hz, 1H), 7.32-7.40 (m, 3H), 7.44-7.50 (m, 2H); LRMS C$_{47}$H$_{78}$NaO$_7$Si$_2$ (M+Na$^+$) Calcd: 833.52, Found: 833.61.

[Formula 111]

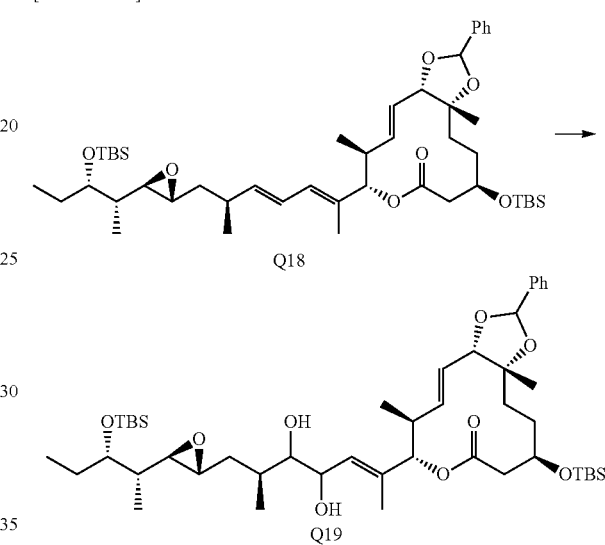

Q18

Q19

(4) Synthesis of (3aS,4E,6S,7S,11R,13aR)-11-{[tert-butyl(dimethyl)silyl]oxy}-7-{(1E,5S)-6-[(2R,3R)-3-((1S,2S)-2-{[tert-butyl(dimethyl)silyl]oxy}-1-methylbutyl)oxiran-2-yl]-3,4-dihydroxy-1,5-dimethylhex-1-en-}-yl'-6,13a-dimethyl-2-phenyl-3a,6,7,10,11,12,13,13a-octahydro-9H-[1,3]dioxolo[4,5-f]oxacyclododecin-9-one (Q19)

6,7-O-benzylidene-3,21-bis{[tert-butyl(dimethyl)silyl]oxy}-pladienolide A (1.60 g, 1.97 mmol) was dissolved in THF (35 ml) and water (10 ml), followed by addition of osmium tetraoxide (1.25 ml, 0.197 mmol, 4% aqueous solution) and 4-methylmorpholine-4-oxide (0.4 ml, 2.17 mmol, 50% aqueous solution) at room temperature, and the mixture was stirred at the same temperature for 24 hours. Subsequently sodium sulfite (0.498 g, 3.94 mmol) was added to the reaction solution, and the mixture was stirred at the same temperature for another hour. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=2:1) to obtain the title compound (1.46 g) as a colorless oil. LRMS C$_{47}$H$_{80}$NaO$_9$Si$_2$ (M+Na$^+$) Calcd: 867.52, Found: 868.68.

[Formula 112]

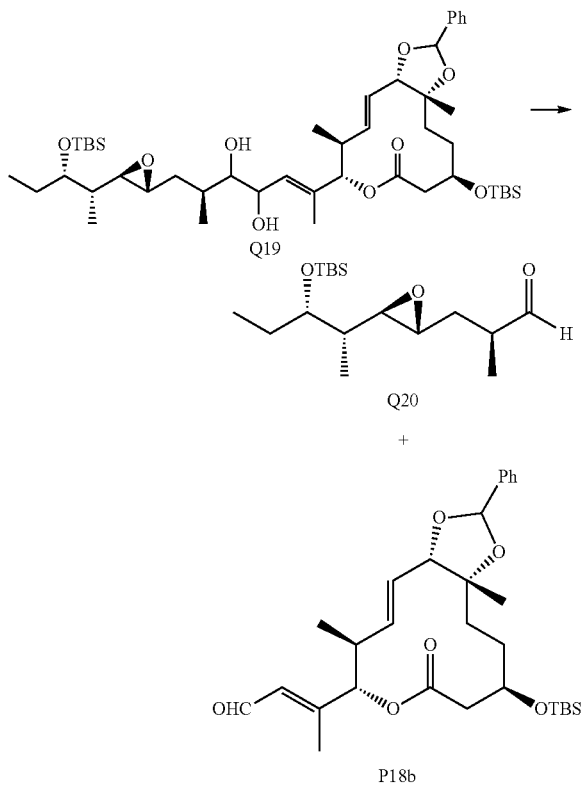

(5) Synthesis of (5R)-4,5-anhydro-5-((1S,2S)-2-{[tert-butyl(dimethyl)silyl]oxy}-1-methylbutyl)-2,3-dideoxy-2-methyl-L-erythro-pentose (Q20) and (3aS,4E,6S,7S,13aR)-11-{[tert-butyl(dimethyl)silyl]oxy}-7-[(E)-2-formyl-1-methyleth-1-en-1-yl]-6,13a-dimethyl-2-phenyl-3a,6,7,10,11,12,13,13a-octahydro-9H-[1,3]dioxolo[4,5-f]oxacyclododecin-9-one (P18b)

(3aS,4E,6S,7S,11R,13aR)-11-{[tert-butyl(dimethyl)silyl]oxy}-7-{(1E,5S)-6-[(2R,3R)-3-((1S,2S)-2-{[tert-butyl(dimethyl)silyl]oxy}-1-methylbutyl)oxiran-2-yl]-3,4-dihydroxy-1,5-dimethylhex-1-en-1-yl}-6,13a-dimethyl-2-phenyl-3a,6,7,10,11,12,13,13a-octahydro-9H-[1,3]dioxolo[4,5-f]oxacyclododecin-9-one (1.46 g, 1.73 mmol) was dissolved in THF (30 ml) and water (7.5 ml), followed by addition of sodium metaperiodate (1.11 g, 5.19 mmol) at room temperature, and the mixture was stirred at the same temperature for 1.5 hours. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=10:1→8:1→5:1) to obtain the title compound Q20 (0.485 g) as a colorless oil and to obtain the title compound P18b (0.803 g) as a colorless oil. The title compound P18b was determined to be a mixture of α benzylidene acetal and β benzylidene acetal in a ratio of 1:3.2 by $^1$H-NMR.

Compound Q20: 400 MHz $^1$H-NMR (CDCl$_3$) δ (ppm) 0.06 (s, 6H), 0.81 (t, J=7.6 Hz, 3H), 0.87 (t, J=6.8 Hz, 3H), 0.89 (s, 9H), 1.20 (dd, J=0.8, 7.6 Hz, 3H), 1.28-1.39 (m, 1H), 1.42- 1.56 (m, 3H), 2.05 (ddd, J=4.4, 8.0, 13.6 Hz, 1H), 2.52-2.63 (m, 1H), 2.67 (dd, J=2.4, 8.0 Hz, 1H), 2.72-2.80 (m, 1H), 3.67-3.76 (m, 1H), 9.67 (d, J=0.8 Hz, 1H); LRMS C$_{17}$H$_{35}$NaO$_3$Si (M+H$^+$) Calcd: 315.24, Found: 315.06.

Compound Q18bβ: 400 MHz $^1$H-NMR (CDCl$_3$) δ (ppm) 0.09 (s, 3H), 0.10 (s, 3H), 0.89 (s, 9H), 0.98 (d, J=6.8 Hz, 3H), 1.35 (s, 3H), 1.34-1.50 (m, 2H), 1.68-1.78 (m, 1H), 1.92-2.04 (m, 1H), 2.18 (brs, 3H), 2.37 (dd, J=9.6, 14.8 Hz, 1H), 2.60 (dd, J=4.0, 14.8 Hz, 1H), 2.60 (dd, J=4.0, 14.8 Hz, 1H), 2.60-2.70 (m, 1H), 3.92-4.02 (m, 1H), 4.31 (d, J=10.0 Hz, 1H), 4.94 (d, J=10.4 Hz, 1H), 5.46 (dd, J=9.6, 15.2 Hz, 1H), 5.92 (dd, J=9.6, 15.2 Hz, 1H), 6.07 (dd, J=1.6, 7.6 Hz, 1H), 6.11 (s, 1H), 7.31-7.42 (m, 3H), 7.45-7.54 (m, 2H), 10.05 (d, J=7.6 Hz, 1H); LRMS C$_{30}$H$_{44}$NaO$_6$Si (M+Na$^+$) Calcd: 551.28, Found: 551.29.

[Formula 113]

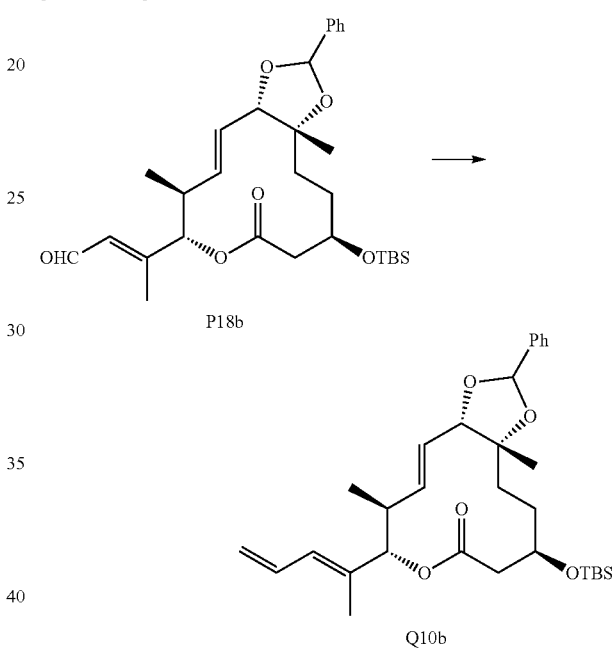

(6) Synthesis of (3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (Q10b)

Potassium tert-butoxide (38.2 mg, 0.341 mmol) was added to an anhydrous THF (3 ml) solution of methyltriphenylphosphonium iodide (100 mg, 0.247 mmol) at room temperature, and it was stirred at room temperature for 30 minutes. Subsequently, a THF (3 ml) solution of (3aS,4E,6S,7S,13aR)-11-{[tert-butyl(dimethyl)silyl]oxy}-7-[(E)-2-formyl-1-methyletha-1-en-1-yl]-6,13a-dimethyl-2-phenyl-3a,6,7,10,11,12,13,13a-octahydro-9H-[1,3]dioxolo[4,5-f]oxacyclododecin-9-one (150 mg, 0.284 mmol) was added dropwise to this reaction solution at room temperature and the reaction solution was stirred for one hour. The reaction solution was diluted with ethyl acetate and washed with distilled water and brine. After the organic layer was dried over anhydrous sodium sulfate and the drying agent was filtered off, the organic layer was concentrated under reduced pressure. The obtained residue was purified by silica gel column chromatography (Kanto, commercial name Silica Gel 60N, 40-100 μm; heptane:ethyl acetate=20:1) to obtain the title compound (44 mg) as a white solid. The title compound was determined to be a mixture of α benzylidene acetal and β benzylidene acetal in a ratio of 1:3.2 by ¹H-NMR.

Q10bβ: 400 MHz ¹H-NMR (CDCl₃) δ (ppm) 0.08 (s, 3H), 0.10 (s, 3H), 0.89 (s, 9H), 0.92 (d, J=6.8 Hz, 3H), 1.28-1.50 (m, 2H), 1.34 (s, 3H), 1.65-1.74 (m, 1H), 1.75 (brs, 3H), 1.98-2.08 (m, 1H), 2.32 (dd, J=10.0, 14.4 Hz, 1H), 2.58 (dd, J=4.0, 14.4 Hz, 1H), 2.58-2.70 (m, 1H), 3.92-4.02 (m, 1H), 4.32 (d, J=10.0 Hz, 1H), 5.00 (d, J=10.8 Hz, 1H), 5.18 (d, 10.0 Hz, 1H), 5.27 (d, J=16.8 Hz, 1H), 5.46 (dd, J=9.6, 15.2 Hz, 1H), 5.89 (dd, J=10.0, 15.2 Hz, 1H), 6.09 (s, 1H), 6.14 (d, J=10.8 Hz, 1H), 6.55 (dt, J=10.8, 16.8 Hz, 1H), 7.28-7.41 (m, 3H), 7.44-7.53 (m, 2H); LRMS C₃₁H₄₆NaO₅Si (M+Na⁺) Calcd: 549.30, Found: 549.26.

(6-1) Alternative synthesis of (3aS,4E,6S,7S,11R,13aR)-11-{[tert-butyl(dimethyl)silyl]oxy}-6,13a-dimethyl-7-[(1E)-1-methylbuta-1,3-dien-1-yl]-2-phenyl-3a,6,7,10,11,12,13,13a-octahydro-9H-[1,3]dioxolo[4,5-f]oxacyclododecin-9-one (Q10b)

The reaction was performed with reference to the literature (Ager, D. J., Synthesis, 1984, 384-398. Hudrlik, P. F.; Peterson, D., J. Am. Chem. Soc., 1975, 97, 1464-1468.).

Magnesium trimethylsilylmethylchloride 1.5M diethyl ether solution (1.33 ml, 2.0 mmol) was added to a diethyl ether solution (20 ml) of (2S,3aS,4E,6S,7S,13aR)-11-{[tert-butyl(dimethyl)silyl]oxy}-7-[(E)-2-formyl-1-methyleth-1-en-1-yl]-6,13a-dimethyl-2-phenyl-3a,6,7,10,11,12,13,13a-octahydro-9H-[1,3]dioxolo[4,5-f]oxacyclododecin-9-one (510 mg, 0.965 mmol) and stirred at the same temperature for 30 minutes. The reaction solution was diluted with diethyl ether, followed by addition of water and sequentially washed with ammonium chloride aqueous solution and brine. The organic layer was dried over anhydrous magnesium sulfate, the drying agent was filtered off and the organic layer was concentrated under reduced pressure.

The obtained crude product was dissolved in THF (15 ml), followed by addition of sulfuric acid (6 drops) at room temperature and the solution was stirred for 1 hour at the same temperature. The reaction solution was diluted with ethyl acetate and washed with water and brine. The organic layer was dried over anhydrous magnesium sulfate, the drying agent was filtered off and the organic layer was concentrated under reduced pressure. The obtained residue was purified by silica gel column chromatography (Merck, commercial name Silica Gel 60, 230-400 mesh; hexane:ethyl acetate=30:1) to obtain the title compound (312 mg) as colorless oil. ¹H-NMR data of title compound by this alternative method are completely identical to those of the title compound obtained by the above (6).

Reference Example 2

[Formula 114]

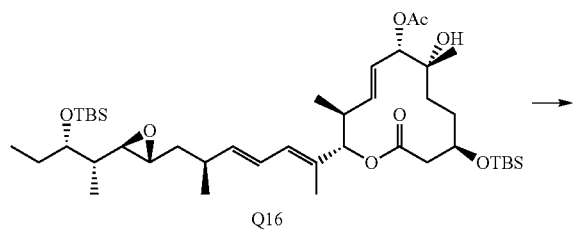

Q16

-continued

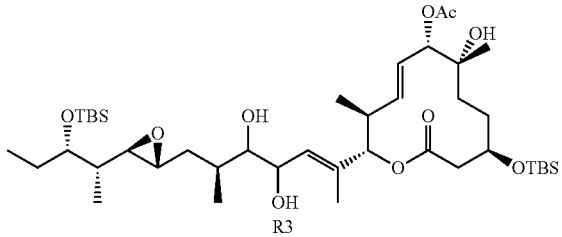

Synthesis of (2S,3S,4E,6S,7R,10R)-10-{[tert-butyl(dimethyl)silyl]oxy}-2-{(1E,5S)-6-[(2R,3R)-3-((1S,2S)-2-{tert-butyl(dimethyl)silyl]oxy}-1-methylbutyl}oxiran-2-yl]-3,4-dihydroxy-1,5-dimethylhexa-1-en-1-yl'-7-hydroxy-3,7-dimethyl-12-oxooxacyclododeca-4-en-6-yl acetate (R6)

3,21-bis{[tert-butyl(dimethyl)silyl]oxy}-pladienolide B (60 mg, 0.078 mmol) was dissolved in THF (1 ml) and water (1 ml), followed by addition of osmium tetraoxide (0.199 ml, 0.016 mmol, 2% aqueous solution) and 4-methylmorpholine-4-oxide (18 μml, 0.078 mmol, 50% aqueous solution) at room temperature. The solution was stirred for 24 hours at the same temperature. Then sodium sulfite (19.8 mg, 0.156 mmol) was added to the reaction solution and further stirred for 1 hour at the same temperature. The reaction solution was diluted by ethyl acetate and washed with the distilled water and brine. The organic layer was dried over anhydrous sodium sulfate, the drying agent was filtered off and the organic layer was concentrated under reduced pressure. The obtained residue was purified by silica gel column chromotography (Kanto, commercial name Silica Gel 60N, 40-100 μm; heptane:ethyl acetate=1:1) to obtain the title compound (67.6 mg) as colorless oil. The title compound was determined as a mixture of diastereomers (1:3).

400 MHz ¹H-NMR (CD₃OD) δ (ppm) 0.11 (s, 12H), 0.85-0.89 (m, 3H), 0.92-0.98 (m, 6H), 0.95 (s, 9H), 0.96 (s, 9H), 0.99 (d, J=6.0 Hz, 0.75H), 1.11 (d, J=6.0 Hz, 2.25H), 1.21 (s, 3H), 1.24-1.74 (m, 9.25H), 1.73 (s, 2.25H), 1.79 (s, 0.75H), 1.84-1.95 (m, 0.75H), 2.10 (s, 3H), 2.36-2.45 (m, 1H), 2.51-2.63 (m, 2H), 2.61 (dd, J=2.0, 8.0 Hz, 0.75H), 2.69 (dd, J=2.0, 8.0 Hz, 0.25H), 2.72-2.84 (m, 1H), 3.28 (dd, J=5.6, 5.6 Hz, 0.75H), 3.45 (dd, J=2.8, 7.2 Hz, 0.25H), 3.74-3.82 (m, 1H), 3.90-4.00 (m, 1H), 4.26-4.39 (m, 1H), 4.87-4.93 (1H, covered with CD₃OD), 4.96 (d, J=9.6 Hz, 0.25H), 5.06 (d, J=9.6 Hz, 0.75H), 5.54-5.68 (m, 2H), 5.75 (dd, J=9.6 Hz, 15.2 Hz, 1H); LRMS C₄₂H₇₈NaO₁₀Si₂ (M+Na⁺) Calcd: 821.50, Found: 821.26.

Reference Example 3

[Formula 115]

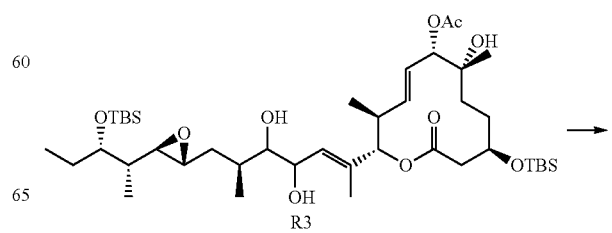

R3

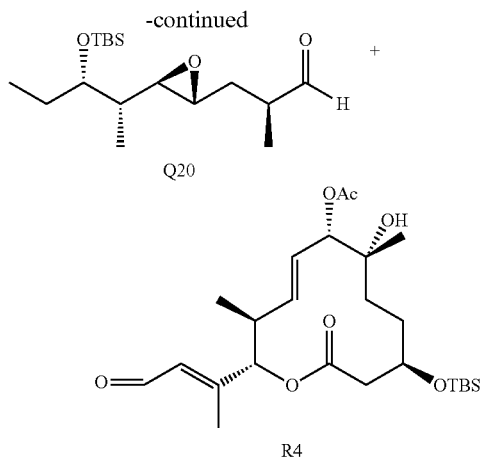

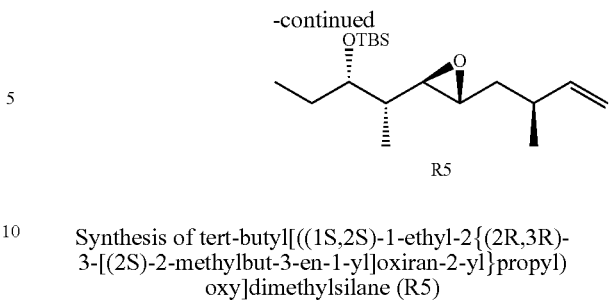

Synthesis of tert-butyl[((1S,2S)-1-ethyl-2{(2R,3R)-3-[(2S)-2-methylbut-3-en-1-yl]oxiran-2-yl}propyl)oxy]dimethylsilane (R5)

This reaction was performed with reference to the literature (Matusbara, S.; Sugihara, M.; Utimoto, K., Synlett, 1998, 97, 313-315.).

Boron trifluoride dimethy ether complex was added to THF solution (6 ml) of 10% wt of tetrahydrofuran suspension (4.56 g, 2.0 mmol) of Nysted reagent ([cyclo-dibromodi-µ-methylene(µ-tetrahydrofuran)trizinc]) at 0° C. and stirred for 5 minutes at the same temperature. THF solution (2 ml) of ((5R)-4,5-anhydro-5-((1S,2S)-2-{[tert-butyl(dimethyl)silyl]oxy}-1-methylbutyl)-2,3-dideoxy-2-methyl-L-erythro-pentose (315 mg, 0.01 mmol) was added to the reaction solution. After the solution was warmed to room temperature, it was stirred for 3 hours. 1M of Hydrochloric acid (3 ml) was added to the reaction solution and it was diluted with hexane, sequentially washed with distilled water and brine. It was dried over anhydrous magnesium sulfate, the drying agent was filtered off and concentrated under reduced pressure. The obtained residue was purified by silica gel column chromotography (Kanto, commercial name Silica Gel 60N, 40-100 µm; heptane:ethyl acetate=50:1→5:1) to obtain the title compound (9.77 mg) as colorless oil.

R4: 400 MHz $^1$H-NMR (CD$_3$OD) δ (ppm) 0.13 (s, 6H), 0.88 (d, J=7.6 Hz, 3H), 0.94 (d, J=7.6 Hz, 3H), 0.96 (s, 9H), 1.10 (d, J=6.8 Hz, 3H), 1.30-1.42 (m, 1H), 1.48-1.64 (m, 4H), 2.34-2.50 (m, 1H), 2.72 (dd, J=2.4, 8.0 Hz, 1H), 2.75-2.85 (m, 1H), 3.69-3.82 (m, 1H) 5.01 (brd, J=10.8 Hz, 1H), 5.08 (brd, J=17.2 Hz, 1H) 5.72-5.86 (m, 1H); LRMS C$_{18}$H$_{36}$NaO$_2$Si (M+Na$^+$) Calcd: 335.24, Found: 335.05.

Synthesis of (5R)-4,5-anhydro-5-((1S,2S)-2-{[tert-butyl(dimethyl)silyl]oxy}-1-methylbutyl)-2,3-dideoxy-2-methyl-L-erythro-pentose (Q20) and (2S,3S,4E,6S,7R,10R)-10-{[tert-butyl(dimethyl)silyl]oxy}-7-hydroxy-3,7-dimethyl-2-[(1E)-1-methyl-3-oxoprop-1-en-1-yl]-12-oxooxacyclododec-4-en-6-yl acetate (R4)

(2S,3S,4E,6S,7R,10R)-10-{[tert-butyl(dimethyl)silyl]oxy}-2-[(1E,5S)-6-[(2R,3R)-3-((1S,2S)-2-{[tert-butyl(dimethyl)silyl]oxy}-1-methylbutyl)oxiran-2-yl]-3,4-dihydroxy-1,5-dimethylhex-1-en-1-yl}-7-hydroxy-3,7-dimethyl-12-oxooxacyclododeca-4-en-6 yl acetate (67.6 mg 0.0847 mmol) was dissolved in THF (1.5 ml) and water (1.5 ml), followed by addition of sodium metaperiodate (181 mg, 0.847 mmol) at room temperature. The reaction solution was stirred for 1 hour at the same temperature. The reaction solution was diluted by distilled water and brine. After the organic layer was dried over anhydrous sodium sulfate, the drying agent was filtered off and the organic layer was concentrated under reduced pressure. The obtained residue was purified by silica gel column chromotography (Kanto, commercial name Silica Gel 60N, 40-100 µm; heptane:ethyl acetate=20:1→2:1) to obtain the title compound R4 (19.3 mg) as colorless oil and the title compound Q20 (36.0 mg) as colorless oil. $^1$H-NMR data of title compound are completely identical to those of the compound Q20 obtained by Reference Example 1 (5).

R4: 400 MHz $^1$H-NMR (CD$_3$OD) δ (ppm) 0.12 (s, 3H), 0.14 (m, 3H), 0.95 (s, 9H), 1.00 (d, J=6.8 Hz, 3H), 1.24 (s, 3H), 1.23-1.84 (m, 4H), 2.10 (s, 3H), 2.22 (d, J=1.2 Hz, 3H), 2.44 (dd, J=4.8, 13.6 Hz, 1H), 2.55-2.66 (m, 2H), 3.93-4.03 (m, 1H), 4.93 (d, J=10.8 Hz, 1H), 5.06 (d, J=9.6 Hz, 1H), 5.64 (dd, J=10.0, 15.2 Hz, 1H), 5.80 (dd, J=9.6, 15.2 Hz, 1H), 6.08 (brd, J=8.0 Hz, 1H), 10.06 (d, J=8.0 Hz, 1H); LRMS C$_{25}$ClH$_{42}$OSi (M+Cl$^-$) Calcd: 517.24, Found: 7.09.

Reference Example 4

[Formula 116]

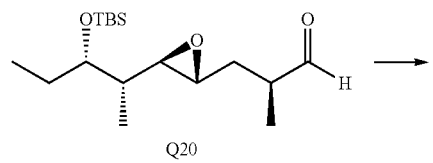

Reference Example 5

[Formula 117]

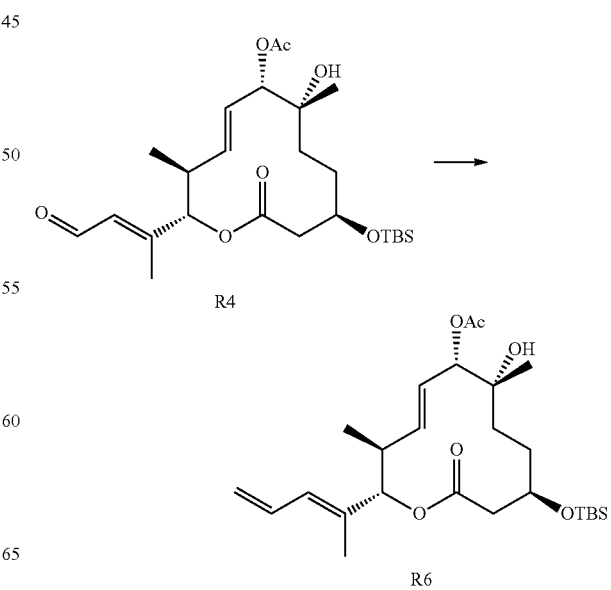

Synthesis of (2S,3S,4E,6S,7R,10R)-7-hydroxy-3,7-dimethyl-2-[(1E)-1-methylbuta-1,3-dien-1-yl]-12-oxo-10-{[tert-butyl(dimethyl)silyl]oxy}oxacyclododec-4-en-6-yl acetate (R6)

This reaction was performed with reference to the literature (Pine, S. H.; Zahler, R.; Evans, D. A.; Grubbs, R. H., J. Am. Chem. Soc., 1980, 3270-3272.).

THF (0.8 ml) of (2S,3S,4E,6S,7R,10R)-10-{tert-butyl(dimethyl)silyl]oxy}-7-hydroxy-3,7-dimethyl-2-[(1E)-1-methyl-3-oxoprop-1-en-1-yl]-12-oxooxacyclododec-4-en-6-yl acetate (86.9 mg, 0.18 mmol) and toluene (6.1 ml) was dissolved as a mixed solvent and it was cooled to −40° C. Pyridine (0.15 ml, 1.89 mmol) and 0.5 M toluene solution of Tebbe reagent (chlorobis(cyclopentadienyl)-(dimethylaluminium)-(methylenetitanium) were added to it and the reaction solution was stirred for 30 minutes at the same temperature. The reaction solution was warmed to −20° C. and stirred for further 30 minutes. Distilled water was added to the reaction solution and it was diluted with ethyl acetate and washed sequentially with distilled water and brine. After the reaction solution was dried over anhydrous sodium sulfate, the drying agent was filtered off and was concentrated under reduced pressure. The obtained residue was purified by silica gel column chromatography (Merck, commercial name; Silica Gel 60, 230-400 mesh; hexane; diethyl ether=4:1) to obtain the title compound (41 mg) as a colorless amorphous.

400 MHz $^1$H-NMR (CDCL$_3$) δ (ppm) 0.06 (s, 3H), 0.07 (s, 3H), 0.89 (d, J=6.4 Hz, 3H), 0.97 (s, 9H), 1.21 (s, 3H), 1.28-1.50 (m, 3H), 1.62-1.70 (m, 1H), 1.72 (brs, 3H), 2.10 (s, 3H), 2.39 (dd, J=4.4, 14.0 Hz, 1H), 2.46 (dd, J=3.6, 14.0 Hz, 1H), 2.44-2.55 (m, 1H), 3.80-3.90 (m, 1H), 4.97 (d, J=10.8 Hz, 1H), 5.07-5.09 (m, 1H), 5.15 (dd, J=1.6, 10.0 Hz, 1H), 5.24 (dd, J=1.6, 16.8 Hz, 1H), 5.56-5.72 (m, 2H), 6.14 (d, J=10.8 Hz, 1H), 6.53 (dt, J=10.0, 16.8 Hz, 1H); LRMS C$_{26}$H$_{44}$NaO$_6$Si (M+Na$^+$) Calcd: 503.28, Found: 503.21.

Reference Example 6

[Formula 118]

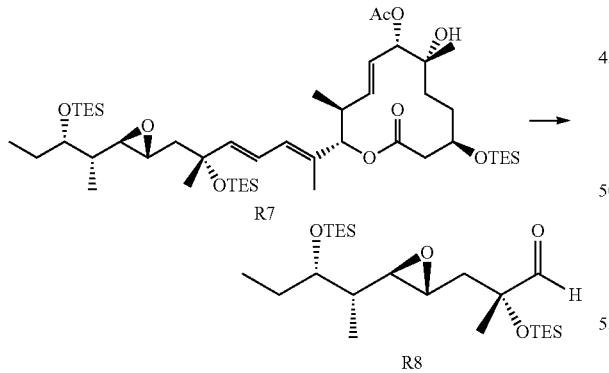

Synthesis of 4,5-anhydro-3,6,8,9-tetradeoxy-6-methyl-2-C-methyl-2,7-bis-O-(triethylsilyl)-L-glycero-D-gluco-nonose (R8)

3,16,21-tris-[(triethylsilyl)oxy]-pladienolide D (50 mg, 55.9 μl; Example 46 of WO 03/099813) was dissolved in dichloromethane. The reaction solution was cooled to −78° C. Ozone (flow rate 2 l/min, voltage 90 V) was blown into the reaction solution for 10 minutes during stirring. After dimethyl sulfide (10.4 mg, 0.168 mmol) was added, the reaction solution was warmed to room temperature, stirred for 1 hour and was concentrated under reduced pressure. The obtained residue was purified by silica gel column chromatography (Kanto, commercial name Silica Gel 60N, granular, neutral, 0.040 mm-0.100 mm; n-heptane:ethyl acetate=30:1) to obtain the title compound (18.5 mg) as colorless oil.

400 MHz $^1$H-NMR (CD$_3$OD) δ (ppm) 0.64-0.76 (m, 12H), 0.88 (t, J=7.6 Hz, 3H), 0.94 (d, J=7.6 Hz, 3H), 0.99 (t, J=7.6 Hz, 9H), 1.00 (t, J=7.6 Hz, 9H), 1.28-1.39 (m, 1H), 1.42 (s, 3H), 1.52-1.63 (m, 2H), 1.81-1.94 (m, 2H), 2.70 (dd, J=2.2, 8.0 Hz, 1H), 2.92 (dt, J=2.2, 8.0 Hz, 1H), 3.80 (dt, J=3.2, 6.0 Hz, 1H), 9.61 (s, 1H).

Reference Example 7

[Formula 119]

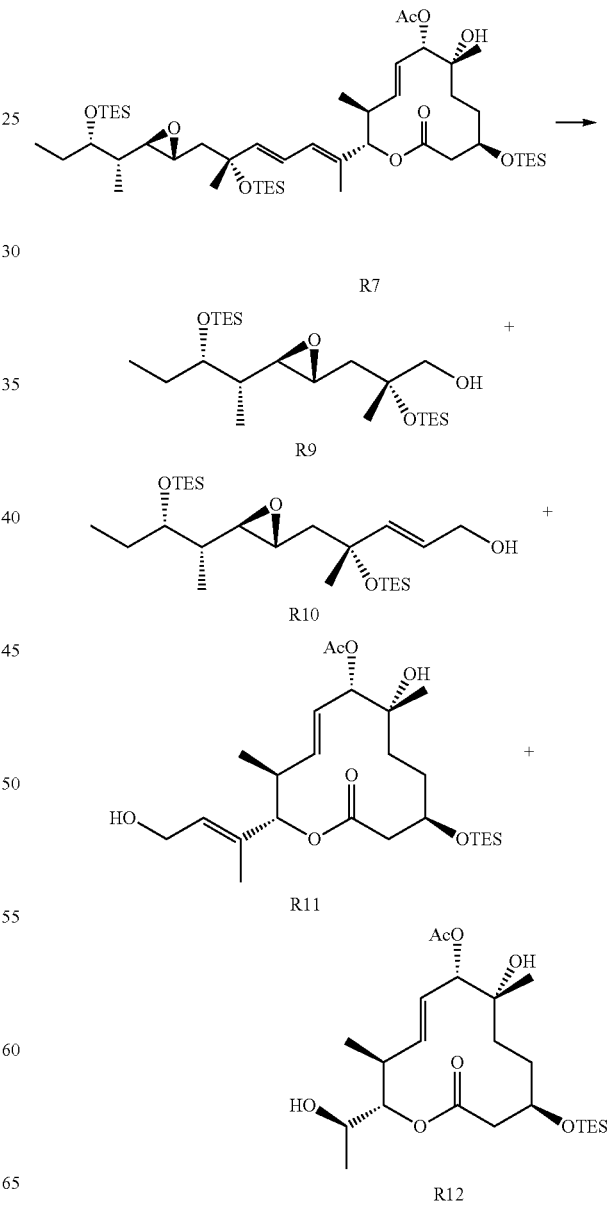

Synthesis of 5,6-anhydro-1,2,4,7-tetradeoxy-4-methyl-8-C-methyl-3,8-bis-O-triethylsilyl)-L-glycero-D-galacto-nonitol (R9), (1R)-1,2-anhydro-3,5-dideoxy-4-C-[(1E)-3-hydroxyprop-1-en-1-yl]-1-{(1S,2S)-1-methyl-2-[(triethylsilyl)oxy]butyl}-4-O-(triethylsilyl)-D-erythro-pentitol (R10), (2S,3S,4E,6S,7R,10R)-7-hydroxy-2-[(1E)-3-hydroxy-1-methyl-prop-1-en-1-yl]-3,7-dimethyl-12-oxo-10-[(triethysilyl)oxy]oxacyclododec-4-en-6-yl acetate (R11) and (2S,3S,4E,6S,7R,10R)-7-hydroxy-2-[(hydroxyethyl)-3,7-dimethyl-12-oxo-10-[(triethylsilyl)oxy]oxacyclododec-4-en-6-yl acetate (R12)

3,16,21-tris-[(triethylsilyl)oxy]-pladienolide D (21 mg, 0.235 mmol) was dissolved in a mixture solvent of dichloromethane (25 ml) and methanol (25 ml). This reaction solution was cooled to −78° C. and Ozone (flow rate 2 l/min, voltage 90 V) was blown into the reaction solution for 3 minutes during stirring. After adding sodium borohydride (88.9 mg, 2.35 mmol), the reaction solution was warmed to 0° C. and stirred for 1.5 hours. The reaction solution was diluted by ethyl acetate and washed with brine. The organic layer was dried over anhydrous sodium sulfate, the drying agent was filtered off and the organic layer was concentrated under reduced pressure. The obtained residue was purified by silica gel column chromatography (Merck, commercial name Silica Gel 60, 230-400 mesh; hexane: ethyl acetate=10:1→3:2→1:2). The title compound R9 (77.3 mg) was obtained as colorless oil. The title compound R10 (17.3 mg) was obtained as colorless oil. The title compound R11 (38.5 mg) was obtained as colorless oil. The title compound R12 (49.1 mg) was obtained as colorless oil.

R9: 400 MHz $^1$H-NMR (CD$_3$OD) δ (ppm) 0.64-0.76 (m, 12H), 0.89 (t, J=7.2 Hz, 3H), 0.98 (d, J=7.6 Hz, 3H), 0.95 (t, J=8.0 Hz, 9H), 1.00 (t, J=8.0 Hz, 9H), 1.26 (s, 3H), 1.28-1.40 (m, 1H), 1.52-1.65 (m, 2H), 1.68 (dd, J=6.4, 14.4 Hz, 1H), 1.77 (dd, J=5.2, 14.4 Hz, 1H), 2.71 (dd, J=2.4, 8.0 Hz, 1H), 2.95-3.02 (m, 1H), 3.48 (d, J=9.6 Hz, 1H), 3.55 (d, J=9.6 Hz, 1H), 3.79 (dt, J=3.2, 6.4 Hz, 1H),; LRMS C$_{23}$H$_{50}$N$_a$O$_4$Si$_2$ (M+Na$^+$) Calcd: 469.31, Found: 469.16

R10: 400 MHz $^1$H-NMR (CD$_3$OD) δ (ppm) 0.69 (q, J=8.0 Hz, 6H), 0.70 (q, J=8.0 Hz, 6H), 0.89 (t, J=7.6 Hz, 3H), 0.96 (d, J=7.2 Hz, 3H), 1.02 (t, J=8.0 Hz, 9H), 1.03 (t, J=8.0 Hz, 9H), 1.28-1.40 (m, 1H), 1.46 (s, 3H), 1.52-1.66 (m, 1H), 1.70-1.84 (m, 1H), 2.69 (dd, J=2.4, 8.4 Hz, 1H), 2.95 (dt, J=2.4, 5.6 Hz, 1H), 3.81 (dt, J=3.2, 6.4 Hz, 1H), 4.12 (d, J=4.0 Hz, 2H), 5.78-5.88 (m, 2H),; LRMS C$_{25}$H$_{52}$N$_a$O$_4$Si$_2$ (M+Na$^+$) Calcd: 495.33, Found: 495.31.

R11: LRMS C$_{25}$H$_{44}$N$_a$O$_7$Si (M+Na$^+$) Calcd: 507.28, Found: 507.27.

R12: 400 MHz $^1$H-NMR (CD$_3$OD) δ (ppm) 0.66 (q, J=8.0 Hz, 6H), 1.02 (t, J=8.0 Hz, 9H), 1.11 (d, J=6.8 Hz, 3H), 1.16 (d, J=6.4 Hz, 3H), 1.24 (s, 3H), 1.34-1.72 (m, 4H), 2.13 (s, 3H), 2.45-2.68 (m, 2H), 2.73-2.85 (m, 1H), 3.85-3.95 (m, 1H), 3.98-4.12 (m, 1H), 4.77 (d, J=10.4 Hz, 1H), 5.13 (d, J=9.2 Hz, 1H), 5.64-5.80 (m, 2H); LRMS C$_{23}$H$_{42}$N$_a$O$_7$Si (M+Na$^+$) Calcd: 481.26, Found: 481.22.

What is claimed is:

1. A process for producing a compound represented by Formula (6):

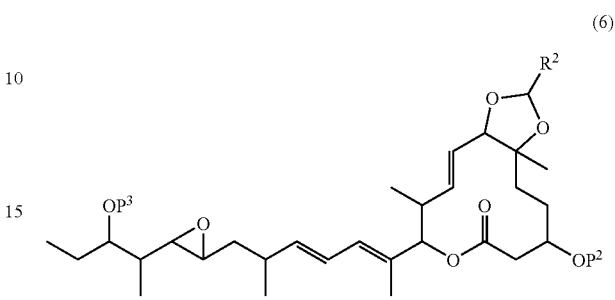

(6)

wherein P$^2$, P$^3$ and R$^2$ are the same as defined below, characterized by comprising reacting a compound represented by Formula (7):

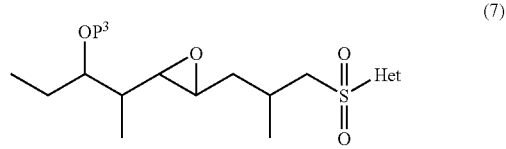

(7)

wherein P$^3$ means a protecting group for hydroxy group; and Het means a 1-phenyl-1H-tetrazol-5-yl group, with a compound represented by Formula (8):

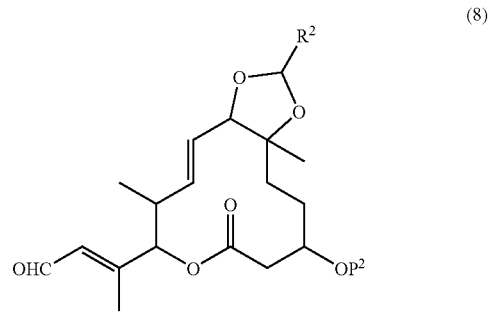

(8)

wherein P$^2$ means a protecting group for hydroxy group; and R$^2$ means a phenyl group which may be substituted, in the presence of a base.

2. The production process according to claim 1, wherein the base is potassium bis(trimethylsilyl)amide.

* * * * *